United States Patent
Yamashita et al.

(10) Patent No.: US 11,903,481 B2
(45) Date of Patent: *Feb. 20, 2024

(54) PLAQUE DETECTING DEVICE AND TOOTHBRUSH INCORPORATING SAME

(71) Applicants: Colgate-Palmolive Company, New York, NY (US); Omron Healthcare Co., Ltd., Kyoto (JP)

(72) Inventors: Hideyuki Yamashita, Kyoto (JP); Kosuke Abe, Kyoto (JP); Hideaki Yoshida, Kyoto (JP); Yasuhiro Kawabata, Kyoto (JP); Masashi Kitamura, Kyoto (JP)

(73) Assignees: Colgate-Palmolive Company, New York, NY (US); Omron Healthcare Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/577,112

(22) Filed: Jan. 17, 2022

(65) Prior Publication Data

US 2022/0183457 A1    Jun. 16, 2022

Related U.S. Application Data

(63) Continuation of application No. 16/921,114, filed on Jul. 6, 2020, now Pat. No. 11,246,404, which is a
(Continued)

(30) Foreign Application Priority Data

Mar. 24, 2016  (JP) ................................. 2016-060012
Feb. 17, 2017  (JP) ................................. 2017-028048

(51) Int. Cl.
*A46B 15/00*    (2006.01)
*A61B 5/00*     (2006.01)

(52) U.S. Cl.
CPC ...... *A46B 15/0034* (2013.01); *A46B 15/0036* (2013.01); *A61B 5/0088* (2013.01); *A46B 2200/1066* (2013.01); *A61B 5/0071* (2013.01)

(58) Field of Classification Search
CPC ............ A46B 15/0034; A46B 15/0036; A46B 2200/1066; A46B 9/04; A46B 15/00;
(Continued)

(56) References Cited

U.S. PATENT DOCUMENTS 4,290,433 A    9/1981  Alfano
5,382,163 A    1/1995  Putnam
(Continued)

FOREIGN PATENT DOCUMENTS

EP    3267182 A1 *  1/2018  ......... A46B 15/0036
JP    H11-047166     2/1999
(Continued)

OTHER PUBLICATIONS

International Search Report and Written Opinion of the International Searching Authority in International Application No. PCT/JP2017/010328, dated May 9, 2017.
(Continued)

*Primary Examiner* — Christine S. Kim

(57) ABSTRACT

The plaque detecting device of the present invention comprises a light emitting unit (450) which irradiates ultraviolet or blue excitation light (L) toward the tooth surface (99a), and a first and second light receiving units (402) which receive radiated light (L') from the tooth surface (99a). The first light receiving unit extracts the spectral component of a first wavelength region including the wavelength range of fluorescent light specific to plaque from the radiated light (L'), and obtains a first output value corresponding to the intensity of that spectral component. The second light receiving unit extracts, from the radiated light (L'), the
(Continued)

spectral component of a second wavelength region containing the wavelength range of the fluorescent light specific to enamel and having a predetermined lower limit wavelength below the lower limit wavelength of the first wavelength region, and obtains a second output value corresponding to the intensity of this spectral component. Determination of the relative magnitude of the ratio between the first output value and the second output value as compared to a first threshold value is performed. Determination of the relative magnitude of the difference between the first output value and the second output value as compared to a second threshold value is performed.

14 Claims, 37 Drawing Sheets

Related U.S. Application Data continuation of application No. 16/087,938, filed as application No. PCT/JP2017/010328 on Mar. 15, 2017, now Pat. No. 10,743,649.

(58) Field of Classification Search
CPC ... A61B 5/0088; A61B 5/0071; A61B 5/6887; A61B 2560/0214; A61B 2560/0456; A61B 5/0084; G01N 2021/6421; G01N 2201/08; G01N 21/6486; G01N 21/64; A61C 19/04
See application file for complete search history.

(56) References Cited

U.S. PATENT DOCUMENTS

| | | | |
|---|---|---|---|
| 6,485,300 B1 | 11/2002 | Muller et al. | |
| 8,512,040 B2 | 8/2013 | Binner et al. | |
| 8,992,216 B2 | 3/2015 | Karazivan | |
| 9,723,993 B2 | 8/2017 | Vermeulen | |
| 9,901,256 B2 | 2/2018 | Seibel et al. | |
| 2007/0105069 A1 | 5/2007 | Yamagishi | |
| 2008/0280260 A1 | 11/2008 | Belikov et al. | |
| 2011/0151409 A1 | 6/2011 | Binner | |
| 2011/0296643 A1 | 12/2011 | Shepherd et al. | |
| 2011/0314618 A1* | 12/2011 | Binner | A46B 15/0034 433/29 |
| 2011/0318712 A1* | 12/2011 | Reddy | A61B 5/0088 433/216 |
| 2013/0203008 A1 | 8/2013 | Kressman et al. | |
| 2016/0038033 A1* | 2/2016 | Lal | A61B 5/0088 433/29 |
| 2019/0167399 A1 | 6/2019 | Kawabata et al. | |

FOREIGN PATENT DOCUMENTS

| | | | | |
|---|---|---|---|---|
| JP | 2002-515276 | | 5/2002 | |
| JP | 2003-210497 | | 7/2003 | |
| JP | 2016-501095 | | 1/2016 | |
| JP | 2016-501098 | | 1/2016 | |
| JP | 2016538903 A | * | 12/2016 | ........... A61B 5/0088 |
| JP | 2017153841 A | * | 9/2017 | |
| JP | 6681875 B2 | * | 4/2020 | ........ A46B 15/0036 |
| WO | 2015/056197 | | 4/2015 | |
| WO | 2015/082390 | | 6/2015 | |
| WO | 2017/164026 | | 9/2017 | |

OTHER PUBLICATIONS

Yoshitani et al., LuminO: A plaque aware toothbrush, Sep. 12, 2016, pp. 1-11 (Year: 2016).

* cited by examiner

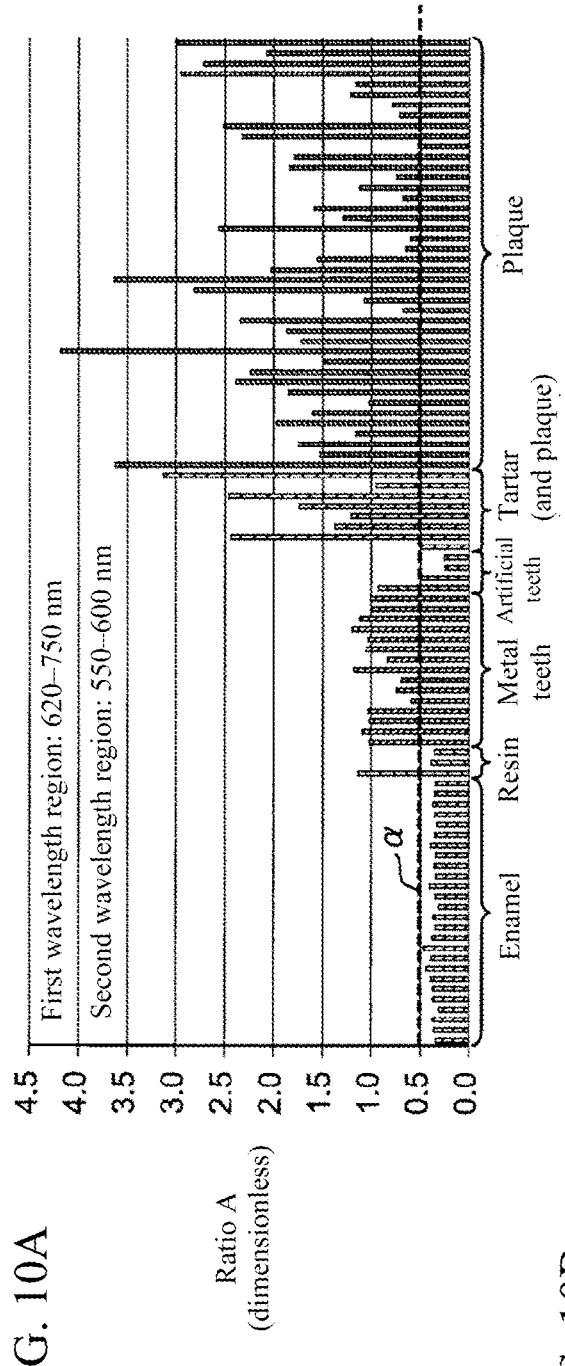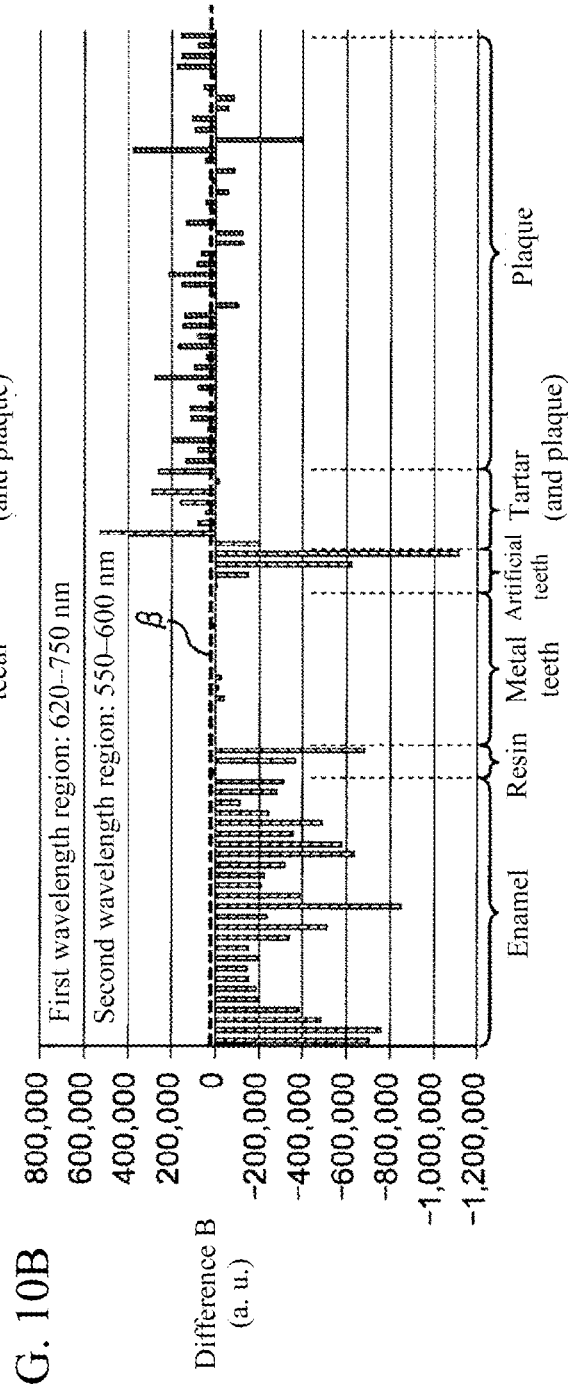

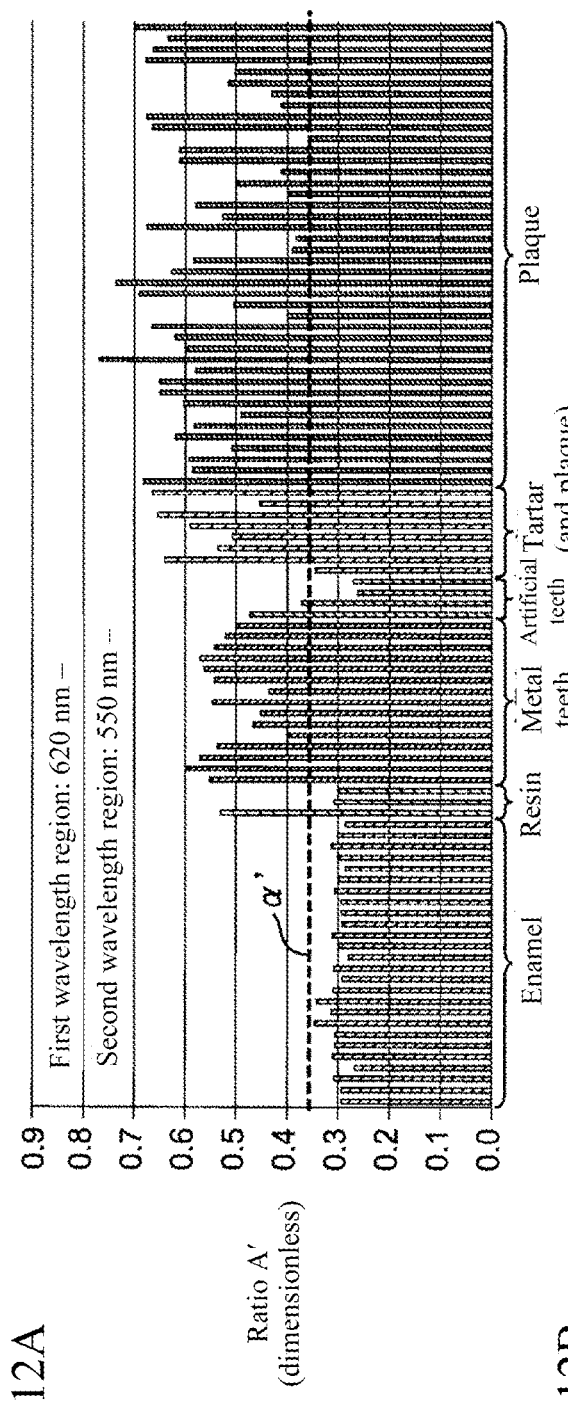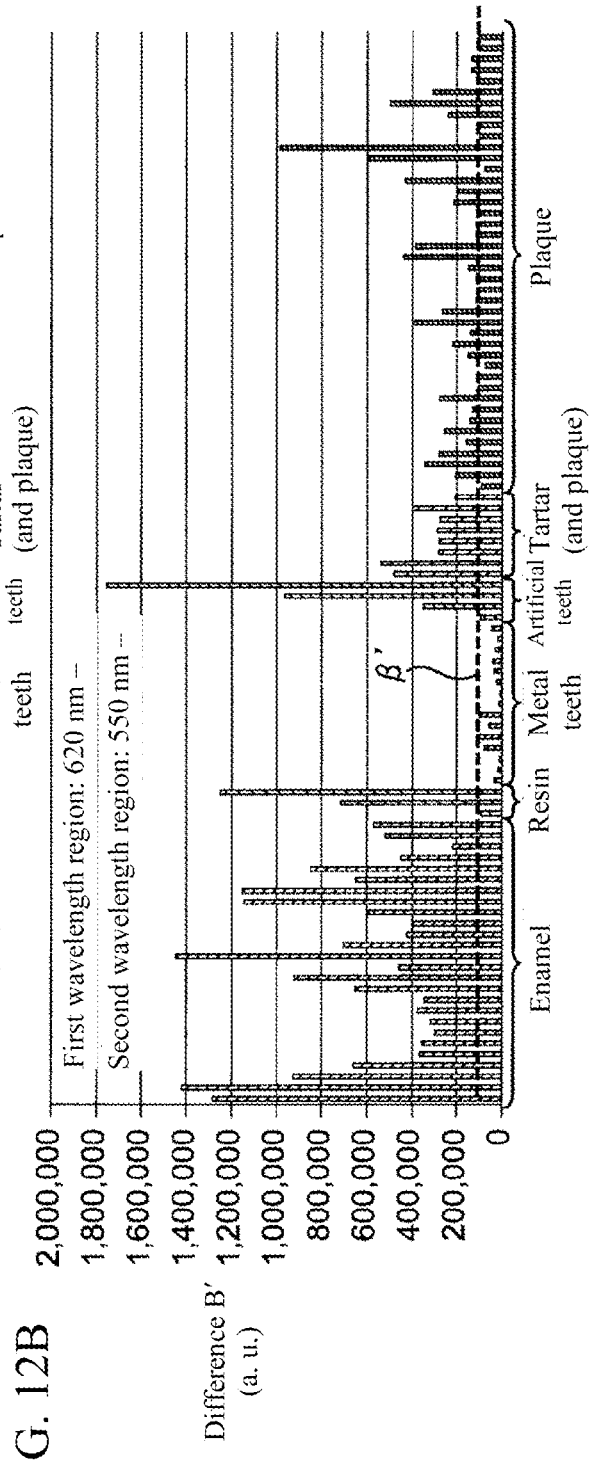

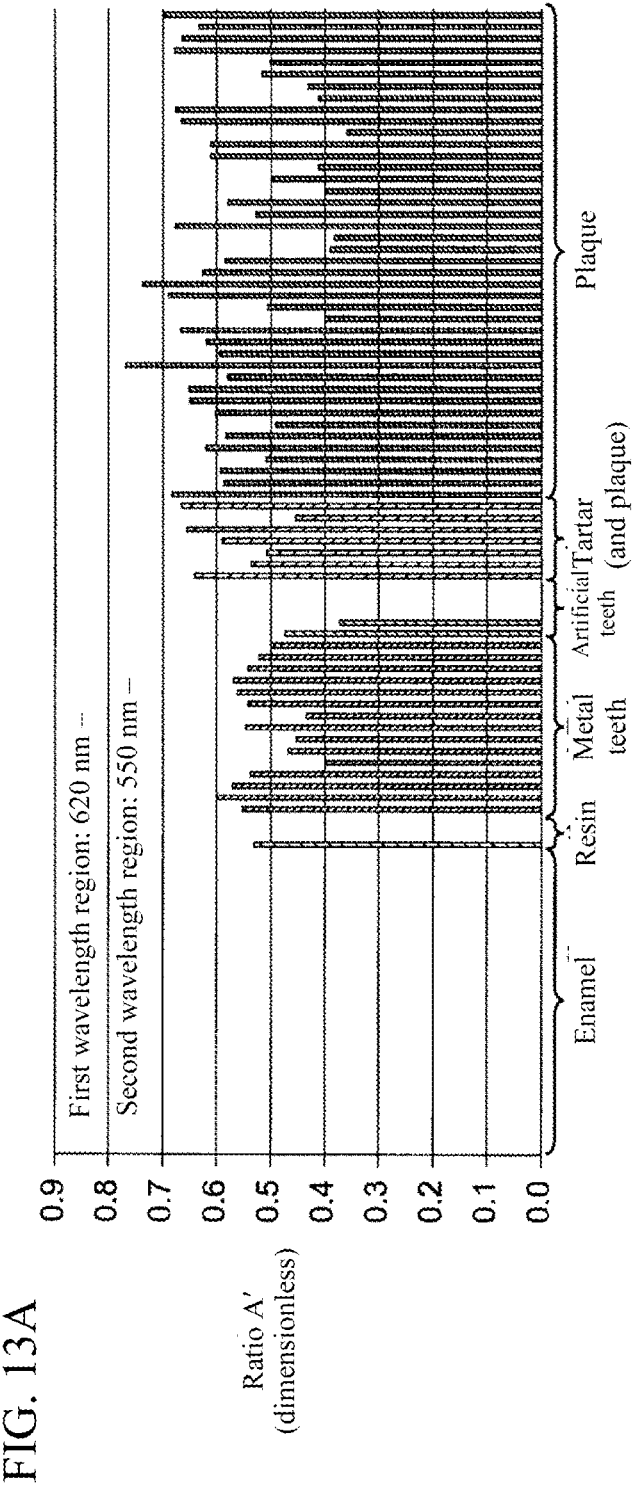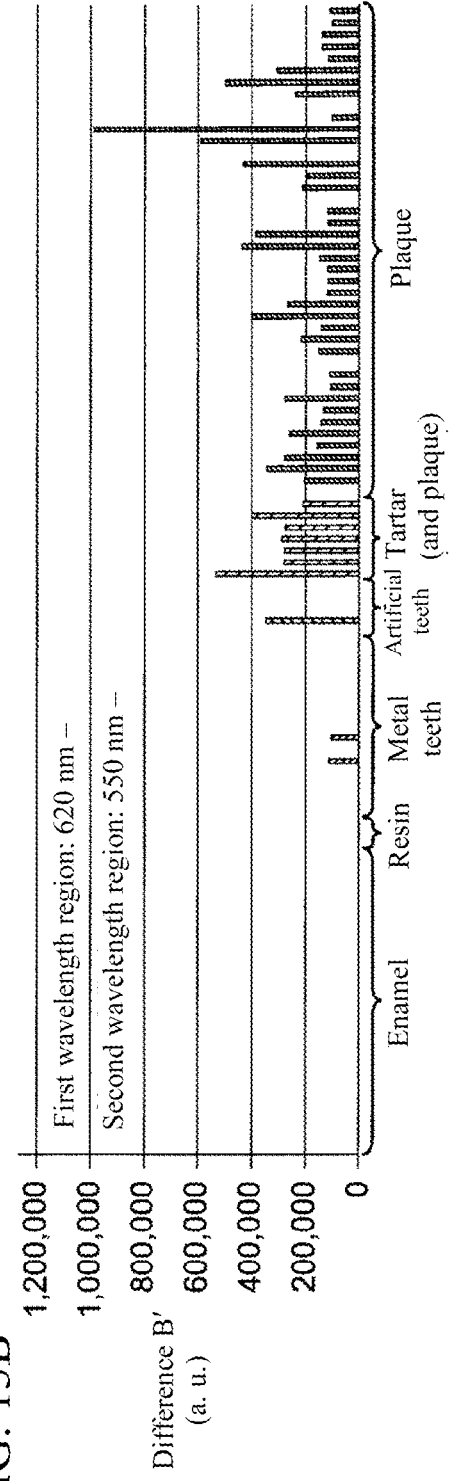
FIG. 13A
FIG. 13B

PLAQUE DETECTING DEVICE AND TOOTHBRUSH INCORPORATING SAME

CROSS-REFERENCE TO RELATED APPLICATIONS

The present application is a continuation of U.S. patent application Ser. No. 16/921,114, filed Jul. 6, 2020, which is a continuation of U.S. patent application Ser. No. 16/087,938, filed Sep. 24, 2018, (now U.S. Pat. No. 10,743,649) which is a National Stage Entry of PCT Application No. PCT/JP2017/010328, filed on Mar. 15, 2017, which claims priority to Japanese Patent Application No. 2017-028048, filed on Feb. 17, 2017, and Japanese Patent Application No. 2016-060012, filed on Mar. 24, 2016, the entireties of which are incorporated herein by reference.

TECHNICAL FIELD

This invention relates to a plaque detecting device, more specifically, a plaque detecting device which irradiates light onto the surface of a tooth and determines the presence or absence of plaque based on fluorescent light coming from the tooth surface or plaque.

This invention furthermore relates to a tooth brush incorporating such a plaque detecting device.

BACKGROUND ART

Plaque detecting devices of this sort known in the prior art include, for example, devices which compare the intensity of fluorescent light coming from a tooth surface substantially without deposits (plaque, bacteria, tartar, calculus, etc.) to the intensity of fluorescent light from the tested tooth surface to determine the presence or absence of biological deposits on the tested tooth surface, as disclosed in patent document 1 (Published Japanese Translation of a PCT Application 2002-515276).

PRIOR ART DOCUMENTS

Patent Documents

Patent Document 1: Published Japanese Translation of a PCT Application 2002-515276.

SUMMARY OF THE INVENTION

Problem to be Solved by the Invention

When using the device described in aforementioned patent document 1, the user needs to find a "tooth surface without biological deposits" to serve as a basis for comparison, and save the intensity of fluorescent light from that tooth surface as a reference. However, this involves the problem that it is difficult for a regular user to find a "tooth surface without biological deposits" (usually, the user cannot be sure), and a calibration-like operation of saving the reference becomes necessary, which takes time and is troublesome.

The problem to be solved by this invention therefore consists in providing a plaque detecting device allowing a user to determine the presence or absence of plaque through a simple operation.

The problem to be solved by this invention further consists in providing a tooth brush incorporating such a plaque detecting device.

Means for Solving the Problem

To solve the aforementioned problem, the plaque detecting device of this invention is a plaque detecting device which determines the presence or absence of plaque on a tooth surface, characterized in that it comprises a light emitting unit which irradiates ultraviolet or blue excitation light toward said tooth surface, and a first and second light receiving units which receive radiated light from said tooth surface induced by said excitation light, wherein said first light receiving unit extracts, from said radiated light, a spectral component of a first wavelength region having a predetermined lower limit wavelength and including the wavelength range of fluorescent light specific to plaque, and obtains a first output value corresponding to the intensity of the spectral component of this first wavelength region, and said second light receiving unit extracts, from said radiated light, a spectral component of a second wavelength region having a predetermined lower limit wavelength lower than the lower limit wavelength of said first wavelength region and including the wavelength range of fluorescent light specific to enamel, and obtains a second output value corresponding to the intensity of the spectral component of this second wavelength region, the plaque detecting device further comprising a first determination unit which performs determination of the relative magnitude of the ratio between said first output value and said second output value as compared to a predetermined first threshold value, and a second determination unit which performs determination of the relative magnitude of the difference between said first output value and said second output value as compared to a predetermined second threshold value.

As is known, in the light radiated from a tooth surface, "fluorescent light specific to plaque" has a peak wavelength of approximately 630 nm, and the spectral component of this peak is distributed over a range of approximately ±10 nm relative to the peak wavelength. Furthermore, "fluorescent light specific to enamel" has a peak wavelength of approximately 480 nm. The spectral component to the longer wavelength side of this peak is broadly distributed to about 750 nm from the peak wavelength.

The upper limit wavelength of the first wavelength region may be left undetermined or may be determined to be, for example, 750 nm or lower. The upper limit wavelength of the second wavelength region may be left undetermined or may be determined to be, for example, 600 nm or lower.

The "intensity" of the spectral components of the first wavelength region and second wavelength region corresponds to the magnitude obtained by integrating (or summing) the spectral component of the extracted wavelength region over that wavelength region.

For the "ratio" between the first output value and the second output value, either the first output value or the second output value may be used as the numerator (or denominator). Similarly, for the "difference" between the first output value and the second output value, either one may be used as the minuend (or subtrahend).

In the plaque detecting device of this invention, the light emitting unit irradiates ultraviolet or blue excitation light toward the tooth surface. The first light receiving unit and second light receiving unit each receive the radiated light from the tooth surface induced by the excitation light. The first light receiving unit extracts, from the radiated light, a spectral component of a first wavelength region having a predetermined lower limit wavelength and including the wavelength range of fluorescent light specific to plaque, and obtains a first output value corresponding to the intensity of the spectral component of this first wavelength region. Furthermore, the second light receiving unit extracts, from the radiated light, a spectral component of a second wavelength region having a predetermined lower limit wavelength lower than the lower limit wavelength of the first wavelength region and including the wavelength range of fluorescent light specific to enamel, and obtains a second output value corresponding to the intensity of the spectral component of this second wavelength region. The first determination unit performs determination of the relative magnitude of the ratio between the first output value and the second output value as compared to a predetermined first threshold value. According to the determination results from this first determination unit, substances which may be present on the tooth surface (namely, enamel, resin, metal teeth, artificial teeth (ceramic or plastic), tartar and plaque) can be identified as belonging either to the group consisting of enamel, resin and artificial teeth (ceramic or plastic), or the group consisting of metal teeth, tartar and plaque (the basis for such identification will be described later). The second determination unit performs determination of the relative magnitude of the difference between the first output value and the second output value as compared to a predetermined second threshold value. According to the determination results from this second determination unit, the substances which may be present on a tooth surface can be identified as belonging either to the group consisting of enamel, resin, metal teeth and artificial teeth (ceramic or plastic), or the group consisting of tartar and plaque. Furthermore, the group consisting of metal teeth can be identified in distinction to the group consisting of enamel, resin, artificial teeth (ceramic or plastic), tartar and plaque (the basis for such identification will be described later). Therefore, based on a combination of the determination results from the first determination unit and the determination results from the second determination unit, it can be identified if the substance present on a tooth surface is plaque (or tartar) or not.

For instance, if the substance present on a tooth surface is plaque (or tartar), for example, first, based on the determination of the first determination unit, the substance present on the tooth surface will be identified as being a substance belonging to the group consisting of metal teeth, tartar and plaque. Next, based on the determination of the second determination unit, the substance will be identified as being not metal teeth but rather plaque (or tartar).

In this way, with this plaque detecting device, the substance present on a tooth surface can be identified as being or not being plaque (or tartar) based on a combination of the determination results from the first determination unit and the determination results from the second determination unit.

Here, with this plaque detecting device, unlike the device described in patent document 1, the user does not need to find a "tooth surface without biological deposits" to serve as a basis for comparison, nor is there a need for the calibration-type operation of saving a reference. Therefore, the user is able to obtain determination results concerning the presence or absence of plaque (or tartar) through a simple operation, for example, by simply arranging the light emitting unit and light receiving unit so as to face a tooth surface, and instructing the start of operation (switching on) of the plaque detecting device. Since tartar is plaque which has gradually changed and become deposited on a tooth surface, it is difficult to completely distinguish the two in terms of substance.

In one embodiment, the plaque detecting device is characterized in that it comprises a first zero point adjustment unit which performs adjustment by subtracting the component due to ambient light around said tooth surface from said first and second output values, wherein said first and second determination units use said first and second output values, which have been adjusted by said first zero point adjustment unit, for said determination.

In the plaque detecting device of this embodiment, the first zero point adjustment unit performs adjustment by subtracting the component due to ambient light around the tooth surface from the first and second output values. The first and second determination units use the first and second output values which have been adjusted by the first zero point adjustment unit for determination. Therefore, the accuracy of determination can be increased.

In one embodiment, the plaque detecting device is characterized in that said first zero point adjustment unit, upon start of operation or during operation, obtains said first and second output values when said light emitting unit is turned off, and respectively subtracts said first and second output values when said light emitting unit is turned off, as said component due to ambient light, from said first and second output values when said light emitting unit is turned on.

With the plaque detecting device of this embodiment, the component due to ambient light can be suitably eliminated, making it possible to increase the accuracy of determination.

It should be noted that when this plaque detecting device is incorporated into a tooth brush, "upon start of operation or during operation" corresponds to upon start of tooth brushing or during tooth brushing.

In one embodiment, the plaque detecting device is characterized in that it comprises a signal processing unit which, in order to make said difference between said first output value and said second output value different for predetermined different types of substances which may be present on said tooth surface, computes said difference after multiplying said first output value and said second output value respectively by a first coefficient and second coefficient, which differ from each other.

In the present specification, "substances which may be present on a tooth surface" are envisioned as being enamel, resin, metal teeth, artificial teeth (ceramic or plastic), tartar and plaque. As regards "predetermined different types of substances," for example, tartar and plaque can be said to be a different type of substances in contrast to metal teeth and artificial teeth.

In the plaque detecting device of this embodiment, in order to make the difference between the first output value and the second output value different for predetermined different types of substances which may be present on the tooth surface, the signal processing unit computes said difference after multiplying the first output value and the second output value respectively by a first coefficient and second coefficient, which differ from each other. As a result, the difference between the first output value and the second output value come to differ between predetermined different types of substances which may be presented on the tooth surface. Therefore, with this plaque detecting device, it can be easily identified if a substance present on a tooth surface is plaque (or tartar) or not, based on a combination of the determination results of the first determination unit and the determination results of the second determination unit.

In one embodiment, the plaque detecting device is characterized in that said signal processing unit multiplies said first output value and said second output value respectively by said first coefficient and said second coefficient by means of amplifying said first output value and said second output value respectively by a first amplification factor and a second amplification factor, which differ from each other.

In the plaque detecting device of this embodiment, the processing of the signal processing unit is simplified.

In one embodiment, the plaque detecting device is characterized in that, in order to make said difference between said first output value and said second output value different for predetermined different types of substances which may be present on said tooth surface, the light receiving surface area of said first light receiving unit and the light receiving surface area of said second light receiving unit are set to be different from each other.

In the plaque detecting device of this embodiment, in order to make the difference between the first output value and the second output value different for predetermined different types of substances which may be present on the tooth surface, the light receiving surface area of the first light receiving unit and the light receiving surface area of the second light receiving unit are set to be different from each other. As a result, the processing of multiplying the first output value and the second output value respectively by a first coefficient and second coefficient, which differ from each other, can be omitted, and it suffices to simply take the difference between the first output value and the second output value. Therefore, the processing of the signal processing unit is simplified. As a result, the difference between the first output value and the second output value comes to be different for different types of substances which may be present on the tooth surface.

In one embodiment, the plaque detecting device is characterized in that it comprises an annunciation unit which annunciates the determination results concerning the presence or absence of plaque on said tooth surface.

Here, "annunciation" by the annunciation unit broadly includes the sounding of a buzzer, the illumination or flashing of a lamp, display by means of a display screen, etc.

In the plaque detecting device of this embodiment, an annunciation unit annunciates the determination results concerning the presence or absence of plaque on the tooth surface. Therefore, the user can easily learn if plaque is present or absent on the tooth surface.

In a different aspect, the tooth brush of this invention is characterized in that it comprises a main body including a head section having a bristled surface on which bristles are provided, a grip section intended to be gripped by a hand, and a neck section which joins said head section to said grip section, wherein a plaque detecting device as described above is incorporated into said main body.

In the tooth brush of this invention, a plaque detecting device as described above is incorporated into the main body. Therefore, the user can learn the determination results concerning the presence or absence of plaque (or tartar) while brushing teeth. As a result, it is possible to do without an optical fiber, wire, etc. extending from the tooth brush to the outside. In such a case, when a user performs tooth brushing using this tooth brush, there are no obstacles and tooth brushing can be easily carried out.

In one embodiment, the tooth brush is characterized in that said light emitting unit and said first and second light receiving units are arranged in an internal portion of said head section corresponding to a specified region of said bristled surface; said light emitting unit contains a light emitting diode which irradiates ultraviolet or blue excitation light toward said tooth surface through said specified region; said first light receiving unit contains a first optical filter member which receives said radiated light from said tooth surface through said specified region and transmits only the spectral component of said first wavelength region of said radiated light, and a first photodiode or phototransistor which receives only the spectral component of said first wavelength region which has been transmitted through the first optical filter member; and said second light receiving unit contains a second optical filter member which receives said radiated light from said tooth surface through said specified region and transmits only the spectral component of said second wavelength region of said radiated light, and a second photodiode or phototransistor which receives only the spectral component of said second wavelength region which has been transmitted through the second optical filter member.

In the tooth brush of this embodiment, the first light receiving unit and second light receiving unit can both be made with a simple configuration. Therefore, this tooth brush can be manufactured compactly and at low cost.

It will be noted that in the "specified region" of the bristled surface, it is preferable for bristles to be omitted.

In one embodiment, the tooth brush is characterized in that it comprises a second zero point adjustment unit which performs adjustment by subtracting the component due to internally reflected light in said head section from said first and second output values, wherein said first and second determination units use said first and second output values, which have been adjusted by said second zero point adjustment unit, for said determination.

In the present specification, "internally reflected light" in the head section refers to the portion of excitation light from the light emitting unit which is reflected by the constituent elements of the head section and inputted into the first and second light receiving units without reaching the tooth surface. Specifically, internally reflected light includes light reflected by the boundary surface of the specified region in the bristled surface, light reflected by the wall surfaces inside the head section (which contain the light emitting unit and the first and second light receiving units), light which has exited through the boundary surface of the specified region of the head section but was reflected by the bristles and returned, and the like. Furthermore, internally reflected light may include light which enters the first and second optical filter members directly from the light emitting unit and is then inputted into the first and second light receiving units.

With the tooth brush of this embodiment, the second zero point adjustment unit performs adjustment by subtracting the component due to internally reflected light in the head section from the first and second output values. The first and second determination units use the first and second output values, which have been adjusted by the second zero point adjustment unit, for determination. Therefore, the accuracy of determination can be increased.

In one embodiment, the tooth brush is characterized in that it comprises a light shielding member which covers said head section along with said bristles and blocks ambient light around said head section, wherein said second zero point adjustment unit, in the light shielded state in which said ambient light has been blocked by said light shielding member, with a timing inputted as an instruction through a manipulation unit or preset by means of a timer, obtains said first and second output values after turning on said light emitting unit, and also obtains said first and second output values after turning off said light emitting unit, and subsequently subtracts said first and second output values when said light emitting unit is turned off respectively from said first and second output values when said light emitting unit is turned on, to obtain the component due to said internally reflected light.

In the tooth brush of this embodiment, in the light shielded state in which the ambient light has been blocked by the light shielding member, with a timing inputted as an instruction through a manipulation unit or preset by means of a timer, the second zero point adjustment unit obtains the first and second output values after turning on the light emitting unit, and also obtains the first and second output values after turning off the light emitting unit. Subsequently, the second zero point adjustment unit subtracts the first and second output values when the light emitting unit is turned off respectively from the first and second output values when the light emitting unit is turned on, to obtain the component due to internally reflected light. Therefore, the component due to said internally reflected light can be suitably obtained in a state in which the ambient light around said head section is approximately zero.

In one embodiment, the tooth brush is characterized in that it comprises an illuminance measurement unit which measures illuminance due to ambient light around said main body, wherein said second zero point adjustment unit, using the fact that said illuminance has dropped below a predetermined illuminance threshold value as a starting condition, obtains said first and second output values after turning on said light emitting unit, and also obtains said first and second output values after turning off said light emitting unit, and subsequently subtracts said first and second output values when said light emitting unit is turned off respectively from said first and second output values when said light emitting unit is turned on, to obtain the component due to said internally reflected light.

In the tooth brush of this embodiment, the second zero point adjustment unit, using the fact that the illuminance has dropped below a predetermined illuminance threshold value as a starting condition, obtains the first and second output values after turning on the light emitting unit, and also obtains the first and second output values after turning off the light emitting unit. Subsequently, the second zero point adjustment unit subtracts the first and second output values when the light emitting unit is turned off respectively from the first and second output values when the light emitting unit is turned on, to obtain the component due to internally reflected light. Therefore, the component due to internally reflected light can be suitably obtained in a state where there is little ambient light around the head section. Furthermore, the need to install the aforementioned light shielding member on the head section does not arise. As a result, the need for the user to perform operations for acquiring calibration data can be eliminated.

In one embodiment, the tooth brush is characterized in that said illuminance measurement unit consists of one or both of said first and second light receiving units.

With the tooth brush of this embodiment, the illuminance measurement unit consists of one or both of the first and second light receiving units. Therefore, illuminance due to ambient light can be measured without increasing the number of component parts of the tooth brush.

In one embodiment, the tooth brush is characterized in that said second zero point adjustment unit, at a timing corresponding to nighttime, set in advance by means of a timer, obtains said first and second output values after turning on said light emitting unit, and also obtains said first and second output values after turning off said light emitting unit, and subsequently subtracts said first and second output values when said light emitting unit is turned off respectively from said first and second output values when said light emitting unit is turned on, to obtain the component due to said internally reflected light.

In the tooth brush of this embodiment, at a timing corresponding to nighttime, set in advance by means of a timer, the second zero point adjustment unit obtains the first and second output values after turning on the light emitting unit, and also obtains the first and second output values after turning off the light emitting unit. Subsequently, the second zero point adjustment unit subtracts the first and second output values when the light emitting unit is turned off respectively from the first and second output values when the light emitting unit is turned on, to obtain the component due to the internally reflected light. Therefore, the component due to internally reflected light can be suitably obtained in a state where there is little ambient light around the head section. As a result, the need for the user to perform operations for acquiring calibration data can be eliminated.

In yet another embodiment, the plaque detecting device has a light emitting unit which emits excitation light toward a surface of a tooth. The device receives radiated light from the first tooth surface induced by the excitation light at a first light receiving unit. The first light receiving unit extracts, from the radiated light, a first wavelength region and obtains a first output value corresponding to an intensity of the radiated light in the first wavelength region. A second light receiving unit receives radiated light from the tooth surface induced by the excitation light. The second light receiving unit extracts a second wavelength region from the radiated light and obtains a second output value corresponding to an intensity of the radiated light in the second wavelength region. A first determination unit computes a magnitude of a ratio between the first output value and the second output value as compared to a predetermined first threshold value. A second determination unit computes a magnitude of a difference between the first output value and the second output value as compared to a predetermined second threshold value.

In other implementations, a method of detecting plaque comprises providing a light emitting unit, first and second light receiving units, and first and second determination units. The light emitting unit is activated to emit excitation light toward a surface of a tooth. The first and second light receiving units receive radiated light and extract first and second wavelength regions from the radiated light. The first and second light receiving units obtain first and second output values corresponding to intensities of the first and second wavelength regions. The first determination unit computes a magnitude of a ratio between the first output value and the second output value and compares the ratio to a first threshold value. The second determination unit computes a magnitude of a difference between the first output value and the second output value as compared to a second threshold value.

Effect of the Invention

As is clear from the foregoing, with the plaque detecting device of this invention, a user is able to determine the presence or absence of plaque by means of a simple operation.

Furthermore, with the tooth brush of this invention, the user can learn the determination results concerning the presence or absence of plaque while brushing teeth.

BRIEF DESCRIPTION OF THE DRAWINGS

FIG. 1 (B) is a drawing illustrating the block configuration of the control system of this plaque detecting device.

FIG. 10 (A) is a drawing showing the ratio A between first output value $\Delta OUT1$ and second output value $\Delta OUT2$ under bandpass type settings for enamel, resin, metal teeth, artificial teeth (ceramic or plastic), tartar and plaque. FIG. 10 (B) is a drawing showing the difference B between first output value $\Delta OUT1$ and second output value $\Delta OUT2$ under bandpass type settings for enamel, resin, metal teeth, artificial teeth (ceramic or plastic), tartar and plaque.

FIG. 12 (A) is a drawing showing the ratio A' between first output value $\Delta OUT1$ and second output value $\Delta OUT2$ under high-pass type settings for enamel, resin, metal teeth, artificial teeth (ceramic or plastic), tartar and plaque. FIG. 12 (B) is a drawing showing the difference B' between second output value $\Delta OUT2$ and first output value $\Delta OUT1$ under high-pass type settings for enamel, resin, metal teeth, artificial teeth (ceramic or plastic), tartar and plaque.

FIG. 13 (A) and FIG. 13 (B) are drawings illustrating the process of determination of the presence or absence of plaque or tartar based on ratio A' and difference B'.

FIG. 15 (B) is a drawing showing an enlargement of the head section during tooth brushing.

FIG. 28 (B) is a drawing showing the difference B' between second output value $\Delta OUT2$ and first output value $\Delta OUT1$ for enamel, metal teeth, artificial teeth (ceramic), tartar (and plaque), and plaque, when no countermeasures have been taken against internally reflected light of the head section.

FIG. 30 (B) and FIG. 30 (C) are drawings illustrating the procedure of covering the head section with the light shielding member.

FIG. 31 (B) is a drawing showing the difference B' between second output value $\Delta OUT2$ and first output value $\Delta OUT1$ for enamel, metal teeth, artificial teeth (ceramic), tartar (and plaque), and plaque, when countermeasures have been taken against internally reflected light of the head section.

FIG. 32 (B) is a drawing showing the difference B" between second output value $\Delta OUT2$ and first output value $\Delta OUT1$ for enamel, metal teeth, artificial teeth (ceramic), tartar (and plaque), and plaque, when countermeasures have been taken against internally reflected light of the head section and the first output value ΔOUT1 and second output value ΔOUT2 have been multiplied respectively by a first coefficient and second coefficient, which differ from each other.

FIG. 37 (B) is a drawing in which a line representing a second threshold value β" has been added to FIG. 32 (B).

FIG. 39 (B) is a drawing showing a further modified example of aforementioned modified example 1.

FIG. 42 (B) is a drawing showing a further modified example of aforementioned modified example 2.

FIG. 45 (B) is a drawing showing a further modified example of aforementioned modified example 3.

MODES FOR EMBODYING THE INVENTION

Modes of embodiment of this invention will be described in detail below with reference to the drawings.

First Embodiment (Configuration)

Figure 1A:
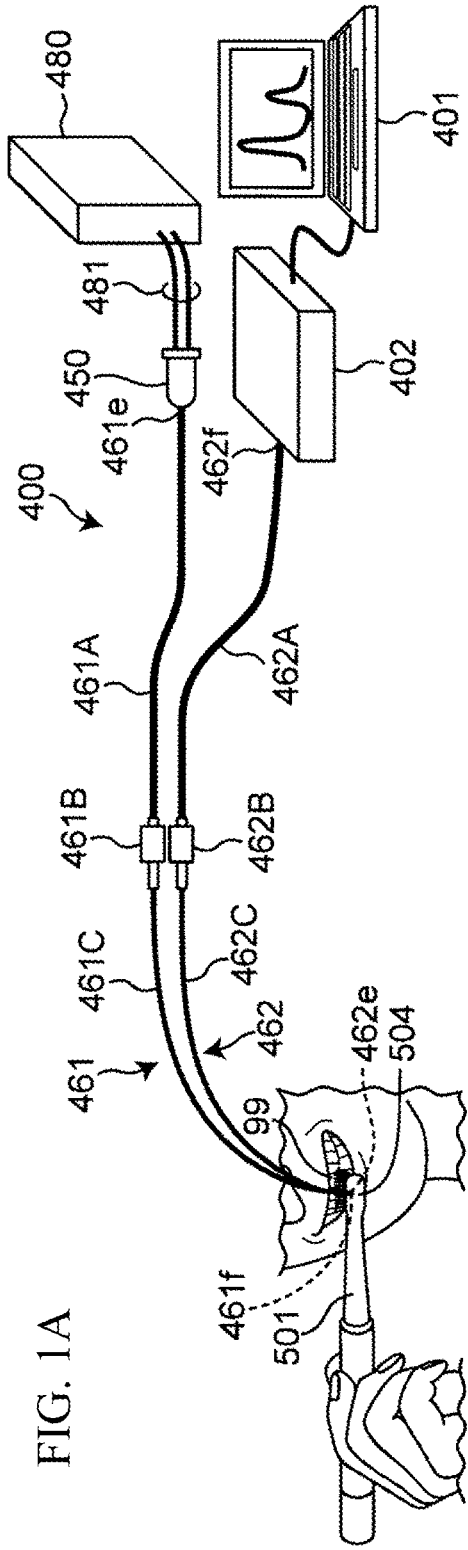
FIG. 1 (A) is a drawing schematically illustrating the simplified configuration of a plaque detecting device of one embodiment of this invention.
Figure 1B:
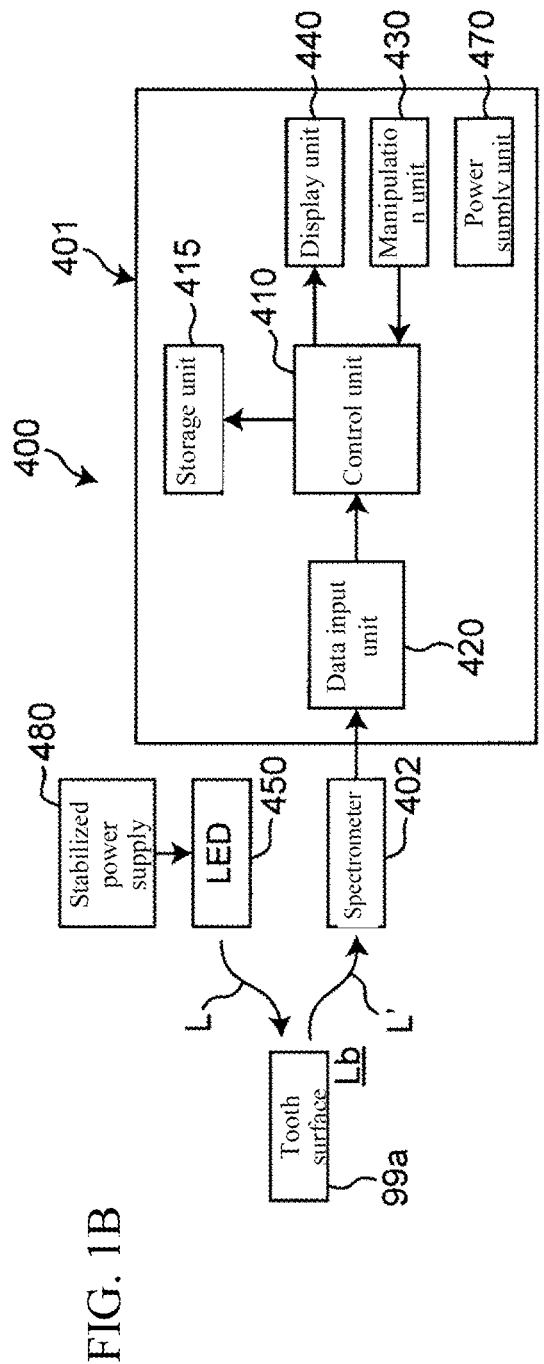

FIG. 1 (A) schematically illustrates the simplified configuration of a plaque detecting device (represented as a whole by reference symbol 400) of one embodiment of this invention. Furthermore, FIG. 1 (B) illustrates the block configuration of the control system of plaque detecting device 400.

As shown in FIG. 1 (A), this plaque detecting device 400 comprises a stabilized power supply 480, an LED (light emitting diode) 450 as the light emitting unit, a forward waveguide 461, a tooth brush 501, a return waveguide 462, a spectrometer 402 and a data analysis computer 401.

The stabilized power supply 480, in order to cause the LED 450 to emit light, supplies direct current to LED 450 through wire 481, in this example, with a voltage of 4.8 V to 5.0 V, at about 10 mA to 15 mA.

The LED 450 receives the supply of direct current from the stabilized power supply 480 and emits light having a peak wavelength corresponding to ultraviolet or blue (which becomes the excitation light L shown in FIG. 1 (B)). In this example, the LED 450 is a DIP type ultraviolet LED (model number UV3TZ-405-15) made by Bivar, Inc., and emits light L having a peak wavelength of 405 nm.

Forward waveguide 461 comprises a fiber cable 461A, plastic optical fiber 461C, and a feed-through connector 461B which optically links the fiber cable 461A and the plastic optical fiber 461C. The entry side end 461e of the fiber cable 461A is arranged facing the light radiating surface of the LED 450. Light taken in through the end 461e of the fiber cable 461A passes through the fiber cable 461A, feed-through connector 461B and plastic optical fiber 461C, and reaches the exit side end 461f of the plastic optical fiber 461C. The end 461f of plastic optical fiber 461C penetrates through the head section 504 of the tooth brush 501 and is arranged so as to face the surface 99a of the subject's teeth 99. Therefore, light emitted by the LED 450 is irradiated as excitation light onto the tooth surface 99a, as shown in FIG. 1 (B).

The return waveguide 462 shown in FIG. 1 (A) comprises a fiber cable 462A, plastic optical fiber 462C, and a feed-through connector 462B which optically links the fiber cable 462A and plastic optical fiber 462C. The entry side end 462e of plastic optical fiber 462C penetrates through the head section 504 of the tooth brush 501 alongside the end 461f of plastic optical fiber 461C and is arranged opposite the surface of the teeth 99. Light taken in through the end 462e of the plastic optical fiber 462C (radiated light L' generated by the tooth surface 99a due to excitation light L shown in FIG. 1 (B)) passes through plastic optical fiber 462C, feed-through connector 462B and fiber cable 462A, reaches the exit side end 462f of fiber cable 462A, and is inputted into spectrometer 402.

In this example, a fiber patch cable made by Thorlabs Japan, Inc. (step index multimode, core diameter 1,000 μm, numerical aperture NA 0.48, connector SMA-SMA, length 1 m) was used for the fiber cables 461A, 462A. Furthermore, plastic optical fiber cable 1,000 UM (outside diameter 2.2 mm) made by Edmund Optics Japan, Ltd. was used for the plastic optical fiber 461C, 462C. By using relatively light weight plastic optical fiber 461C, 462C for the tooth brush 501 side portion of the forward waveguide 461 and return waveguide 462, it is possible to avoid the tooth brush 501 being felt to be heavy.

The spectrometer 402 in this example consists of the SEC 2000 Spectrometer made by ALS Co., and outputs a signal representing the intensity per wavelength of inputted light (radiated light L'). The resolution in the vicinity of wavelength 600 nm to 700 nm is approximately 0.4 nm.

The data analysis computer 401, as shown in FIG. 1 (B), comprises a control unit 410, storage unit 415, data input unit 420, manipulation unit 430, display unit 440 and power supply unit 470.

The control unit 410 includes a CPU (central processing unit) operated by software, and executes the various types of processing described below.

The data input unit 420 comprises a known input interface, inputs the output of spectrometer 402, that is, a signals representing the intensity for each wavelength of light (radiated light L') inputted into the spectrometer 402, and passes them to the control unit 410.

The manipulation unit 430 includes a known keyboard and mouse and works for inputting commands and various information from the user. Commands include a command instructing the start of processing, a command instructing the recording of computation results, etc. Inputted information includes information (identification number) for identifying the subject, and the like.

The storage unit 415 includes a hard disk drive or EEPROM (electrically rewritable non-volatile memory) capable of non-temporary storage of data. The storage unit 415 stores a control program for controlling the control unit 410. Furthermore, the storage unit 415 stores signals representing the intensity of each wavelength of radiated light L' inputted from the spectrometer 402 via the data input unit 420.

The display unit 440, in this example, comprises an LCD (liquid crystal display element), and displays various types of information, such as computation results produced by the control unit 410.

The power supply unit 470 supplies power to the various units in the computer 401.

(Operation)

Figure 2:
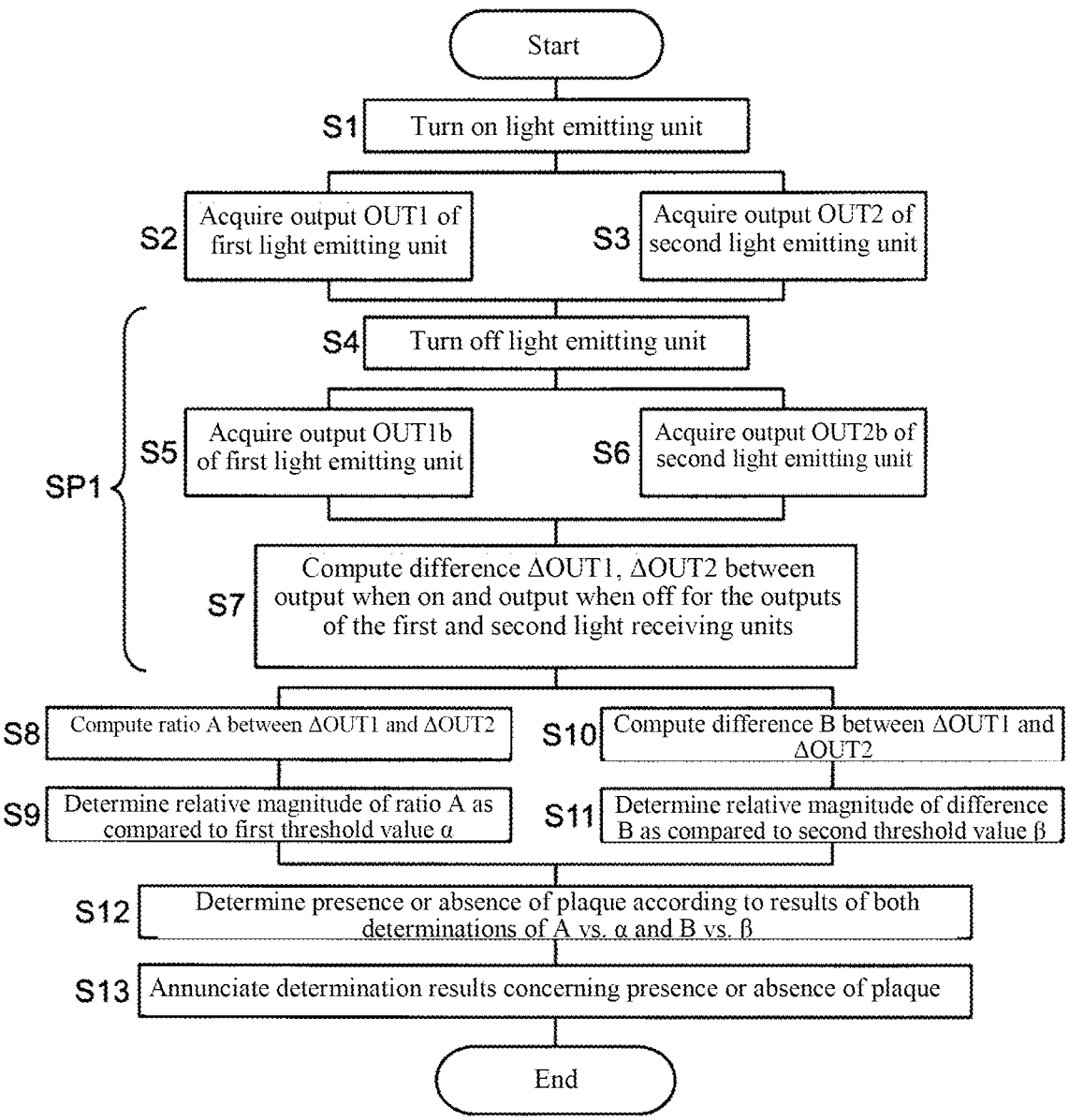
FIG. 2 is a drawing illustrating the process flow performed by said plaque detecting device.

This plaque detecting device 400 operates according to the processing flow shown as a whole in FIG. 2, based on manipulations by the user (referring to the person manipulating the device 400). It will be noted that the user may be either the same person as the subject or a different person.

(1) First, in a state where the user has arranged the end 461$f$ of the forward waveguide 461 and the end 462$e$ of the return waveguide 462 opposite the surface 99$a$ of the subject's teeth 99, as shown in step S1 in FIG. 2, direct current is supplied from stabilized power supply 480, turning on the LED 450 as the light emitting unit. Thereupon, as shown in FIG. 1 (B), light emitted by the LED 450 (peak wavelength 405 nm) is irradiated as excitation light L onto the tooth surface 99$a$, in response to which, radiated light L' is radiated from the tooth surface 99$a$. This radiated light L' is inputted into the spectrometer 402 together with ambient light Lb around the tooth surface 99$a$, described later.

Figure 3:
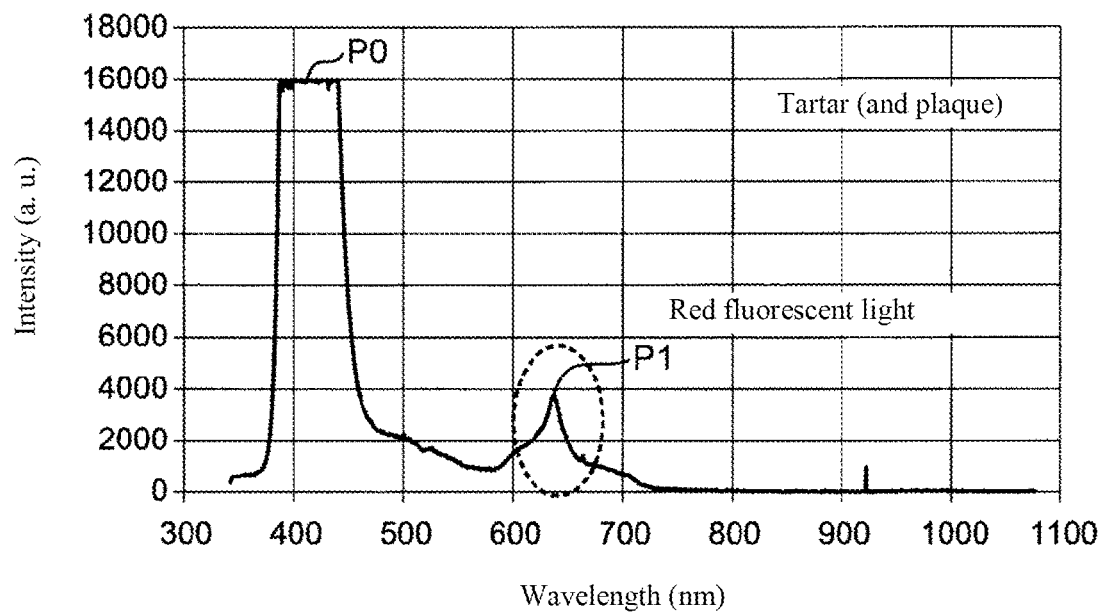
FIG. 3 is a drawing illustrating the spectrum of fluorescent light specific to tartar.
Figure 4:
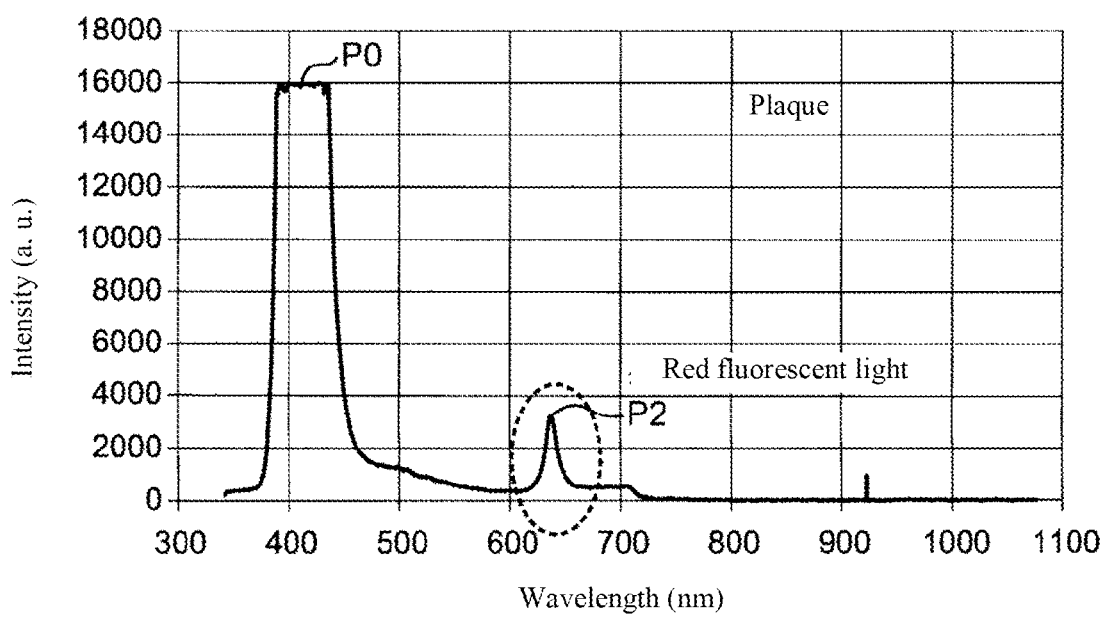
FIG. 4 is a drawing illustrating the spectrum of fluorescent light specific to plaque.

This radiated light L' has a wavelength spectrum corresponding to the substance irradiated by the excitation light L. Generally speaking, tooth enamel, resin, metal teeth, artificial teeth (ceramic or plastic), tartar and plaque may be present on the tooth surface. If the substance irradiated by excitation light L is, for example, tartar, as shown in FIG. 3, the radiated light L', in addition to the peak PO generated due to scattering of excitation light L, contains the peak wavelength P1 (≈630 nm, red) of fluorescent light specific to tartar. Similarly, if the substance irradiated by excitation light L is, for example, plaque, as shown in FIG. 4, the radiated light L' contains, in addition to the peak PO generated due to scattering of excitation light L, the peak wavelength P2 (≈630 nm, red) of fluorescent light specific to plaque. The spectral component of these peaks is distributed over a range of approximately ±10 nm from the peak wavelength. It will be noted that tartar is plaque which has gradually changed and become deposited on the tooth surface, and thus it is difficult to complete distinguish the two substances. The designation "tartar (and plaque)" is used in FIG. 3 for this reason (the same applies to FIG. 11 through FIG. 14, described below).

Figure 5:
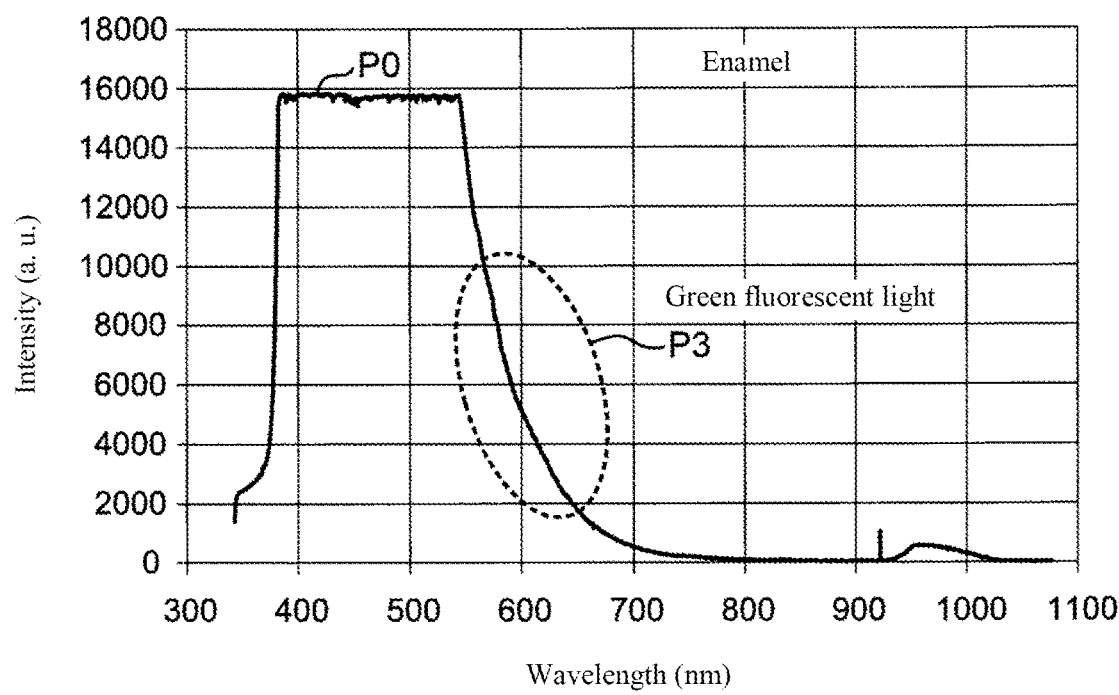
FIG. 5 is a drawing illustrating the spectrum of fluorescent light specific to enamel.

If the substance irradiated by excitation light L is tooth enamel, as shown in FIG. 5, the radiated light L', in addition to the peak PO generated due to scattering of excitation light L, contains the spectral component P3 (green) of fluorescent light specific to enamel. More specifically, in FIG. 5, the peak wavelength of fluorescent light specific to enamel is approximately 480 nm, although it is hidden by the peak PO generated due to scattering of excitation light L. The spectral component to the longer wavelength side of that peak is distributed broadly from the peak wavelength to about 750 nm.

Figure 6:
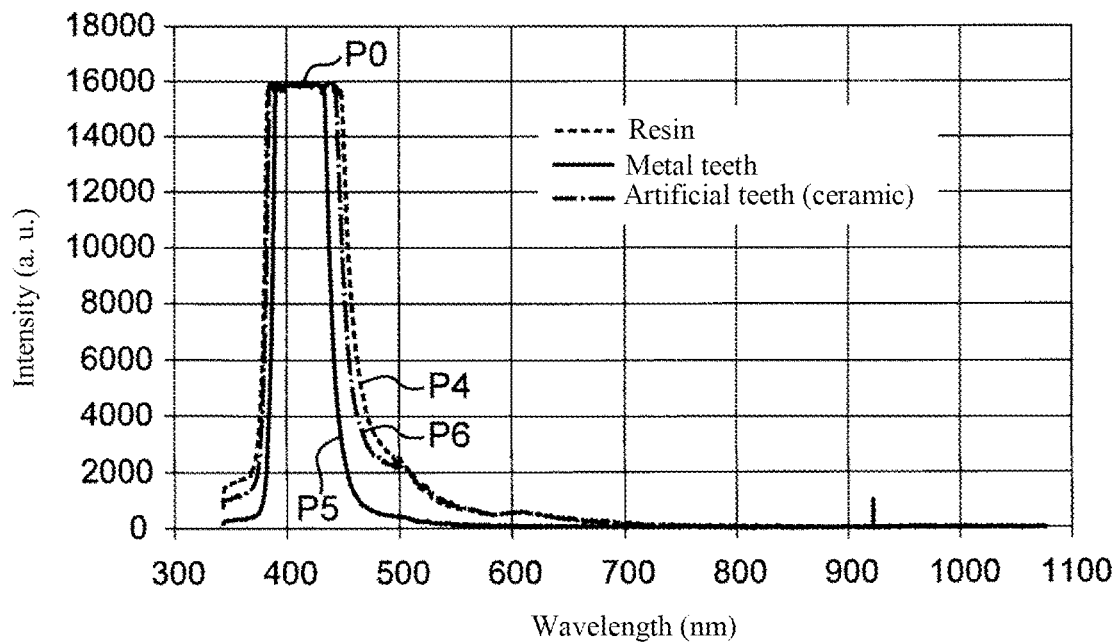
FIG. 6 is a drawing illustrating the spectrum of radiated light from resin, metal teeth and artificial teeth (ceramic).

Furthermore, if the substance irradiated with excitation light L is resin and artificial teeth (ceramic), as shown in FIG. 6, the radiated light L', in addition to the peak PO generated due to scattering of excitation light L, contains the spectral components P4, P6 of the respective specific fluorescent light. On the other hand, if the substance irradiated with excitation light L is metal teeth, the radiated light L' contains only the peak PO generated due to reflection or scattering of excitation light L and its tail P5.

The spectrometer 402 in FIG. 1 (B) outputs a signal representing the intensity of each wavelength of radiated light L'. This signal is inputted into control unit 410 via data input unit 420. In this example, the control unit 410, acting along with the spectrometer 402 as the first light receiving unit, as shown in step S2 in FIG. 2, extracts the spectral component of a predetermined first wavelength region from the radiated light L', and acquires a first output value OUT1 corresponding to the intensity of the spectral component of this first wavelength region. Furthermore, the control unit 410, acting along with the spectrometer 402 as the second light receiving unit, as shown in step S3, extracts the spectral component of a predetermined second wavelength region from the radiated light L', and acquires a second output value OUT2 corresponding to the intensity of the spectral component of this second wavelength region. It will be noted that the first output value OUT1 and second output value OUT2 correspond to a magnitude obtained by integrating (or summing) the spectral component of the respective wavelength region over that wavelength region (the same applies to the first output value OUT1$b$ and second output value OUT2$b$, described later).

Here, the first wavelength region, in this example, is defined as the wavelength region from a lower limit wavelength of 620 nm to an upper limited wavelength of 750 nm. As can be seen from FIG. 3 and FIG. 4, the lower limit wavelength 620 nm of the first wavelength region is defined as a wavelength just below the peak wavelength of approximately 630 nm specific to plaque (and tartar). The upper limit wavelength 750 nm of the first wavelength region is defined as the wavelength at which the tail on the longer wavelength side of the peak specific to plaque (and tartar) goes substantially to zero. As a result, the first wavelength region includes substantially the entire region of the wavelength range of fluorescent light specific to plaque.

Furthermore, the second wavelength region, in this example, is defined as the wavelength region from a lower limit wavelength of 550 nm to an upper limit wavelength of 600 nm. As can be seen from FIG. 5, the lower limit wavelength 550 nm of the second wavelength region is defined as a wavelength which exceeds the peak wavelength of approximately 480 of fluorescent light specific to enamel and is below the lower limit wavelength 620 nm of the first wavelength region. The upper limit wavelength 600 nm of the second wavelength region, in this example, is defined so that the second wavelength region does not overlap the first wavelength region. As a result, the second wavelength region does not include the wavelength range of fluorescent light specific to plaque (and tartar), and includes the wavelength range of fluorescent light specific to enamel (a portion to the longer wavelength side from the peak wavelength). Moreover, as can be seen from FIG. 6, this second wavelength region also includes the wavelength range of fluorescent light specific to resin and artificial teeth (ceramic) (a portion to the longer wavelength side from the peak wavelength) and the tail of scattered light from metal teeth.

(2) Next, the user causes the control unit 410 to perform the first zero point adjustment processing SP1 shown in FIG. 2.

Figure 7:
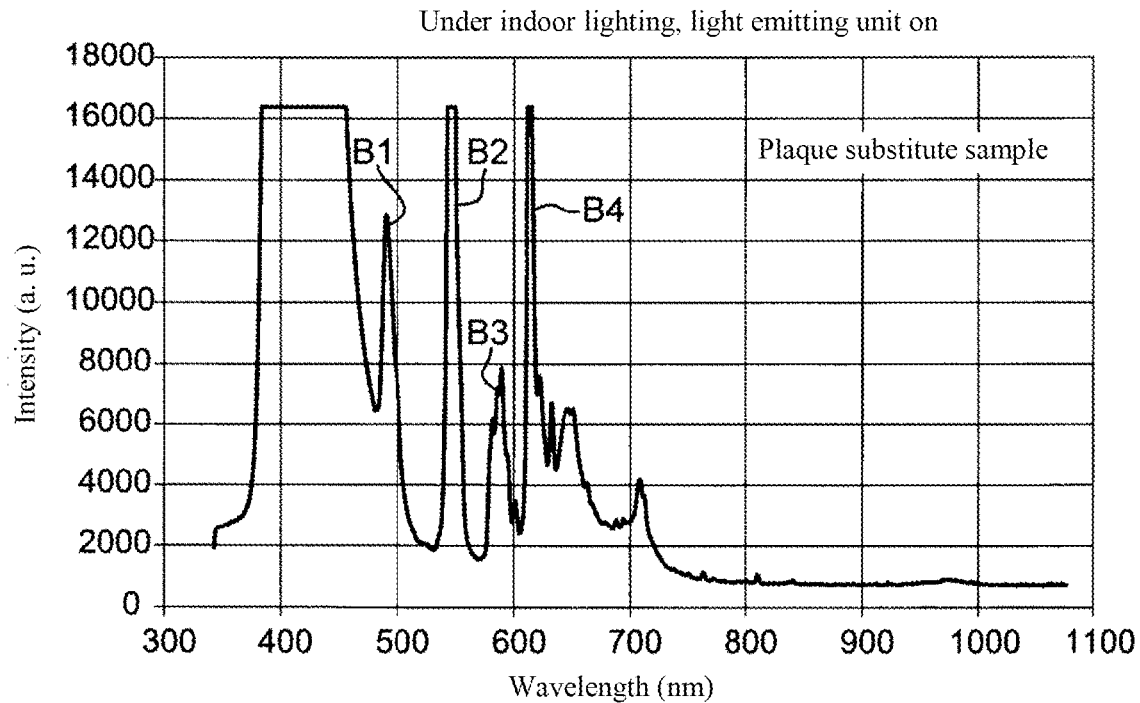
FIG. 7 is a drawing illustrating spectroscope output when the light emitting unit is turned on under indoor lighting on a plaque substitute sample.
Figure 8:
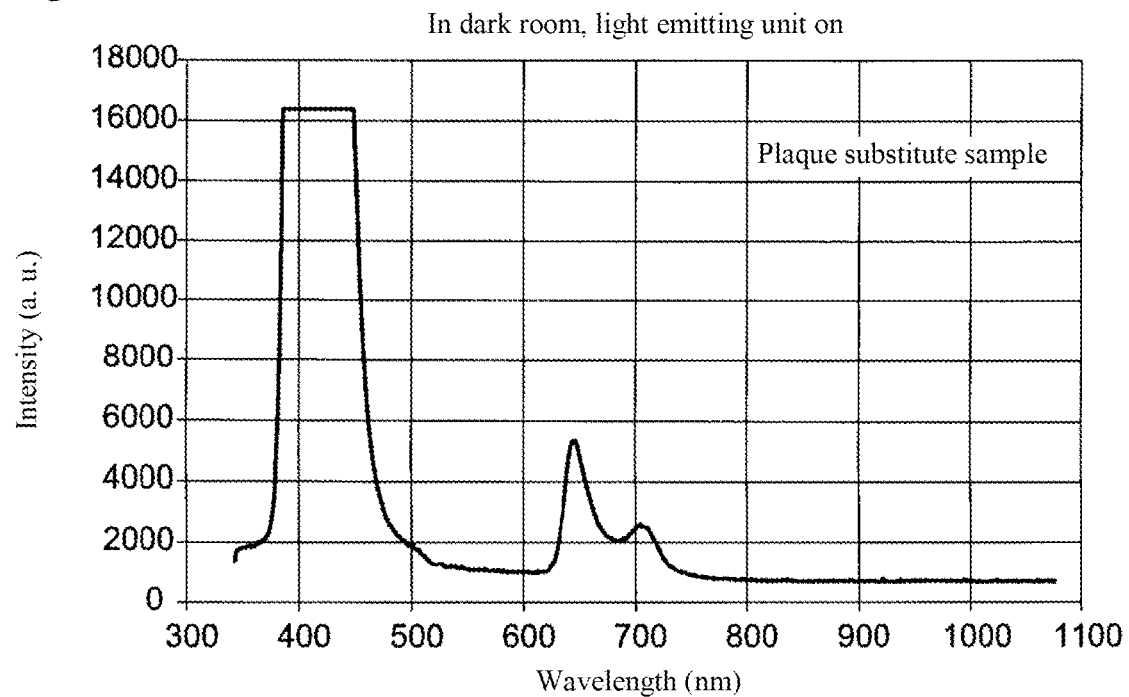
FIG. 8 is a drawing illustrating spectrometer output when the light emitting unit is turned on in a dark room on a plaque substitute sample.
Figure 9C:
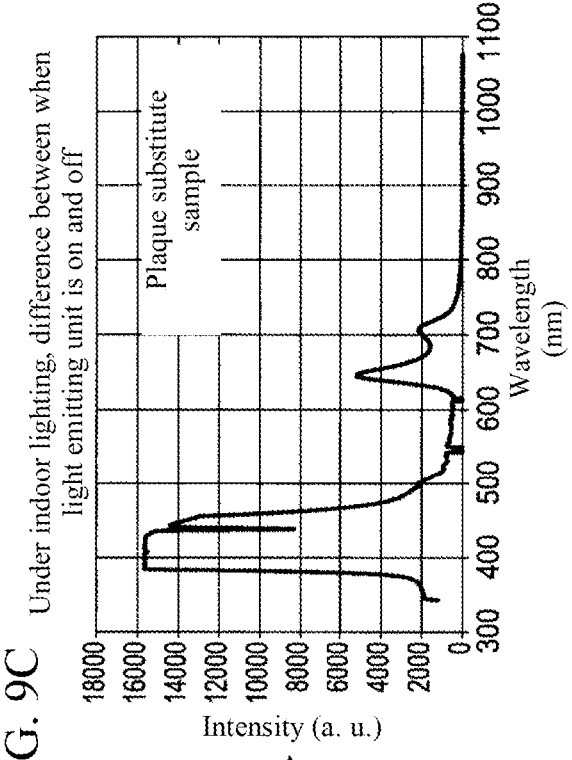
FIG. 9 is a drawing showing an example of data obtained through first zero point adjustment processing.
Figure 9A:
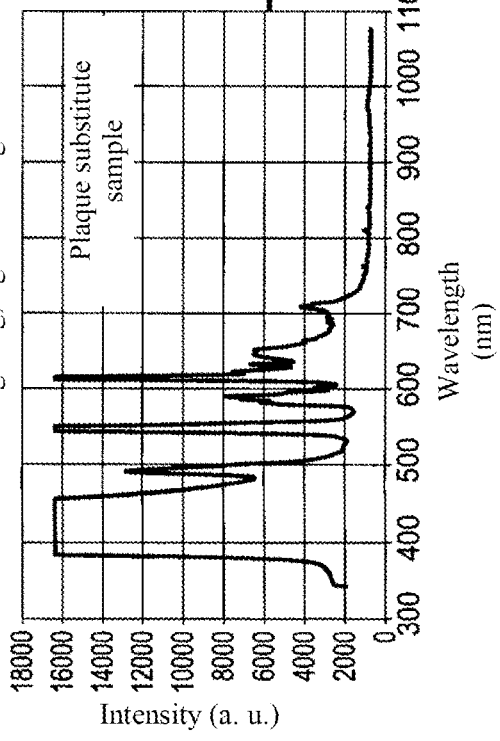
Figure 9B:
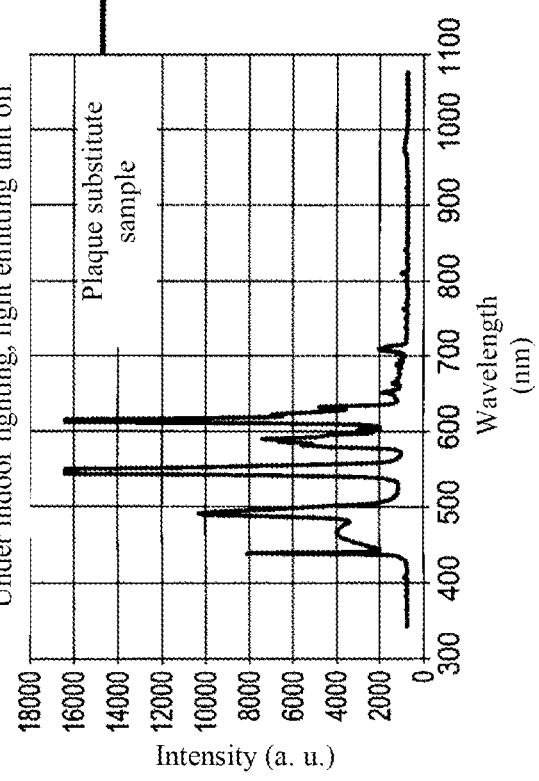

Here, the first zero point adjustment processing SP1 has been introduced by the inventors in consideration of the fact that, for example, with a plaque substitute sample (porphyrin solution), when one compares the spectrometer output when the light emitting unit (LED 450) is turned on under indoor lighting (the spectral component shown in FIG. 7) to spectrometer output when the light emitting unit (LED 450) is turned on in a dark room (the spectral component shown in FIG. 8), under indoor lighting (FIG. 7), components B1 through B4, which are due to ambient light Lb around the tooth surface 99a, are present as external interference. Namely, with the aforementioned plaque substitute sample (porphyrin solution), under the same indoor lighting, the components due to ambient light Lb around the tooth surface 99a can be eliminated, as shown in FIG. 9 (C), by subtracting the spectrometer output when the light emitting unit (LED 450) is turned off (the spectral component shown in FIG. 9 (B)) for each wavelength from the spectrometer output when the light emitting unit (LED 450) is turned on (the spectral component shown in FIG. 9 (A)).

Specifically, the user, as shown in step S4 of FIG. 2, stops direct current from the stabilized power supply 480 to turn off the LED 450 as the light emitting unit. Thereupon, only the ambient light Lb around the tooth surface 99a shown in FIG. 1 (B) is inputted into the spectrometer 402.

Here, the spectrometer 402 in FIG. 1 (B) outputs a signal representing the intensity for each wavelength of ambient light Lb. This signal is inputted via the data input unit 420 into the control unit 410. In this example, the control unit 410, acting together with the spectrometer 402 as the first light receiving unit, as shown in step S5 of FIG. 2, extracts the spectral component of the first wavelength region of the ambient light Lb, and acquires a first output value OUT1$b$ corresponding to the intensity of the spectral component of this first wavelength region. Furthermore, the control unit 410, acting together with the spectrometer 402 as the second light receiving unit, as shown in step S6 of FIG. 2, extracts the spectral component of the second wavelength region of the ambient light Lb, and acquires a second output value OUT2$b$ corresponding to the intensity of the spectral component of this second wavelength region. It will be noted that the acquisition of the component due to ambient light Lb (that is, the first output value OUT1$b$ and second output value OUT2$b$) may be carried out either at start of operation or during operation.

Next, the control unit 410, acting as the first zero point adjustment unit, as shown in step S7 of FIG. 2, performs adjustment by subtracting the component due to ambient light Lb around the tooth surface 99a (i.e. OUT1$b$, OUT2$b$) from the aforementioned first output value OUT1 and second output value OUT2. Specifically, the differences $$\Delta\text{OUT1} = \text{OUT1} - \text{OUT1}b$$

$$\Delta\text{OUT2} = \text{OUT2} - \text{OUT2}b$$

are computed as the adjusted first output value ΔOUT1 and second output value ΔOUT2. It will be noted that the processing of steps S4 through S7 in FIG. 2 is referred to together as the first zero point adjustment processing SP1. Performing this first zero point adjustment processing SP1 makes it possible to suitably eliminate the effect of the component due to ambient light Lb and increase the accuracy of determination of the presence or absence of plaque, as described below.

(3) Next, the control unit 410, as shown in step S8 of FIG. 2, computes the ratio A between the above-described adjusted first output value ΔOUT1 and second output value ΔOUT2. Specifically, in this example, $$A = \Delta\text{OUT1}/\Delta\text{OUT2} \qquad \text{(Formula 1)}$$

is computed. Moreover, the control unit 410, acting as the first determination unit, as shown in step S9 of FIG. 2, performs determination of the relative magnitude of this ratio A as compared to a predetermined first threshold value α. According to the results of this determination, the substance which may be present on the tooth surface (namely, enamel, resin, metal teeth, artificial teeth (ceramic or plastic), tartar and plaque) can be identified as belonging either to the group consisting of enamel, resin and artificial teeth (ceramic or plastic), or the group consisting of metal teeth, tartar and plaque. As stated already, it is difficult to completely distinguish tartar and plaque as substances, so when simply "tartar" is mentioned, strictly speaking, "tartar (and plaque)" is indicated.

More specifically, the ratio A between the first output value ΔOUT1 and the second output value ΔOUT2 for enamel, resin, metal teeth, artificial teeth (ceramic or plastic), tartar and plaque is as indicated by the bar graph shown in FIG. 10 (A). In FIG. 10 (A), the horizontally arrayed bars correspond to samples of enamel, resin, metal teeth, artificial teeth (ceramic or plastic), tartar and plaque. In this example, the total number of samples was 98. The vertical axis of FIG. 10 (A) represents ratio A as a dimensionless quantity. As can be seen from FIG. 10 (A), for the group consisting of enamel, resin and artificial teeth (ceramic or plastic), the ratio A is generally smaller than 0.5. On the other hand, for the group consisting of metal teeth, tartar and plaque, the ratio A is generally greater than 0.5. Therefore, defining a first threshold value α=0.5 in advance makes it possible to distinguish the group consisting of enamel, resin and artificial teeth (ceramic or plastic) from the group consisting of metal teeth, tartar and plaque.

(4) Furthermore, the control unit 410, as shown step S10 of FIG. 2, computes the difference B between the above-described amended first output value ΔOUT1 and second output value ΔOUT2. Specifically, in this example, $$B = \Delta\text{OUT1} - \Delta\text{OUT2} \qquad \text{(Formula 2)}$$

is computed. Moreover, the control unit 410, acting as the second determination unit, as shown in step S11 of FIG. 2, performs determination of the relative magnitude of this difference B as compared to a predetermined second threshold value β. According to the results of this determination, the substance which may be present on the tooth surface (namely, enamel, resin, metal teeth, artificial teeth (ceramic or plastic), tartar and plaque) can be identified as belonging either to the group consisting of enamel, resin, metal teeth and artificial teeth (ceramic or plastic) or the group consisting of tartar and plaque.

More specifically, the difference B between the first output value ΔOUT1 and the second output value ΔOUT2 for enamel, resin, metal teeth, artificial teeth (ceramic or plastic), tartar and plaque is as indicated by the bar graph shown in FIG. 10 (B). In FIG. 10 (B), the horizontally arrayed bars correspond to samples of enamel, resin, metal teeth, artificial teeth (ceramic or plastic), tartar and plaque. The vertical axis of FIG. 10 (B) represents difference B in arbitrary units (a. u.). As can be seen from FIG. 10 (B), for the group consisting of enamel, resin and metal teeth and artificial teeth (ceramic or plastic), the difference B is generally smaller than 10,000 (a. u.). On the other hand, for the group consisting of tartar and plaque, the difference B is generally greater than 10,000 (a. u.). Therefore, defining a second threshold value β=10,000 (a. u.) in advance makes it possible to distinguish the group consisting of enamel, resin, metal teeth and artificial teeth (ceramic or plastic) from the group consisting of tartar and plaque.

It will be noted that the determination of the relative magnitude of the ratio A as compared to the first threshold value α under (3) above and the determination of the relative magnitude of the difference B as compared to the second threshold value β under (4) above can be carried out either one after the other or in parallel.

(5) Next, the control unit 410, as shown in step S12 of FIG. 2, based on a combination of the determination results of the relative magnitude of the ratio A as compared to the first threshold value α under (3) above and the determination results of the relative magnitude of the difference B as compared to the second threshold value β under (4) above, determines if the substance present on the tooth surface 99a is plaque (or tartar) or not.

Figure 11A:
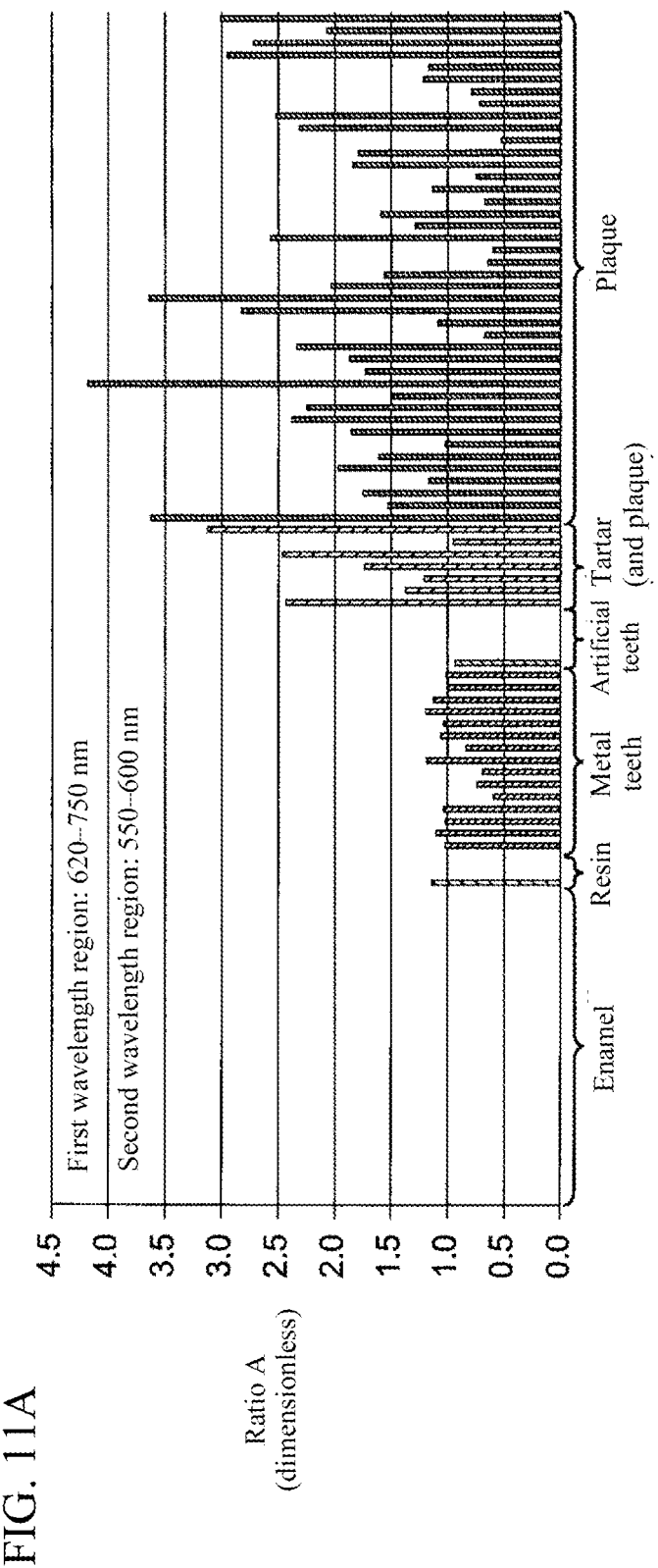
FIG. 11 (A) and FIG. 11 (B) are drawings illustrating the process of determination of the presence or absence of plaque or tartar based on ratio A and difference B.
Figure 11B:
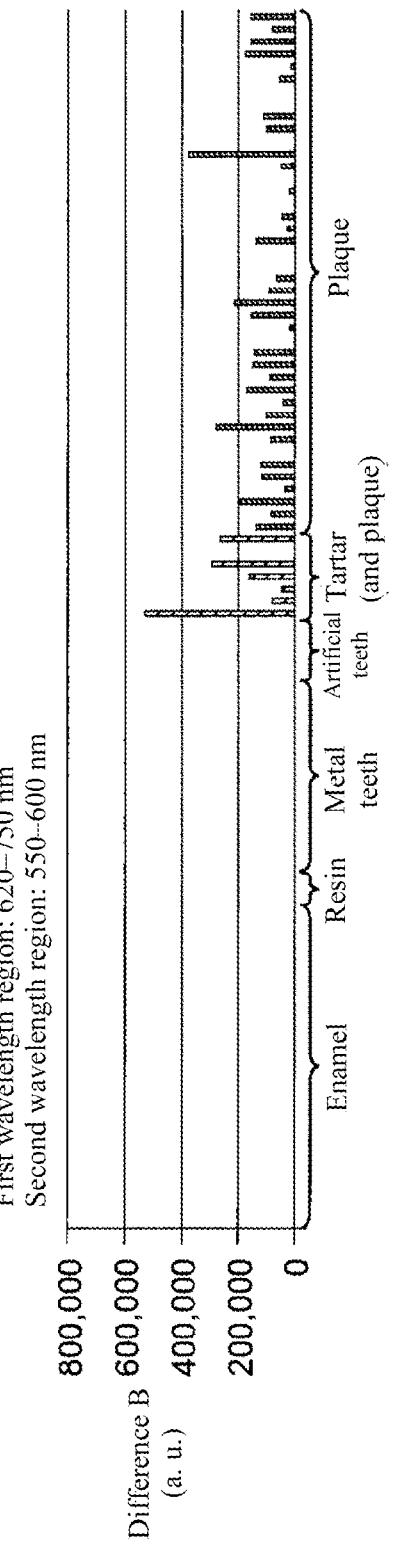

Specifically, in the case where the substance present of the tooth surface 99a is plaque (or tartar), for example, first, through the determination according to (3) above, as shown in FIG. 11 (A), the substance present on the tooth surface 99a is identified as being a substance belonging to the group consisting of metal teeth, tartar and plaque. Next, through the determination according to (4) above, as shown in FIG. 11 (B), that substance is identified as being not metal teeth but rather plaque (or tartar). In this example, the plaque-tartar determination rate (the proportion of samples correctly determined to be plaque or tartar from among 50 samples of plaque or tartar) was (plaque-tartar determination rate)=39 samples/50 samples=79(%). Furthermore, the false determination rate (the proportion of samples incorrectly determined to be plaque or tartar out of 48 samples of enamel, resin, metal teeth and artificial teeth (ceramic or plastic)) was (false determination rate)=0 samples/48 samples=0%. In this way, determination was successfully performed with good accuracy.

Conversely, in the case where the substance present on the tooth surface 99a is plaque (or tartar), if the determination according to (4) above is to be performed before the determination according to (3) above, first, through the determination according to (4) above, the substance present on the tooth surface is immediately identified as being a substance belonging to the group consisting of tartar and plaque rather than the group consisting of enamel, resin, metal teeth and artificial teeth (ceramic or plastic). In this case, the determination according to (3) above becomes unnecessary.

Here, with this plaque detecting device 400, unlike the device described in patent document 1, the user does not need to find a "tooth surface without biological deposits" to serve as a basis for comparison, and there is also no need for the calibration-type operation of saving a reference. Therefore, the user can obtain determination results concerning the presence or absence of plaque (or tartar) through a simple operation, for example, by simply arranging the light emitting unit and light receiving unit (including the forward waveguide 461 and return waveguide 462) opposite the tooth surface 99a and instructing (switching on) the start of operation of the plaque detecting device 400.

(6) Subsequently, the control unit 410, acting as an annunciation unit, in this example, displays the determination results concerning the presence or absence of plaque (or tartar) on the display screen of display unit 440, which comprises an LCD. Therefore, the user is able to easily find out if plaque (or tartar) is present on the tooth surface.

It will be noted that, instead of display using a display screen, or in addition thereto, the presence or absence of plaque (or tartar) may also be annunciated by sounding a buzzer or by turning on or flashing a lamp.

Modified Example

In the above example, the first wavelength region, from a lower limit wavelength of 620 nm to an upper limit wavelength of 750 nm, and the second wavelength region, from a lower limit wavelength of 550 nm to an upper limit wavelength of 600 nm, were both defined to be of the bandpass type, but the invention is not limited thereto. It is also possible to define only the lower limit wavelength for the first wavelength region and second wavelength region while leaving the upper limit wavelength undefined (no upper limit), in other words, to define regions of the highpass type.

FIG. 12 (A) illustrates, in correspondence with FIG. 10 (A), the ratio A' between the first output value ΔOUT1 and second output value ΔOUT2 obtained in step S8 of FIG. 2 in the case where the first wavelength region and second wavelength region were defined as having lower limit wavelengths of 620 nm and 550 nm respectively, with an undefined upper limit wavelength (no upper limit). It will be noted that in this example, the ratio A' is defined as $$A' = \Delta OUT1/\Delta OUT2 \quad \text{(Formula 3)}$$

similarly to the preceding example. As can be seen from FIG. 12 (A), for the group consisting of enamel, resin and artificial teeth (ceramic or plastic), the ratio A' is generally less than 0.35. On the other hand, for the group consisting of metal teeth, tartar and plaque, the ratio A' is generally greater than 0.35. Therefore, setting the first threshold value α'=0.35 in advance makes it possible to distinguish the group consisting of enamel, resin and artificial teeth (ceramic or plastic) from the group consisting of metal teeth, tartar and plaque.

Similarly, FIG. 12 (B) illustrates, in correspondence with FIG. 10 (B), the difference B' between the first output value ΔOUT1 and second output value ΔOUT2 obtained in step S10 of FIG. 2 in the case where a lower limit wavelength of 620 nm and 550 nm has been defined for the first wavelength region and second wavelength region respectively, with the upper limit wavelength being undefined (no upper limit). It will be noted that in this example, for the difference B', the minuend and subtrahend have been reversed relative to the previous example, as follows:

$$B' = \Delta OUT2 - \Delta OUT1 \quad \text{(Formula 4)}$$

As can be seen from FIG. 12 (B), for the group consisting of metal teeth, the difference B' is generally less than 100,000 (a. u.). On the other hand, for the group consisting of enamel, resin, artificial teeth (ceramic or plastic), tartar and plaque, the difference B' is generally greater than 100,000 (a. u.). Therefore, defining a second threshold value $\beta'=100,000$ (a. u.) in advance makes it possible to distinguish the group consisting of metal teeth from the group consisting of enamel, resin, artificial teeth (ceramic or plastic), tartar and plaque.

Therefore, in step S12 of FIG. 2, based on a combination of the determination results of the relative magnitude of the ratio A' as compared to the first threshold value $\alpha'$ in FIG. 12 (A) and the determination results of the relative magnitude of the difference B' as compared to the second threshold value $\beta'$ in FIG. 12 (B), it can be determined if the substance present on the tooth surface 99a is plaque (or tartar) or not.

Specifically, in the case where the substance present of the tooth surface 99a is plaque (or tartar), for example, first, through the determination according to FIG. 12 (A), as shown in FIG. 13 (A), the substance present on the tooth surface 99a is identified as being a substance belonging to the group consisting of metal teeth, tartar and plaque. Next, through the determination according to FIG. 12 (B), as shown in FIG. 13 (B), that substance is identified as being not metal teeth but rather plaque (or tartar). In this example, the plaque-tartar determination rate (the proportion of samples correctly determined to be plaque or tartar from among 50 samples of plaque or tartar) was (plaque-tartar determination rate)=44 samples/50 samples=88(%). Furthermore, the false determination rate (the proportion of samples incorrectly determined to be plaque or tartar out of 48 samples of enamel, resin, metal teeth or artificial teeth (ceramic or plastic)) was (false determination rate)=3 samples/48 samples=6(%). In this way, determination was successfully performed with good accuracy also when the first wavelength region and second wavelength region were of the high-pass type, just as in the case of bandpass type.

Second Embodiment (Configuration)

Figure 14B:
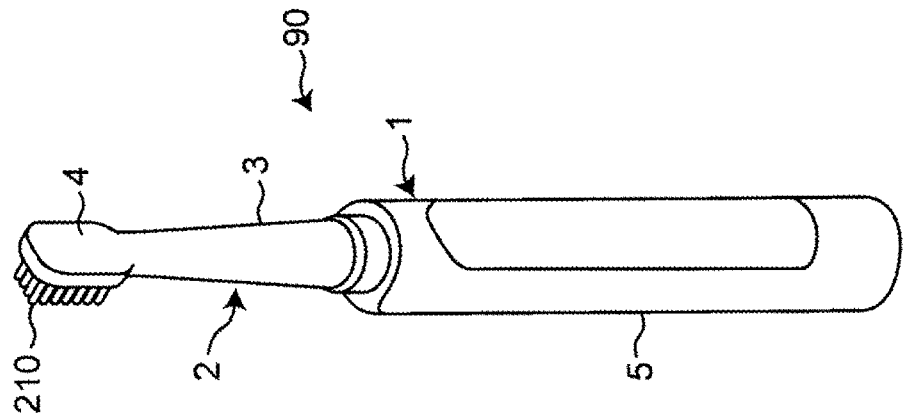
FIG. 14 (A) and FIG. 14 (B) are drawings illustrating the external appearance of an electric tooth brush of one embodiment incorporating the plaque detecting device of this invention, viewed in each case in perspective from opposite sides.
Figure 14A:
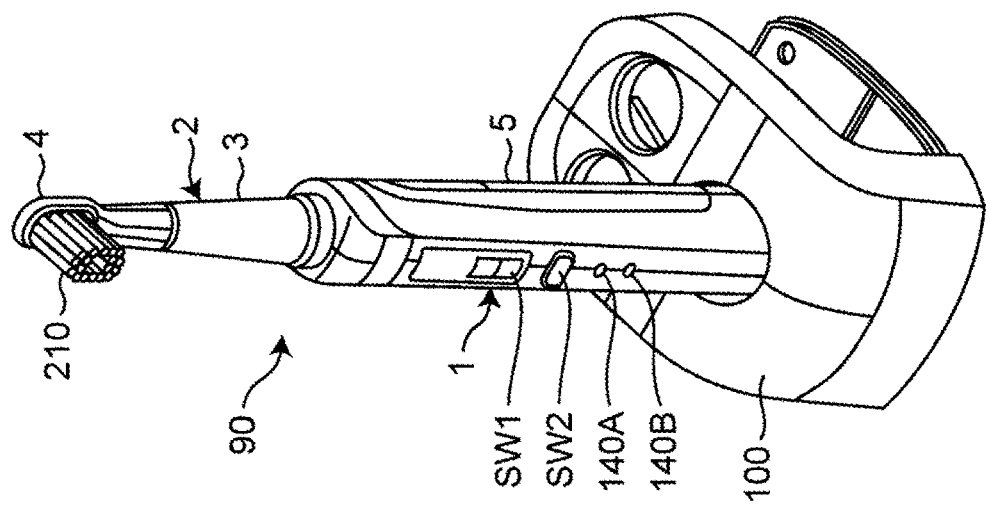

FIG. 14 (A) and FIG. 14 (B) illustrate the external appearance of an electric tooth brush (the entirety is denoted by symbol 90) of one embodiment incorporating the plaque detecting device of this invention, viewed in each case in perspective from opposite sides. This electric tooth brush 90 comprises a head section 4 with bristles 210 provided thereon, a grip section 5 intended to be gripped by hand, and a neck section 3 which links the head section 4 and grip section 5. The head section 4 and neck section 3 are integrally configured as a brush member 2 removable with respect to the grip section 5. The head section 4, neck section 3 and grip section 5 are referred to together as main body 1. For convenience of tooth brushing, the main body 1 has a slender shape in one direction. It will be noted that a charger 100 is illustrated in FIG. 14 (A).

Figure 15A:
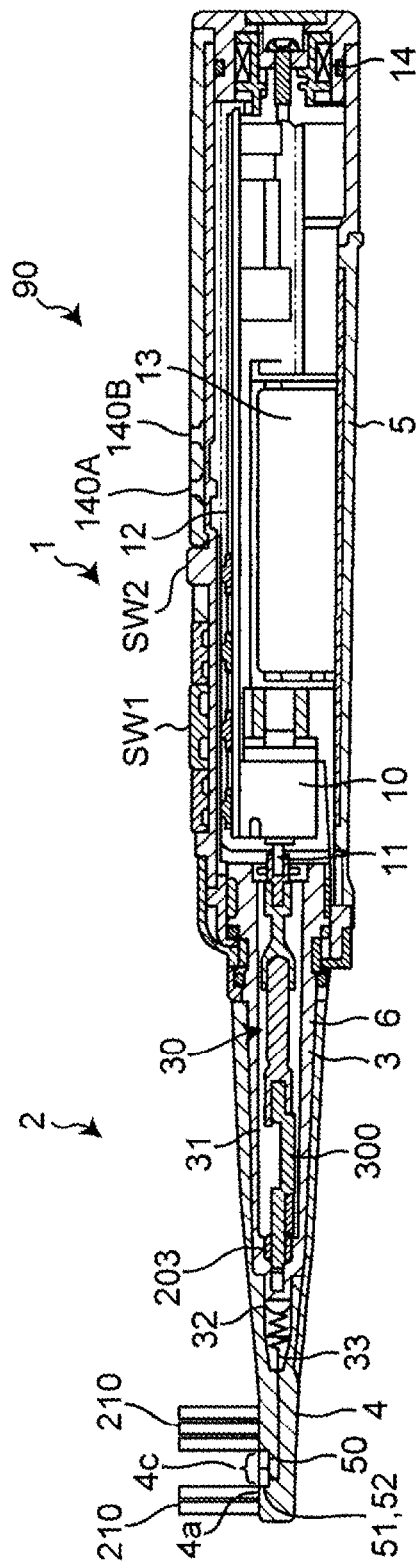
FIG. 15 (A) is a drawing illustrating the longitudinal cross-section of said electric tooth brush cut in the lengthwise direction.
Figure 15B:
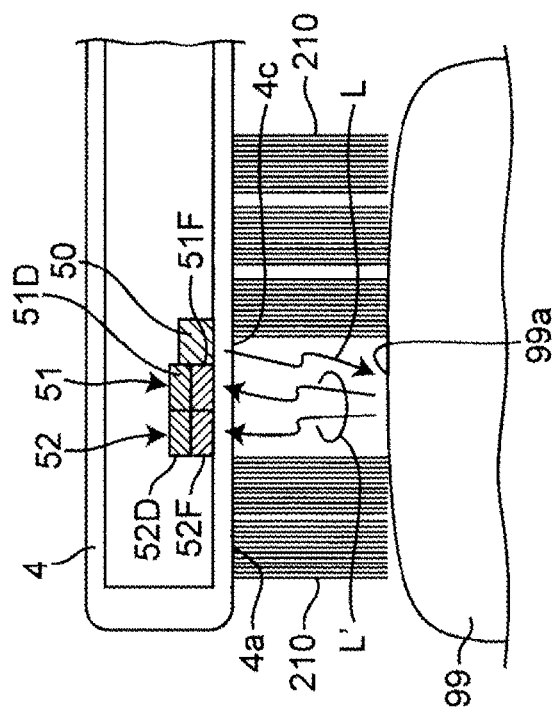

FIG. 15 (A) illustrates the longitudinal cross-section of electric tooth brush 90 cut in the lengthwise direction. The grip section 5 has a stem 6 provided so as to protrude to the neck section 3 side from the outer housing of the grip section 5. The stem 6 has a tubular shape with a closed tip end. In this example, the neck section 3 of the brush member 2 is installed by fitting so as to cover this stem 6. The brush member 2 is a consumable part, and thus is configured to be removable with respect to the grip section 5 so as to allow replacement with a new part. On the surface (bristled surface) 4a on one side of the head section 4 of the brush member 2, bristles (brush) 210 are provided so as to protrude about 10 mm to 12 mm from the bristled surface 4a, in this example, by flocking. It will be noted that the bristles 210 may also be fused or adhered instead of flocking.

A slide switch SW1 for turning the power supply on/off, a push switch SW2 for performing calibration data acquisition, described below, and LED lamps 140A, 140B are provided on the outer surface of the grip section 5 of the main body 1. Furthermore, a driving source in the form of motor 10 and driving circuit 12, and a power supply section including a rechargeable battery 13 and charging coil 14, etc., are provided inside the grip section 5. When charging the rechargeable battery 13, charging can be carried out in non-contact fashion through electromagnetic induction simply by placing the main body 1 on the charger 100 shown in FIG. 14 (A).

As shown in FIG. 15 (A), a bearing 203 is provided inside the stem 6. The tip end of eccentric shaft 30 coupled to rotary shaft 11 of motor 10 is inserted into the bearing 203. The eccentric shaft 30 has a weight 300 in the vicinity of the bearing 203, and the center of gravity of the eccentric shaft 30 is offset from its center of rotation. When the driving circuit 12 supplies a drive signal (for example, a pulse width modulation signal), corresponding to the operating mode, to the motor 10, causing the rotary shaft 11 of the motor 10 to rotate, the eccentric shaft 30 also rotates along with the rotation of rotary shaft 11. Since its center of gravity is offset from its center of rotation, the eccentric shaft 30 performs slewing motion about the center of rotation. Thus, the tip end of the eccentric shaft 30 repeatedly collides with the inner wall of the bearing 203, causing the bristles 210 to vibrate (move) at high speed.

In a specified region 4c substantially in the center of the bristled surface 4a of the head section 4, bristles are omitted. In the inner part of the head section 4 corresponding to the specified area 4c, a light emitting unit 50, first light receiving unit 51 and second light receiving unit 52 are arranged side by side. A portion (outer housing) of the bristled surface 4a of the head section 4 including at least the specified region 4c is formed from a transparent resin material (for example, acrylic resin) about 0.5 mm to 3 mm thick.

As shown in FIG. 15 (B), the light emitting unit 50 comprises a light emitting diode which irradiates excitation light L having a peak wavelength corresponding to ultraviolet or blue toward the tooth surface 99a through the specified region 4c. This light emitting diode, in this example, is an LED (model number SM0603UV-405) made by Bivar, Inc., and emits light L having a peak wavelength of 405 nm.

The first light receiving unit 51 comprises a first optical filter member 51F which receives radiated light L' from the tooth surface 99a through the specified region 4c and transmits only the spectral component of a first wavelength region of the radiated light L'; and a first photodiode 51D which receives only the spectral component of said first wavelength region which has been transmitted through the first optical filter member 51F. The first optical filter member 51F, in this example, is a long-pass filter (model number LV0610) made by Asahi Spectra Co., Ltd., which allows light with a wavelength of 610 nm or greater to pass through as said first wavelength region, while blocking light with a wavelength under 610 nm (high-pass type). The first photodiode 51D, in this example, consists of a PD (photo diode) (model number NJL6401R-3) made by New Japan Radio Co., Ltd. It will be noted that the first optical filter member 51F may also be customized so as to pass through light of wavelengths of 620 nm or greater as the first wavelength region and to block light of wavelength below 620 nm. In the following description, it will be assumed that a filter suitably customized in this manner is used as the first optical filter member 51F.

The second light receiving unit 52 comprises a second optical filter member 52F which receives radiated light L' from the tooth surface 99a through the specified region 4c and transmits only the spectral component of a second wavelength region of the radiated light L'; and a second photodiode 52D which receives only the spectral component of said second wavelength region which has been transmitted through the second optical filter member 52F. The second optical filter member 52F, in this example, is a long-pass filter (model number LV0550) made by Asahi Spectra Co., Ltd., which allows light with a wavelength of 550 nm or greater to pass through as said second wavelength region, while blocking light with a wavelength under 550 nm (high-pass type). The second photodiode 52D, in this example, just as the first photodiode 51D, consists of a PD (photo diode) (model number NJL6401R-3) made by New Japan Radio Co., Ltd.

It will be noted that the light emitting unit 50, first light receiving unit 51 and second light receiving unit 52 are each electrically connected to driving circuit 12 via lead wire 31, contact terminal 32 and spring terminal 33, as shown in FIG. 15 (A).

The first light receiving unit 51 and second light receiving unit 52 may also each consist of a phototransistor instead of a photodiode.

Furthermore, on the outer surface of the specified region 4c of the head section 4, along the bristles 210 in each of the areas corresponding to the light emitting unit 50 and first and second light receiving units 51, 52, plastic optical fibers (POFs) may be vertically arranged for guiding light. In such a case, the tips of the POFs are preferably retracted, for example by about 1.5 mm from the tips of the bristles 210 so that they do not cause interference during tooth brushing.

Figure 16:
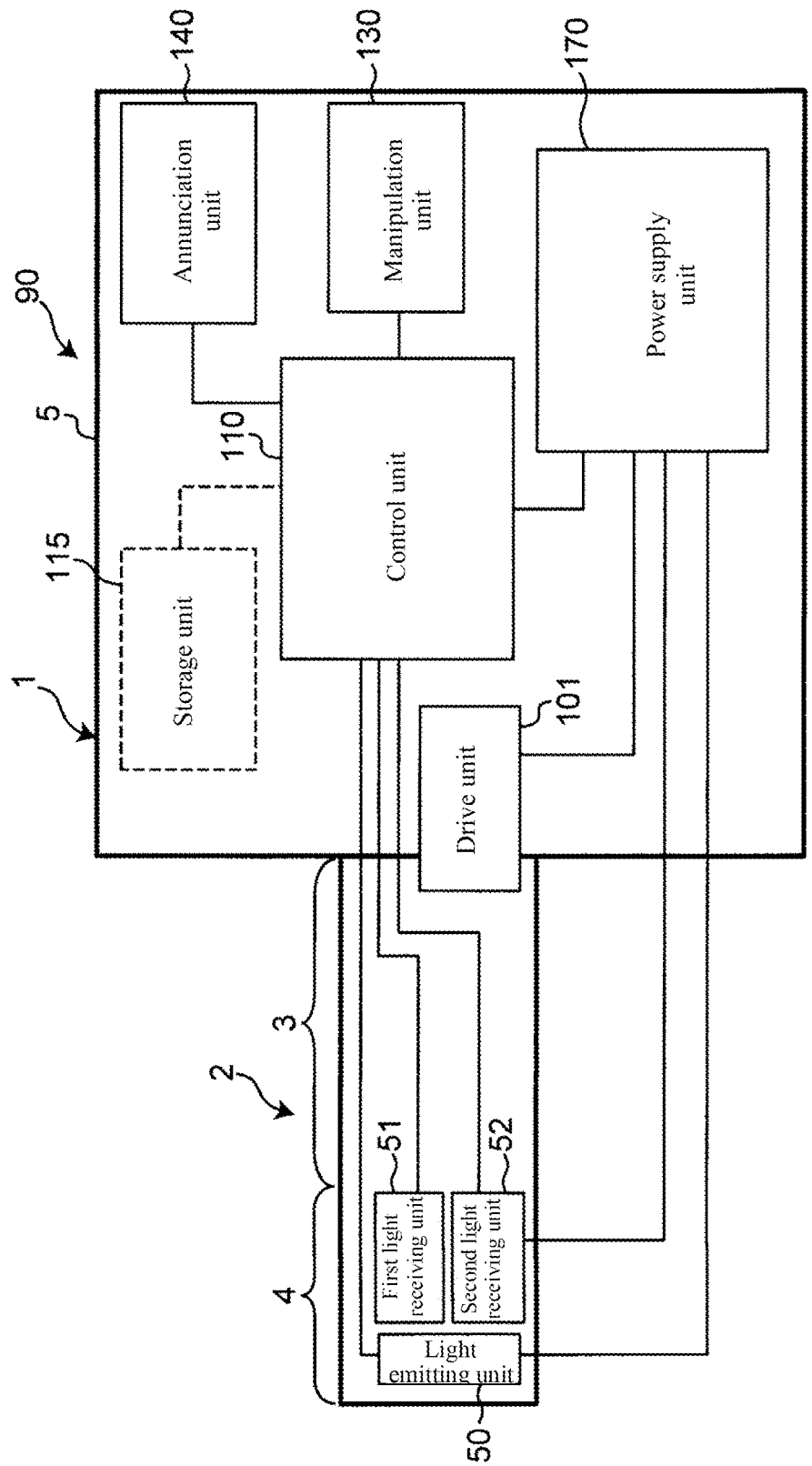
FIG. 16 is a drawing illustrating the block configuration of the control system of said electric tooth brush.

FIG. 16 illustrates the block configuration of the control system of the electric tooth brush 90. This electric tooth brush 90, inside the grip section 5, comprises a control unit 110 which constitutes the above-described driving circuit 12, a storage unit 115, manipulation unit 130, annunciation unit 140 and power supply unit 170. It should be noted that the drive unit 101 represents the already described motor 10, rotary shaft 11, eccentric shaft 30, bearing 203 and weight 300.

The control unit 110 comprises a CPU (central processing unit) which operates based on software, and in addition to driving the motor 10, performs processing for determining the presence or absence of plaque (or tartar) on the tooth surface 99a, and various other processing.

The manipulation unit 130 includes the previously described switches SW1, SW2, and functions to allow the user to turn the power supply of the electric tooth brush 90 on and off.

The storage unit 115, in this example, comprises an EEPROM (electrically rewritable nonvolatile memory) capable of non-temporary storage of data. The storage unit 115 stores a control program for controlling the control unit 110.

The annunciation unit 140, in this example, comprises a buzzer, and annunciates the presence or absence of plaque (or tartar) by sounding the buzzer. It will be noted that, instead of a buzzer, or in addition thereto, the presence or absence of plaque (or tartar) may also be annunciated by turning on or flashing the LED lamps 140A, 140B.

The power supply unit 170 includes the previously described rechargeable battery 13, and supplies power (in this example, DC 2.4 V) to the various units inside the electric tooth brush 90.

(Spectral Sensitivity)

Figure 19:
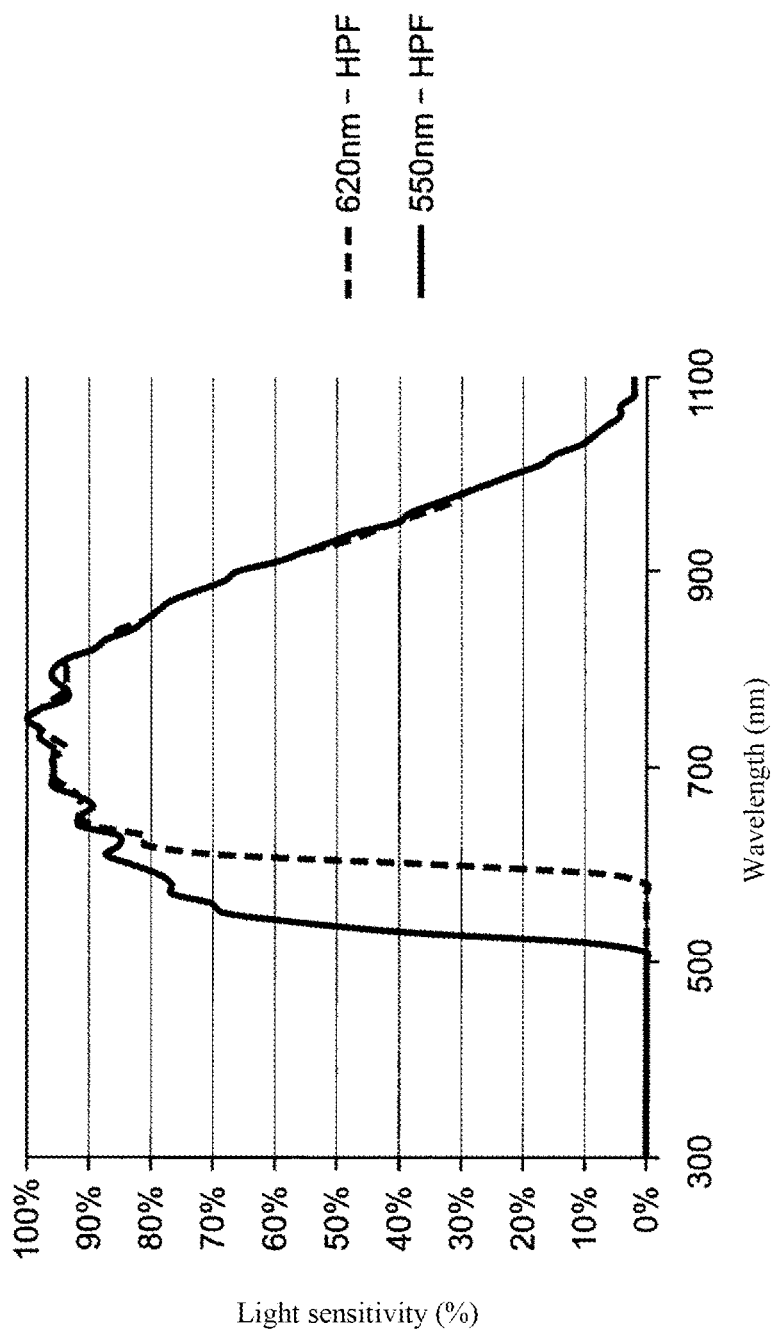
FIG. 19 is a drawing illustrating the spectral sensitivity of the first light receiving unit and second light receiving unit in said electric tooth brush.
Figure 20:
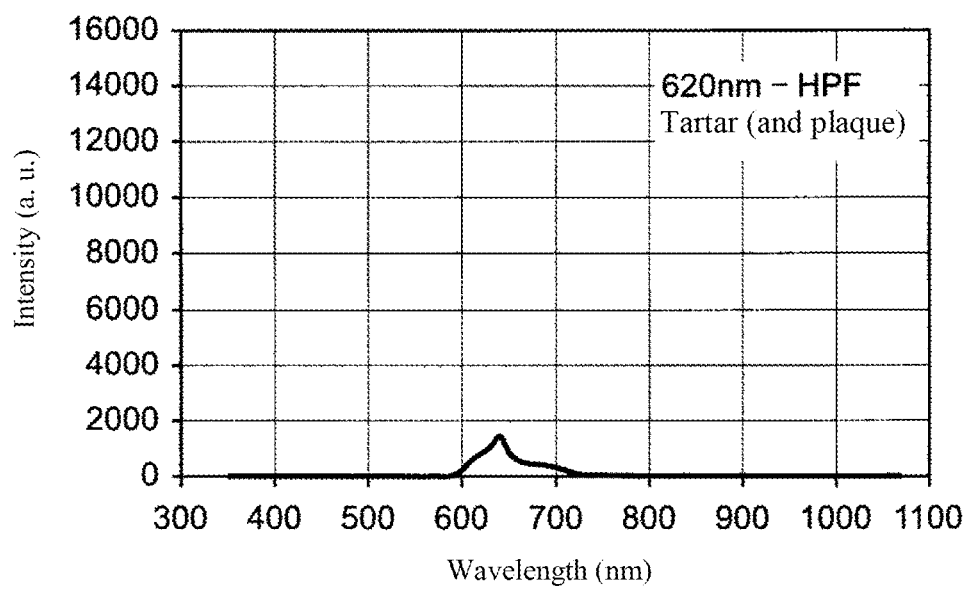
FIG. 20 is a drawing illustrating the spectral output of the first light receiving unit (first wavelength range is 620 nm or higher) when the substance present on the tooth surface is tartar (and plaque).
Figure 21:
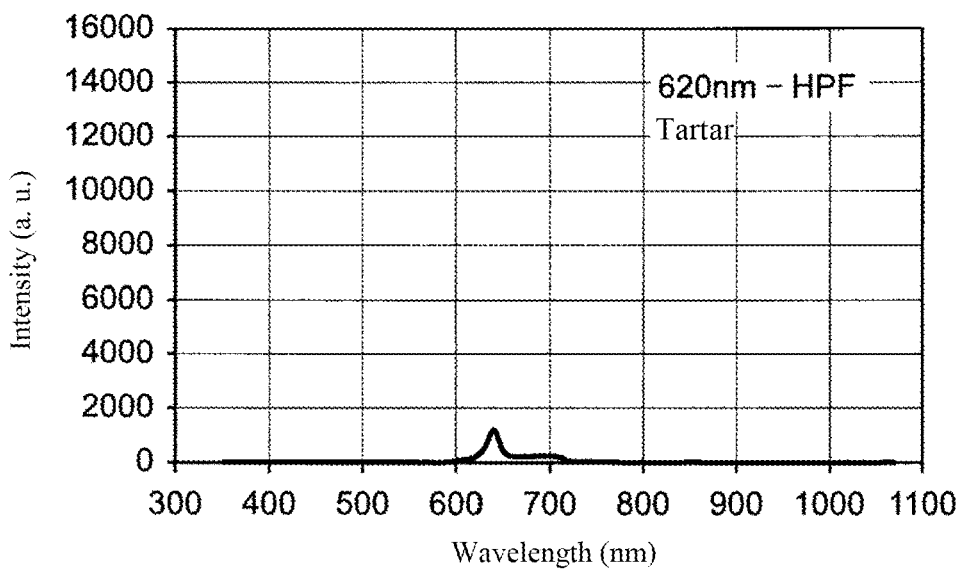
FIG. 21 is a drawing illustrating the spectral output of the first light receiving unit (first wavelength range is 620 nm or higher) when the substance present on the tooth surface is plaque.
Figure 22:
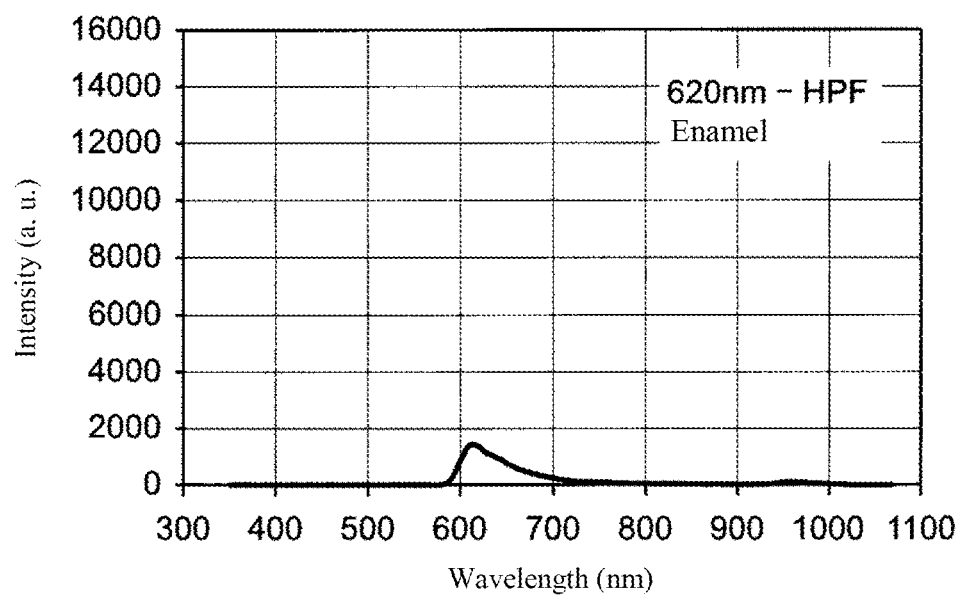
FIG. 22 is a drawing illustrating the spectral output of the first light receiving unit (first wavelength range is 620 nm or higher) when the substance present on the tooth surface is enamel.
Figure 23:
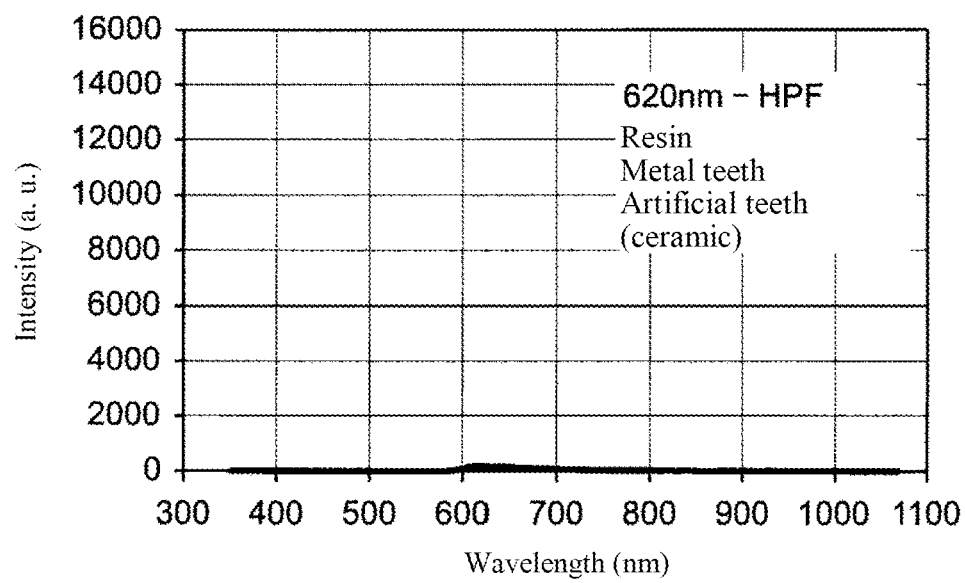
FIG. 23 is a drawing illustrating the spectral output of the first light receiving unit (first wavelength range is 620 nm or higher) when the substance present on the tooth surface is resin, metal teeth or artificial teeth (ceramic).
Figure 24:
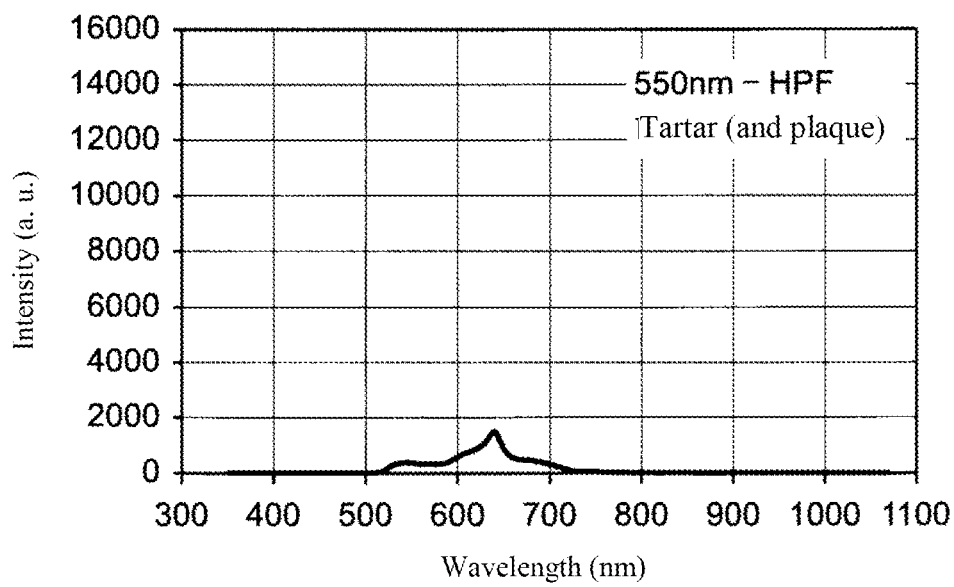
FIG. 24 is a drawing illustrating the spectral output of the second light receiving unit (second wavelength range is 550 nm or higher) when the substance present on the tooth surface is tartar (and plaque).
Figure 25:
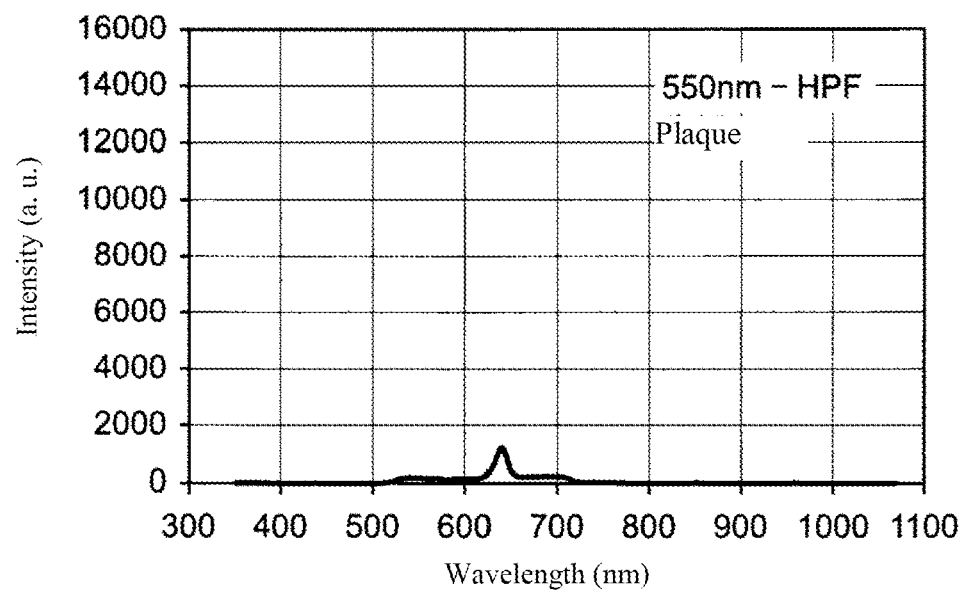
FIG. 25 is a drawing illustrating the spectral output of the second light receiving unit (second wavelength range is 550 nm or higher) when the substance present on the tooth surface is plaque.
Figure 26:
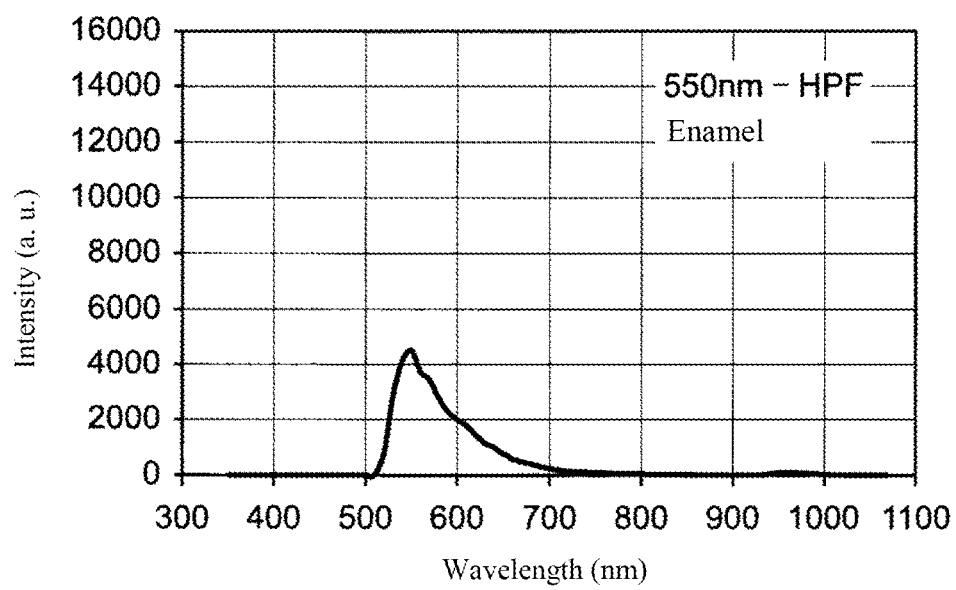
FIG. 26 is a drawing illustrating the spectral output of the second light receiving unit (second wavelength range is 550 nm or higher) when the substance present on the tooth surface is enamel.
Figure 27:
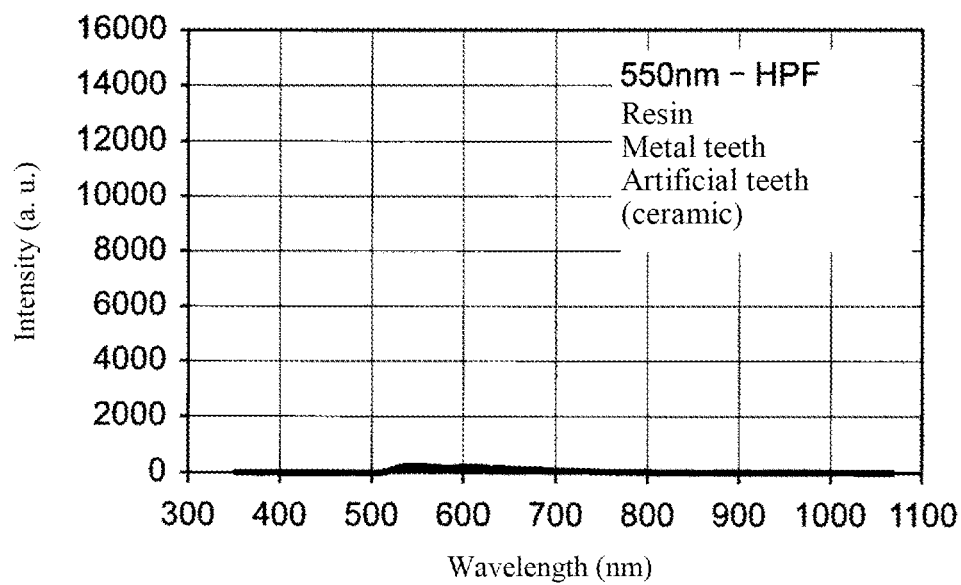
FIG. 27 is a drawing illustrating the spectral output of the second light receiving unit (second wavelength range is 550 nm or higher) when the substance present on the tooth surface is resin, metal teeth or artificial teeth (ceramic).

In FIG. 19, the spectral sensitivity of the first light receiving unit 51 (first wavelength region is 620 nm or greater) in the head section 4 of this electric tooth brush 90 is shown as a dashed line, and the spectral sensitivity of the second light receiving unit 52 (second wavelength region is 550 nm or greater) is shown as a solid line. In FIG. 19, the horizontal axis represents wavelength (units: nm), and the vertical axis represents the relative optical sensitivity (units: %) when the maximum sensitivity is taken as 100%. These spectral sensitivities, unlike the case of the spectrometer 402 in the first embodiment, are cut off on the low wavelength side by the first optical filter member 51F and second optical filter member 52F, while on the high wavelength side, the sensitivity is gradually reduced due to the characteristics of the first photodiode 51D and second photodiode 52D. As a result, the first light receiving unit 51 and second light receiving unit 52 both exhibit maximum sensitivity in the vicinity of the wavelength of 730 nm.

Furthermore, FIG. 20 through FIG. 23 show the spectral output of the first light receiving unit 51 (first wavelength region is 620 nm or greater) when the substance present on the tooth surface 99a is tartar (and plaque), plaque, enamel, resin, metal teeth and artificial teeth (ceramic), respectively. Similarly, FIG. 24 through FIG. 27 show the spectral output of the second light receiving unit 52 (second wavelength region is 550 nm or greater) when the substance present on the tooth surface 99a is tartar (and plaque), plaque, enamel, resin, metal teeth and artificial teeth (ceramic), respectively. In FIG. 20 through FIG. 27, the horizontal axis represents wavelength (units: nm), and the vertical axis represents the output intensity in arbitrary units (a. u.). The presence or absence of plaque on the tooth surface 99a is determined, in this electric tooth brush 90, based on such output.

(Evaluation of Output Level of First Light Receiving Unit and Second Light Receiving Unit)

Figure 17:
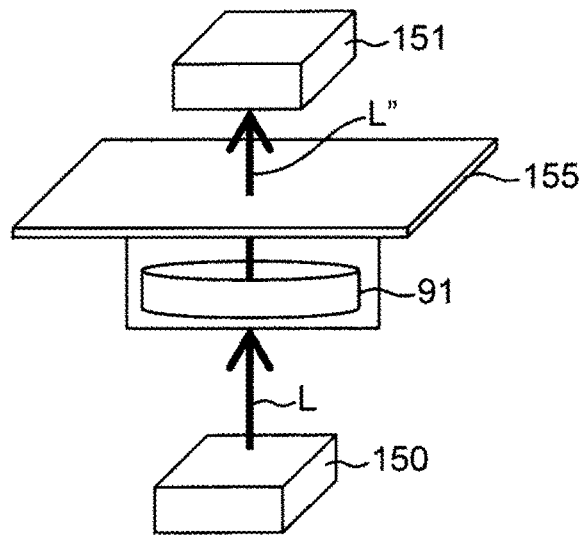
FIG. 17 is a drawing illustrating the configuration of an experimental system for evaluating the photodiode output of said electric tooth brush.

The present inventors evaluated the output level of the first light receiving unit 51 and second light receiving unit 52 in the above-described electric tooth brush 90 using the experimental system shown in FIG. 17.

The experimental system shown in FIG. 17 comprises a light emitting diode 150, plaque substitute sample (porphyrin solution) 91, optical filter member 155 and photodiode 151.

Here, the light emitting diode 150 consists of an LED (SM0603UV-405, made by Bivar, Inc.). The light emitting diode 150 irradiates excitation light L toward the plaque substitute sample 91.

The concentration of the plaque substitute sample (porphyrin solution) 91 was variably set between 1 and 10 (mg/L). This concentration range, from the standpoint of fluorescent light emission, covers a concentration range of 2 to 4 (mg/L), corresponding to plaque (or tartar) on the tooth surface 99a.

As the optical filter member 155, the same long-pass filter LV0610 and long-pass filter LV0550 that formed part of the first light receiving unit 51 and second light receiving unit 52 were used in alternation.

The photodiode 151 consisted of a PD (mode number NJL6401R-3) made by New Japan Radio Co., Ltd. The photodiode 151 receives radiated light L" (including fluorescent light) from the plaque substitute sample 91 through the optical filter member 155.

Furthermore, in the experimental system shown in FIG. 17, the distance between the light emitting diode 150 and plaque substitute sample 91 was set at 15 mm. The plaque substitute sample 91 and optical filter member 155 are arranged in contact with each other. The distance between the optical filter member 155 and photodiode 151 is set at 15 mm. These distance settings correspond to the configuration of the head section 4 shown in FIG. 15 (B) (a configuration in which bristles 210 protrude about 10 mm to 12 mm from the bristled surface 4a, and the thickness of the outer housing in the specified region 4c is about 0.5 mm to 3 mm).

Figure 18:
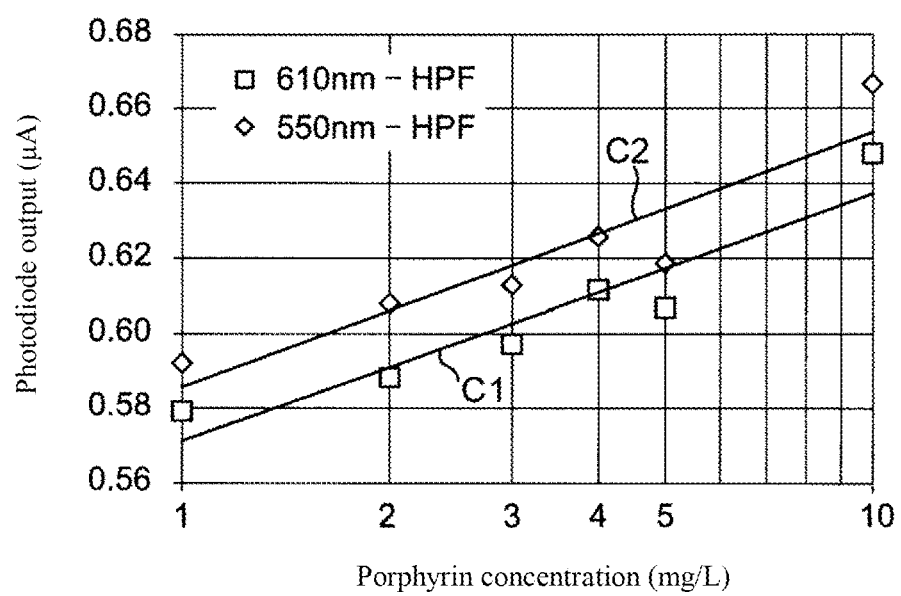
FIG. 18 is a drawing illustrating the photodiode output obtained by the experimental system of FIG. 17.

In the experimental system shown in FIG. 17, when an energizing current of 20 mA was supplied to the light emitting diode 150, an output of photodiode 151 was obtained as shown in FIG. 18. In FIG. 18, the horizontal axis represents the concentration of the plaque substitute sample (porphyrin solution) 91, and the vertical axis represents the output of the photodiode 151. Furthermore, the symbol ◇ represents data when the optical filter member 155 consists of a long-pass filter LV0610 and the first wavelength region is 610 nm or greater. The symbol ◇ represents data when the optical filter member 155 consists of long-pass filter LV0550 and the second wavelength region is 550 nm or greater. Furthermore, C1 and C2 represent straight lines fitted to the data of symbol ☐ and data of symbol ◇ respectively. From this FIG. 18, it can be seen that in the concentration range of 2 to 4 (mg/L) corresponding to plaque (or tartar), photodiode output of approximately 0.59 μA to 0.63 μA is obtained. If this photodiode output is passed, for example, through a resistor of 100 kΩ, a voltage drop of 59 mV to 63 mV is obtained. This is a voltage level that can be evaluated with a common CPU.

(Presence of and Countermeasures Against Internally Reflected Light)

Figure 28A:
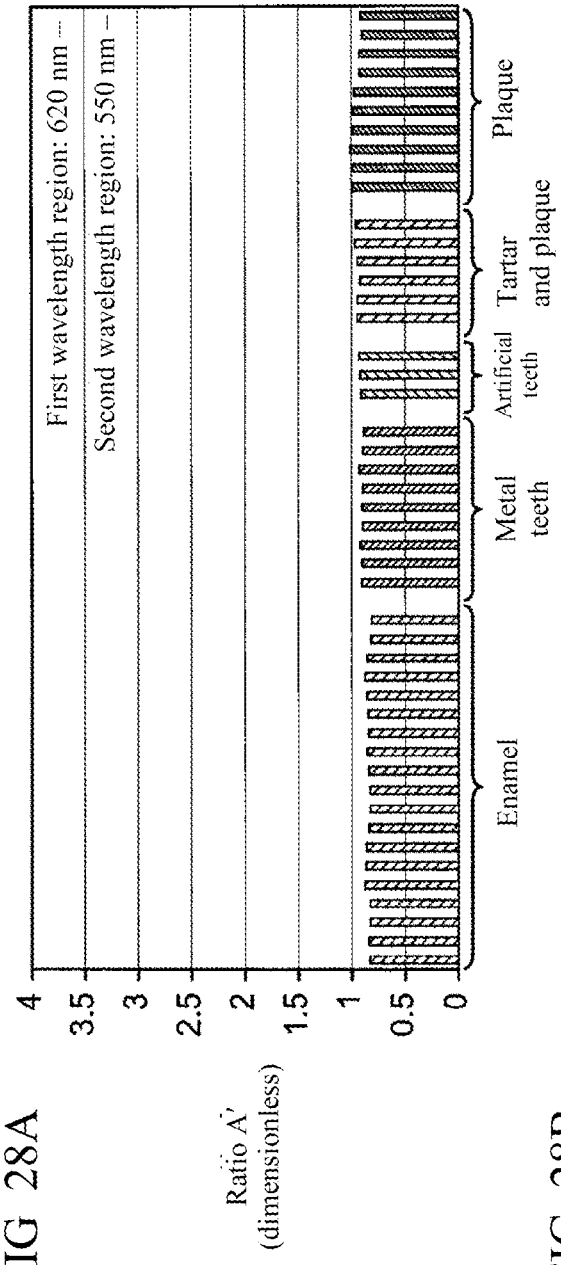
FIG. 28 (A) is a drawing showing the ratio A' between first output value $\Delta OUT1$ and second output value $\Delta OUT2$ for enamel, metal teeth, artificial teeth (ceramic), tartar (and plaque), and plaque, when no countermeasures have been taken against internally reflected light of the head section.
Figure 28B:
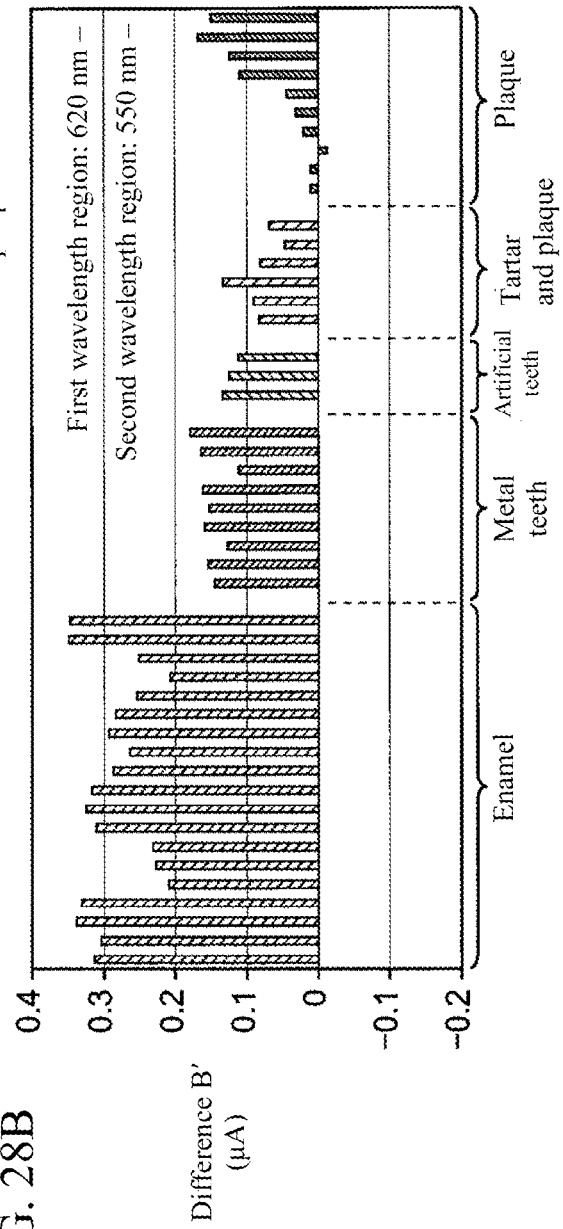

The present inventors, based on the output of the first light receiving unit 51 (first wavelength region is 620 nm or greater) and second light receiving unit 52 (second wavelength region is 550 nm or greater) in the above-described electric tooth brush 90, determined the ratio A'=ΔOUT1/ΔOUT2 using previously described (Formula 3) and determined the difference B'=ΔOUT2−ΔOUT1 using (Formula 4). The results obtained were as shown in FIG. 28 (A) and FIG. 28 (B). In FIG. 28 (A) and FIG. 28 (B), the bars arrayed horizontally correspond to samples of enamel, metal teeth, artificial teeth (ceramic), tartar (and plaque), and plaque. The vertical axis in FIG. 28 (A) represents ratio A' as a dimensionless quantity, and the vertical axis in FIG. 28 (B) represents difference B' in μA units (the same applies to FIG. 31 (A) and FIG. 31 (B), described later). As can be seen from FIG. 28 (A), in this example, for all the samples, the ratio A' was close to 1. Namely, the output ΔOUT1 of the first light receiving unit 51 and the output ΔOUT2 of the second light receiving unit 52 were nearly identical. Furthermore, as can be seen from FIG. 28 (B), the difference B' was distributed with nearly the same overlap among the groups consisting respectively of metal teeth, artificial teeth (ceramic), tartar (and plaque), and plaque. With such results, it would be difficult to distinguish and identify substances present on the tooth surface 99a.

Figure 29:
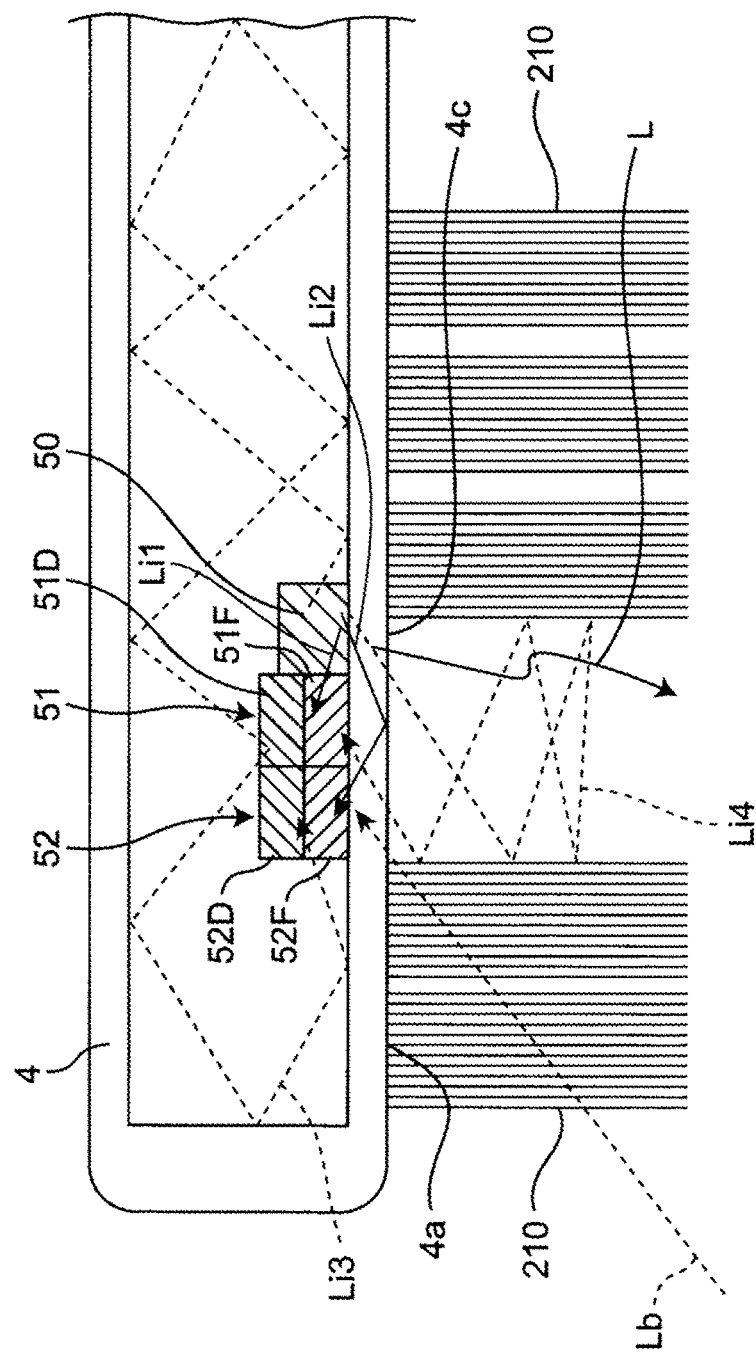
FIG. 29 is a drawing explaining internally reflected light in the head section.

The reason for such results may have been the presence of internally reflected light in the head section 4. "Internally reflected light" in the head section 4, as shown in FIG. 29, refers to excitation light L from the light emitting unit 50 which is reflected by constituent elements of the head section 4 and is inputted into the first light receiving unit 51 and second light receiving unit 52 without reaching the tooth surface. Specifically, the internally reflected light includes light Li2 which is reflected by the boundary surface of the specified region 4c in the bristled surface 4a, light Li3 which is reflected by the wall surfaces inside the head section 4 (which holds the light emitting unit 50, first light receiving unit 51 and second light receiving unit 52), light Li4 which exits outside through the boundary surface of the specified region 4c of the head section 4 but is reflected by the bristles 210 and returns, and the like. Moreover, internally reflected light may include light Li1 which enters directly from the light emitting unit 50 into first optical filter member 51F and second optical filter member 52F and is inputted into the first light receiving unit 51 and second light receiving unit 52. These lights will be hereinafter referred to collectively as internally reflected light Li.

Thus, the present inventors conceived of performing the adjustment of subtracting the components due to internally reflected light Li (which shall be represented by the symbols ΔOUT1z and ΔOUT2z) from the first output value OUT1 and second output value OUT2 in order to increase the accuracy of determination.

Figure 30A:
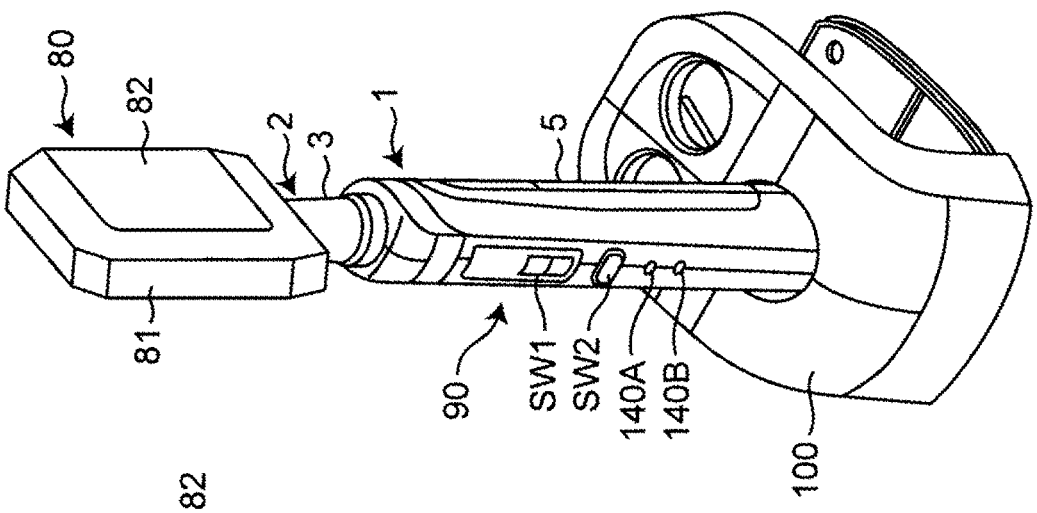
FIG. 30 (A) is a drawing illustrating a light shielding member.
Figure 30B:
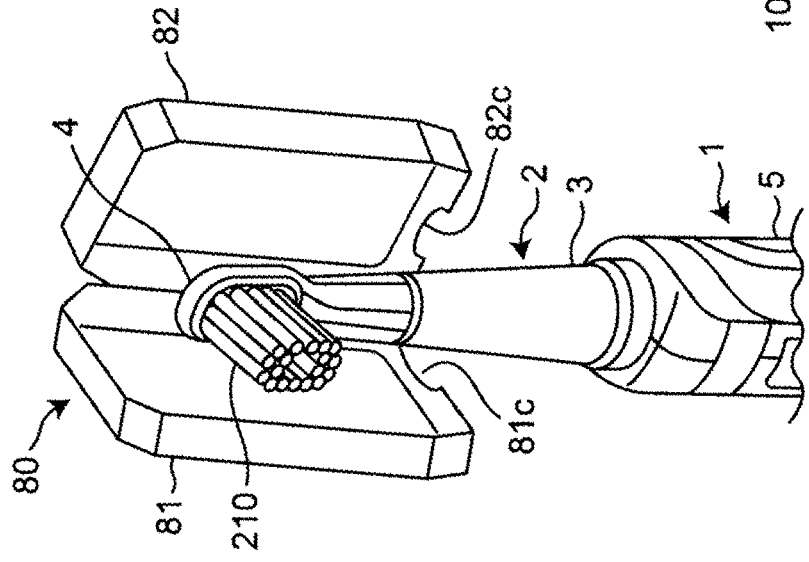
Figure 30C:
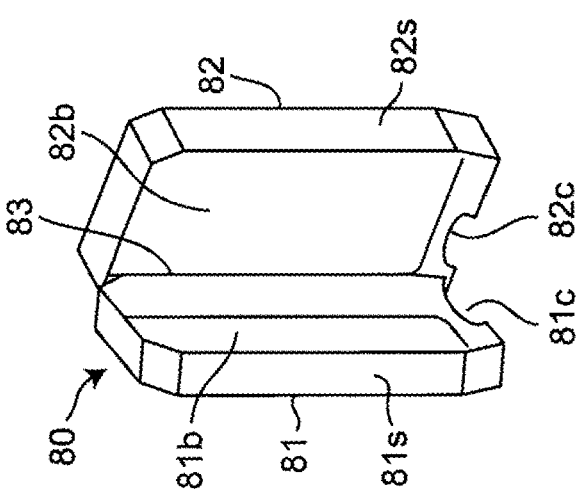

Specifically, for example as shown in FIG. 30 (A), a light shielding member 80 is provided for blocking ambient light Lb around the head section 4. In this example, the light shielding member 80 is configured as an openable and closeable box-shaped head cover consisting of a black plastic material. More specifically, the light shielding member 80 is made by integrally molding a half-box part 81 on the left side in the drawing and a half-box part 82 on the right side across one edge 83. The left side half-box part 81 comprises a main wall 81b, and an annular circumferential wall 81s which extends perpendicularly from the edge of the main wall 81b. Similarly, the right side half-box part 82 comprises a main wall 82b and an annular circumferential wall 82s which extends perpendicularly from the edge of the main wall 82b. The left side half-box part 81 and right side half-box part 82 rotate relative to each other about one edge 83, thereby making the light shielding member 80 openable and closeable. Furthermore, as shown in FIG. 30 (B), the corresponding parts of the circumferential walls 81s, 82s of the light shielding member 80 (in this example, the centers of the bottom part) are provided with semicircular cutouts 81c, 82c for just allowing the neck section 3 of the electric tooth brush 90 to pass through when the light shielding member 80 is closed. Therefore, as shown in FIG. 30 (C), when the light shielding member 80 is closed so as to cover the head section 4 along with the bristles 210, a light shielded state is achieved in which ambient light Lb around the head section 4 is substantially blocked.

In the light shielded state in which ambient light Lb has been blocked by the light shielding member 80 in this manner, the first output value and second output value (which shall be represented respectively by the symbols OUT1x and OUT2x) are obtained after turning on the light emitting unit 50, and the first output value and second output value (which shall be represented respectively by the symbols OUT1y, OUT2y) are also obtained after turning off the light emitting unit 50. Subsequently, the first output value OUT1y and second output value OUT2y when the light emitting unit 50 is turned off are subtracted respectively from the first output value OUT1x and second output value OUT2x when the light emitting unit 50 is turned on, to find the components ΔOUT1z, ΔOUT2z due to internally reflected light Li.

More specifically, as shown in Table 1 below, in the "light shielded, light emitting unit off" state A1, the first output value OUT1y and second output value OUT2y contain only the noise light component due to light (represented by symbol Lb0) consisting of ambient light Lb which has leaked past the light shielding member 80 and reached the head section 4, without any signal light component. In the "light shielded state, light emitting unit on" state A2, the first output value OUT1x and second output value OUT2x contain light Lb0 consisting of ambient light Lb which has leaked past the light shielding member 80 and reached the head section 4, without any signal light component, and internally reflected light Li, as noise light components. Therefore, the components ΔOUT1z, ΔOUT2z due to internally reflected light Li can be found based on ΔOUT1z=OUT1x−OUT1y ΔOUT2z=OUT2x−OUT2y            (Formula 5)

TABLE 1

| | | Breakdown of light receiving unit output value | |
|---|---|---|---|
| State | | Signal light component | Noise light component |
| A1 | Light shielded state, light emitting unit off | Absent | Lb0 |
| A2 | Light shielded state, light emitting unit on | Absent | Lb0 + Li |
| A3 | During tooth brushing, light emitting unit off | Absent | Lb. |
| A4 | During tooth brushing, light emitting unit on | Present | Lb + Li |

Here, the amount of light Lb0 resulting from ambient light Lb which has leaked past the light shielding member 80 and reached the head section 4 is much lower than the amount of ambient light Lb in a state without light shielding, for example, the "during tooth brushing, light emitting unit off" state A3 or the "during tooth brushing, light emitting unit on" state A4, being nearly zero. Therefore, the components ΔOUT1z and ΔOUT2z due to internally reflected light Li can be suitably obtained. As a result, the accuracy of determination can be increased by performing adjustment whereby components ΔOUT1z and ΔOUT2z due to internally reflected light Li in the head section 4 are subtracted respectively from the first output value OUT1 and second output value OUT2, as in the operation flow described later.

It will be noted that the light shielding member 80 may either be provided as a separate member, separated from the main body 1 and charger 100, or may be linked to the charger 100, for example by means of a string (not illustrated), for loss prevention purposes. Furthermore, the light shielding member 80 may also be configured so as to cover not only the head section 4 of the electric tooth brush 90 but also so as to cover, for example, the entirety of the main body 1, or the entirety of the main body 1 and charger 100.

(Ratio Between First Output Value and Second Output Value and Coefficients for Taking Difference)

The present inventors, after subtracting the components ΔOUT1z and ΔOUT2z due to internally reflected light Li respectively from the first output value OUT1 and second output value OUT2, determined the ratio A'=ΔOUT1/ΔOUT2 based on previously described (Formula 3) and the difference B'=ΔOUT2−ΔOUT1 based on (Formula 4).

Figure 31A:
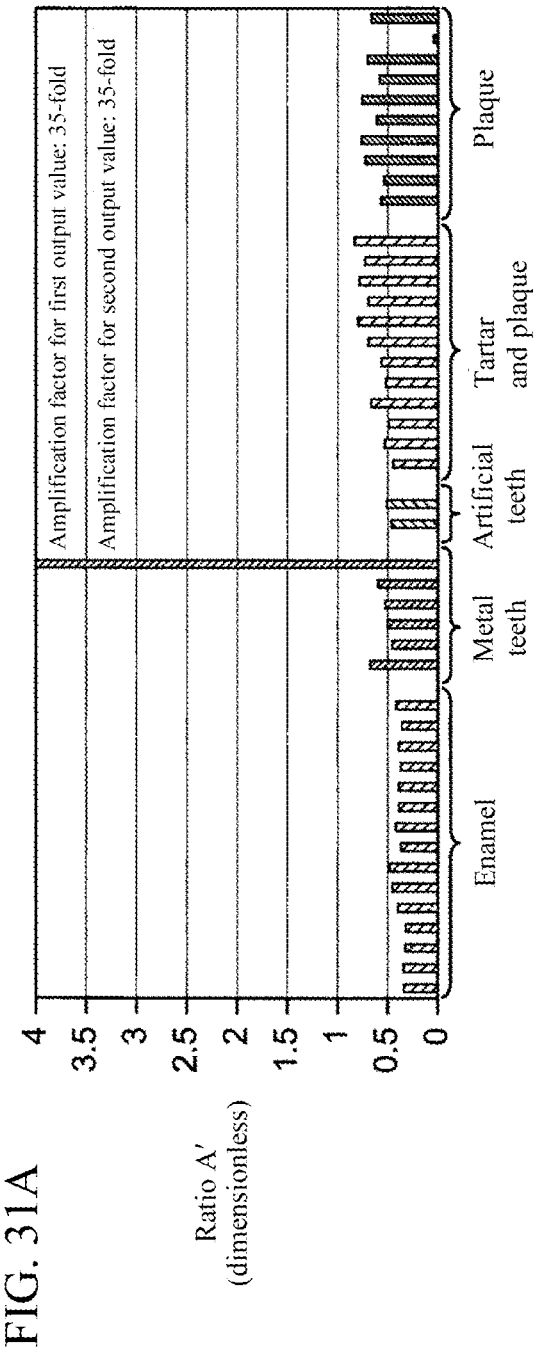
FIG. 31 (A) is a drawing showing the ratio A' between first output value $\Delta OUT1$ and second output value $\Delta OUT2$ for enamel, metal teeth, artificial teeth (ceramic), tartar (and plaque), and plaque, when countermeasures have been taken against internally reflected light of the head section.
Figure 31B:
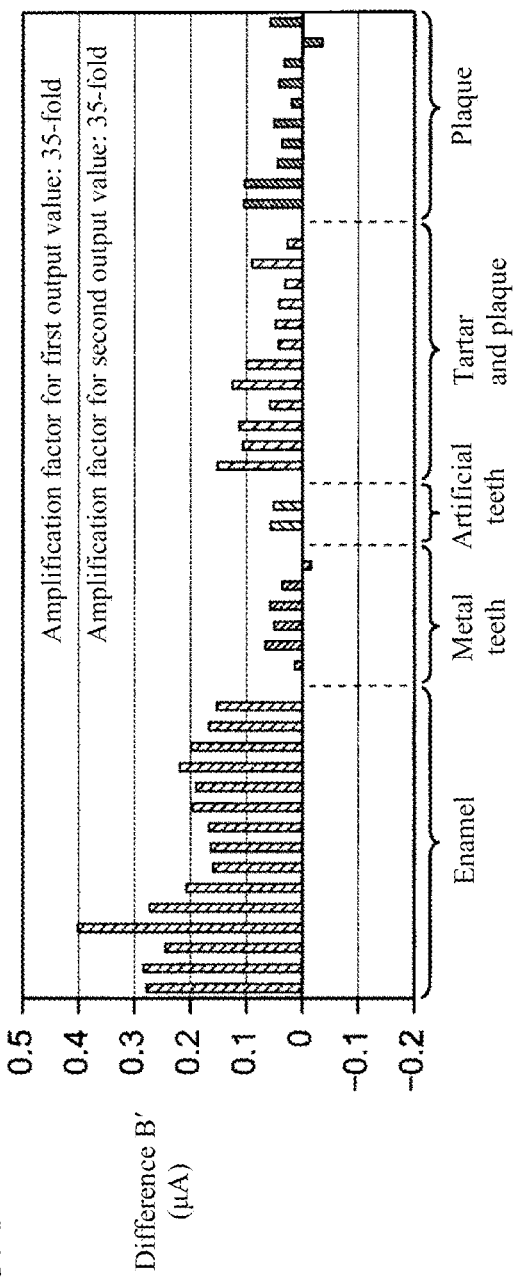

The results shown in FIG. 31 (A) and FIG. 31 (B) were thereby obtained. As can be seen from FIG. 31 (A), in this example, the ratio A' for groups consisting of enamel was between 0.3 and 0.5, while the ratio A' for groups consisting of metal teeth, artificial teeth (ceramic), tartar (and plaque), and plaque was generally greater than 0.5. Therefore, the group consisting of enamel can be identified in distinction to the group consisting of metal teeth, artificial teeth (ceramic), tartar (and plaque), and plaque. Furthermore, as can be seen from FIG. 31 (B), the differences B' are distributed with nearly the same overlap among the groups consisting respectively of metal teeth, artificial teeth (ceramic), tartar (and plaque), and plaque. With such results, it would be difficult to distinguish and identify substances present on the tooth surface 99a.

The reason for such results may have been that when computing the difference B'=ΔOUT2−ΔOUT1 based on (Formula 4), the coefficient of ΔOUT1 and the coefficient of ΔOUT2 were the same. In actuality, in the above example, the amplification factor using by the control unit 110 on the first output value ΔOUT1 and second output value ΔOUT2 was in each case 35-fold. The control unit 110 was determining the difference between the first output value ΔOUT1 which had been multiplied 35-fold and the second output value ΔOUT2 which had been multiplied 35-fold.

Here, it is preferable, for example, to compute the aforementioned difference B' between the first output value ΔOUT1 and the second output value ΔOUT2 after multiplying the first output value ΔOUT1 and second output value ΔOUT2 respectively by a first coefficient and second coefficient, which differ from each other, so that said difference B' will be different for substances of predetermined different types which may be present on the tooth surface 99a. Specifically, in the example of FIG. 31 (B), it is preferable to be able to identify the group consisting of metal teeth and artificial teeth in distinction to the group consisting of tartar (and plaque) and plaque.

Thus, the control unit 110, acting as the signal processing unit, for the processing of multiplying the first output value ΔOUT1 and second output value ΔOUT2 respectively by a first coefficient and second coefficient, which differ from each other, is made to amplify the first output value ΔOUT1 and second output value ΔOUT2 respectively by a first amplification factor and second amplification factor. As a result, the signal processing of multiplying by different coefficients is simplified. In this example, the first amplification factor for the first output value ΔOUT1 is made 51-fold, and the second amplification factor for the second output value ΔOUT2 is made 29-fold. As a result, instead of the ratio A' based on previously described (Formula 3) and difference B' based on (Formula 4), a ratio A" based on the following (Formula 6) and difference B" based on (Formula 7) are computed.

$A''=(\Delta OUT1 \times 51)/(\Delta OUT2 \times 29)$            (Formula 6)

$B''=(\Delta OUT2 \times 29)-(\Delta OUT1 \times 51)$            (Formula 7)

Figure 32A:
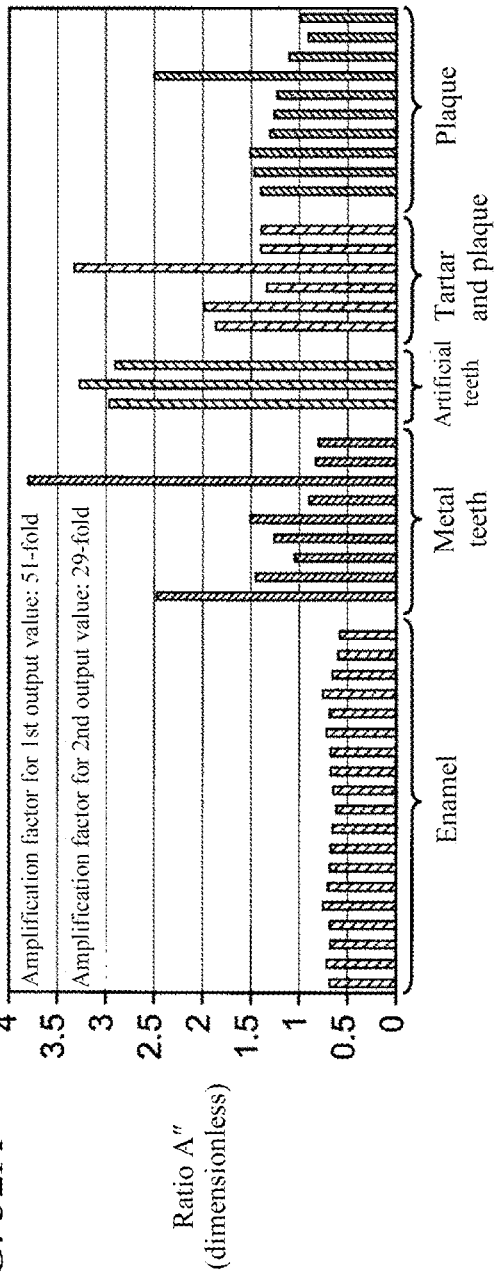
FIG. 32 (A) is a drawing showing the ratio A" between first output value $\Delta OUT1$ and second output value $\Delta OUT2$ for enamel, metal teeth, artificial teeth (ceramic), tartar (and plaque), and plaque, when countermeasures have been taken against internally reflected light of the head section and the first output value $\Delta OUT1$ and second output value $\Delta OUT2$ have been multiplied respectively by a first coefficient and second coefficient, which differ from each other.
Figure 32B:
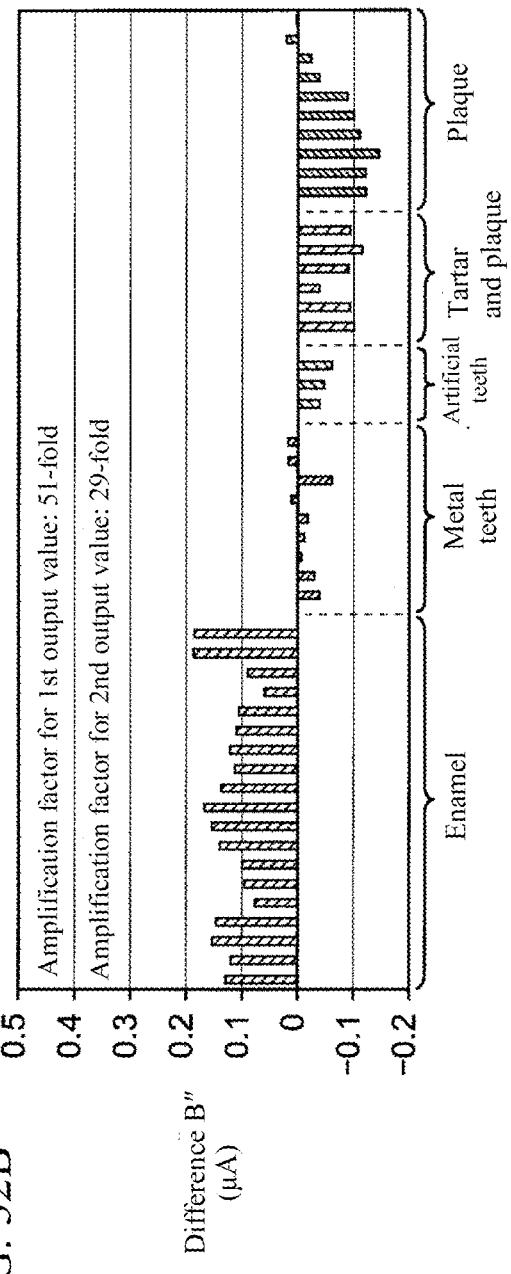
Figure 37A:
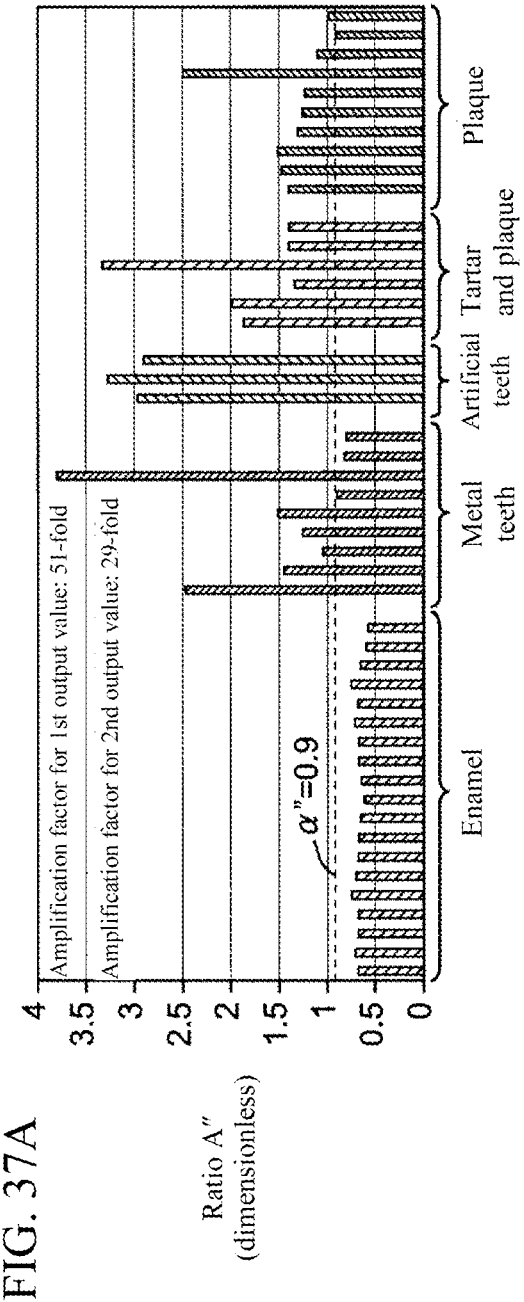
FIG. 37 FIG. 37 (A) is a drawing in which a line representing a first threshold value α" has been added to FIG. 32 (A).
Figure 37B:
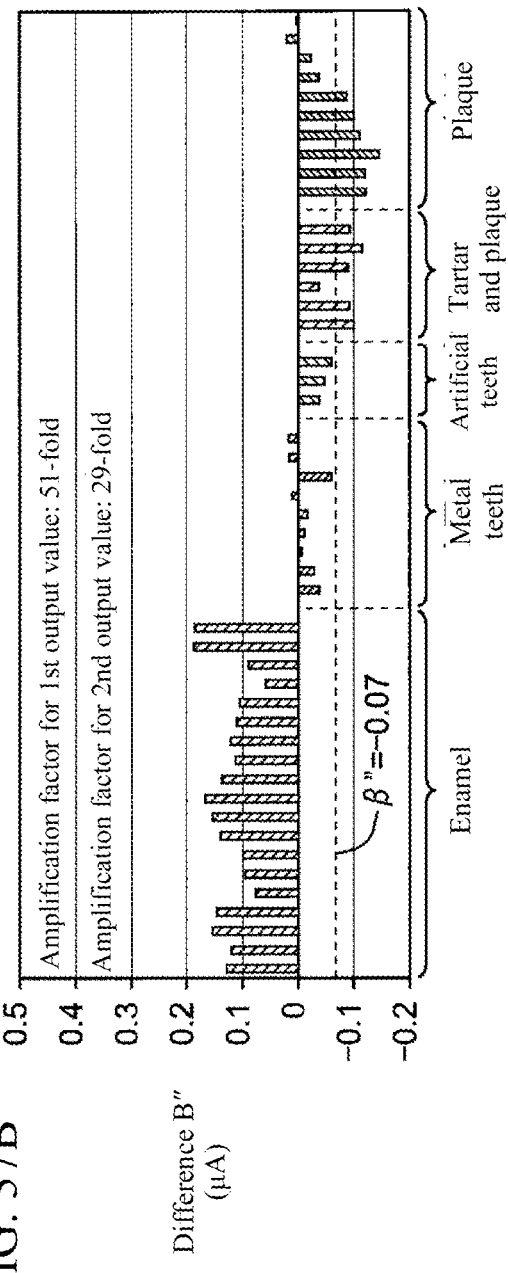

FIG. 32 (A) and FIG. 32 (B) illustrate the ratio A" obtained based on (Formula 6) and the difference B" obtained based on (Formula 7) for the same samples as in FIG. 31 (A) and FIG. 31 (B). The vertical axis in FIG. 32 (A) represents ratio A" as a dimensionless quantity, and the vertical axis in FIG. 32 (B) represents the difference B" in μA units (the same applies for FIG. 37 (A), FIG. 37 (B), FIG. 38 (A) and FIG. 38 (B), described later). As can be seen from FIG. 32 (A), the ratio A" for groups consisting of enamel was 0.5 to 0.7, while the ratio A" for groups consisting of metal teeth, artificial teeth (ceramic), tartar (and plaque), and plaque was generally greater than 0.9. Therefore, for example, as shown in FIG. 37 (A), by defining a first threshold value α"=0.9 in advance, it is possible to identify the group consisting of enamel in distinction to the group consisting of metal teeth, artificial teeth (ceramic), tartar (and plaque) and plaque. Furthermore, as can be seen from FIG. 32 (B), while the difference B" for groups consisting of enamel, metal teeth and artificial teeth (ceramic) was greater than −0.07 (μA), the difference B" for groups consisting of tartar (and plaque) and tartar was generally less than −0.07 (μA). Therefore, for example, as shown in FIG. 37 (B), by defining a second threshold value β"=−0.07 (μA) in advance, it is possible to identify the group consisting of enamel, metal teeth and artificial teeth (ceramic) in distinction to the group consisting of tartar (and plaque) and plaque.

Figure 33:
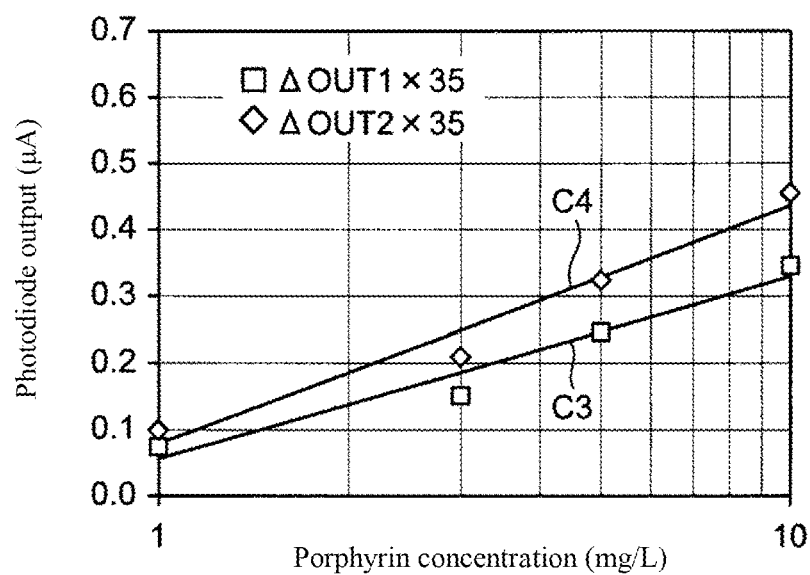
FIG. 33 is a drawing showing the first output value ΔOUT1×35 and second output value ΔOUT2×35 in μA units when the amplification factor used by the control unit for the first output value ΔOUT1 and second output value ΔOUT2 is in each case 35-fold, and the concentration of porphyrin solution is varied within the concentration range of 1 to 10 (mg/L).
Figure 34:
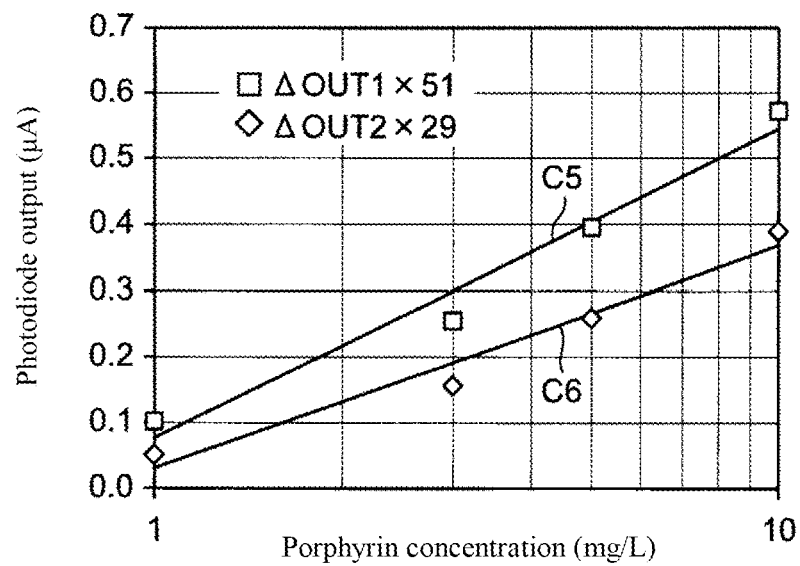
FIG. 34 is a drawing showing the first output value ΔOUT1×51 and second output value ΔOUT2×29 in μA units when the amplification factor used by the control unit for the first output value ΔOUT1 and second output value ΔOUT2 is respectively 51-fold and 29-fold, and the concentration of porphyrin solution is varied within the concentration range of 1 to 10 (mg/L).

Here, FIG. 33 shows the first output value $\Delta$OUT1×35 and second output value $\Delta$OUT2×35 in μA units for the case where the concentration of the porphyrin solution is varied within the concentration range of 1 to 10 (mg/L) when the amplification factors used by the control unit 110 for the first output value $\Delta$OUT1 and second output value $\Delta$OUT2 were both 35-fold. In this FIG. 33, the first output value $\Delta$OUT1×35 is represented by the symbol □ and the second output value $\Delta$OUT2×35 is represented by the symbol ◇. Furthermore, C3 and C4 represent straight lines fitted to the data of symbol □ and the data of symbol ◇, respectively. The slope of straight line C3 was 0.27 μA/dec, while the slope of straight line C4 was 0.36 μA/dec (where dec indicates a 10-fold difference in concentration). Furthermore, FIG. 34 shows the first output value $\Delta$OUT1×51 and second output value $\Delta$OUT2×29 in μA units for the case where the concentration of the porphyrin solution was varied within the concentration range of 1 to 10 (mg/L) when the amplification factors used by the control unit 110 for the first output value $\Delta$OUT1 and second output value $\Delta$OUT2 were respectively 51-fold and 29-fold. In this FIG. 34, the first output value $\Delta$OUT1×51 is represented by the symbol □ and the second output value $\Delta$OUT2×29 is represented by the symbol ◇. Furthermore, C5 and C6 represent straight lines fitted to the data of symbol □ and the data of symbol ◇, respectively. The slope of straight line C5 was 0.47 μA/dec, while the slope of straight line C6 was 0.34 μA/dec. As can be seen from FIG. 33 and FIG. 34 here, the effect of having different amplification factors of 51-fold and 29-fold was maintained for up to a 10-fold change in concentration of the porphyrin solution.

(Operation)

Figure 35:
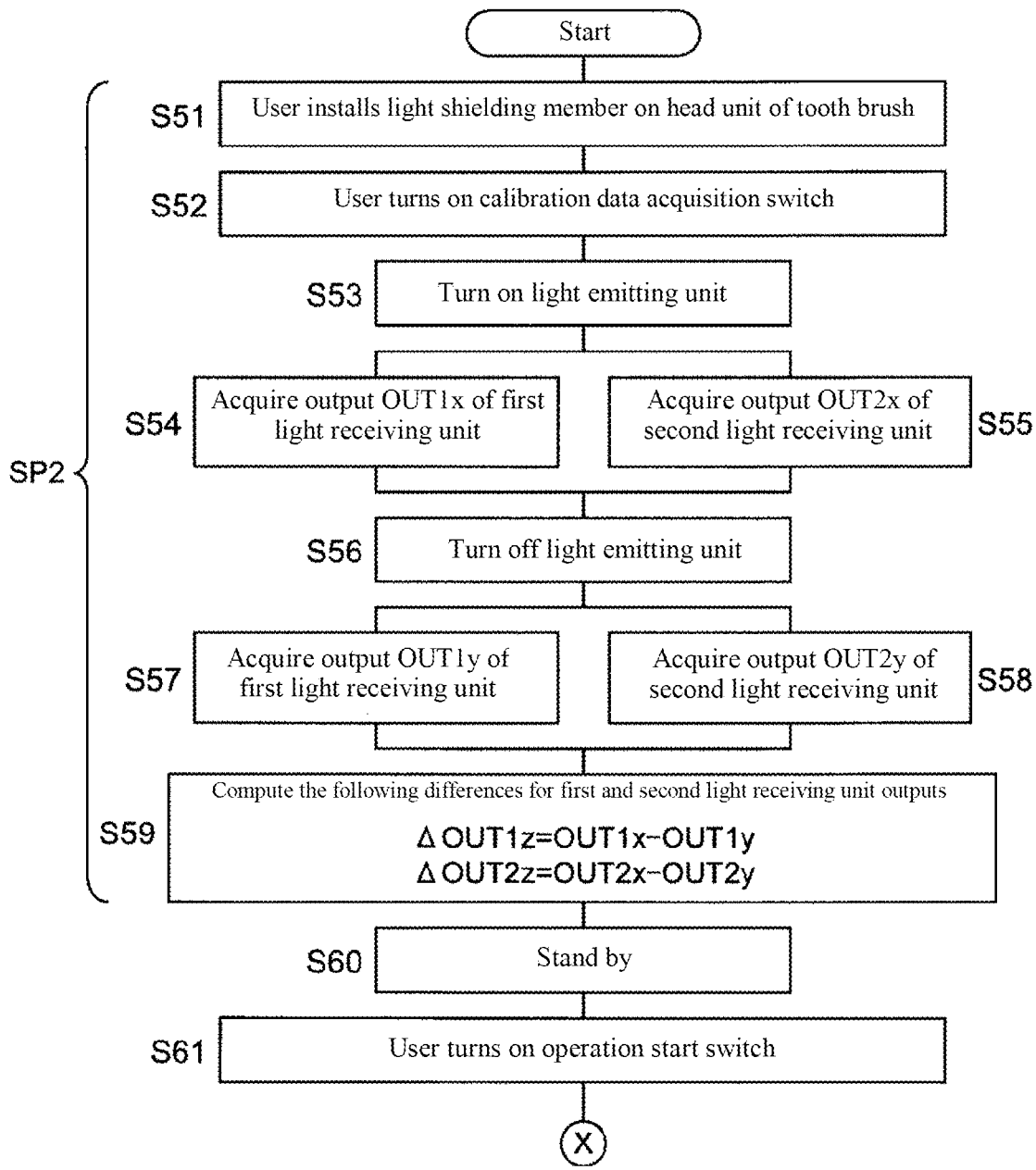
FIG. 35 is a drawing illustrating the first half (mainly, the calibration data acquisition processing) of the processing flow of the aforementioned electric tooth brush.
Figure 36:
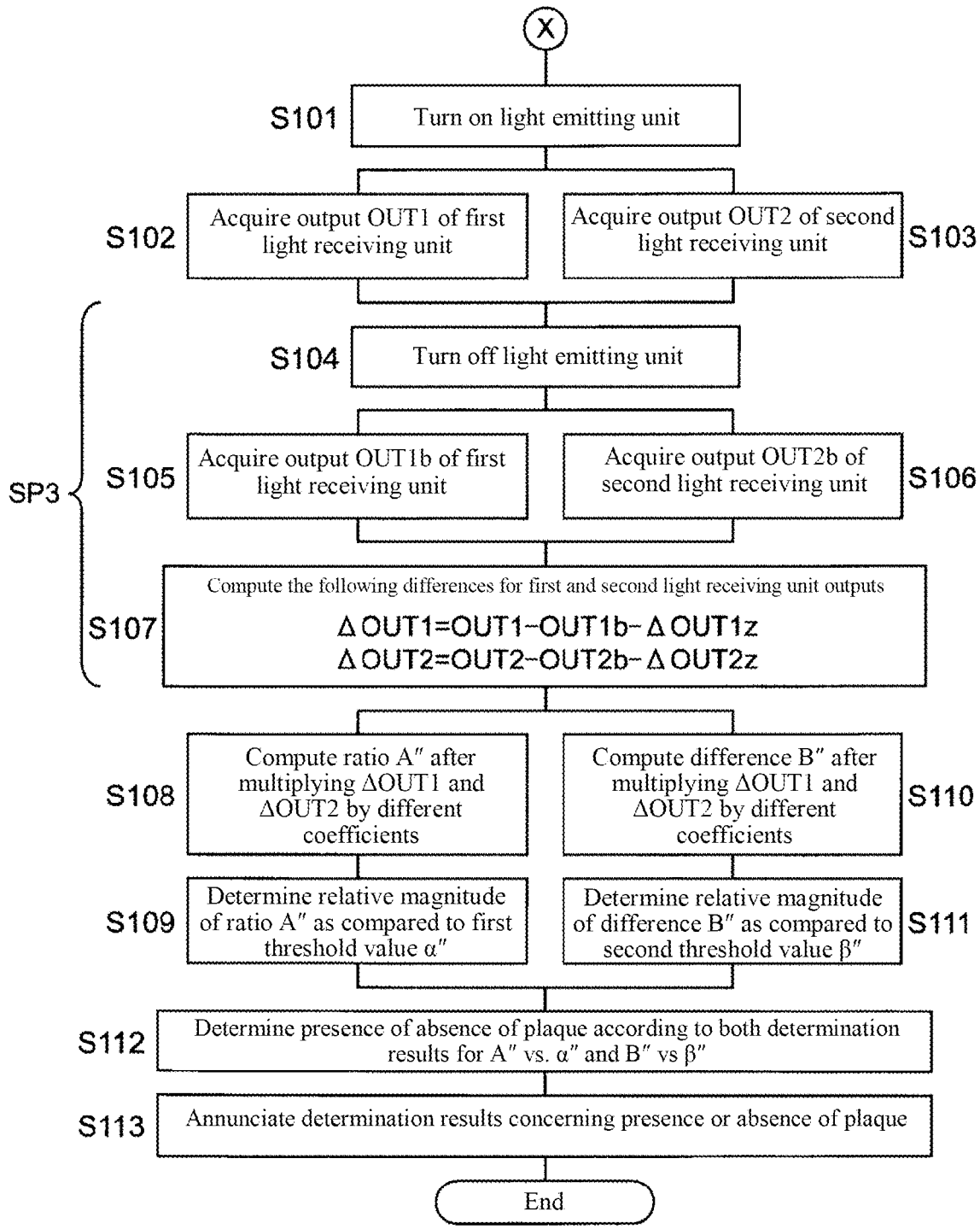
FIG. 36 is a drawing illustrating the second half of the processing flow of the aforementioned electric tooth brush.

This electric tooth brush 90 operates as a whole according to the processing flow shown in FIG. 35 through FIG. 36, in response to manipulations by the user.

(1) First, as shown in step S51 of FIG. 35, the user installs the light shielding member 80 on the head section 4 of the electric tooth brush 90 as shown in FIG. 30 (C) to place it into a light shielded state. In this light shielded state, when the user turns on the calibration data acquisition switch SW2 (step S52 of FIG. 35), with a timing based on the input of the instruction from that switch SW2, the control unit 110, acting as the second zero point adjustment unit, acquires the components $\Delta$OUT1z, $\Delta$OUT2z due to internally reflected light Li contained in the first output value OUT1 and second output value OUT2 (steps S53 through S59 of FIG. 35).

Specifically, first, the control unit 110 turns on the light emitting unit 50 (step S53 of FIG. 35) and obtains the first output value OUT1x and second output value OUT2x from the first light receiving unit 51 and second light receiving unit 52 (steps S54 and S55 of FIG. 35). Next, the control unit 110 turns off the light emitting unit 50 (step S56 of FIG. 35), and obtains the first output value OUT1y and second output value OUT2y from the first light receiving unit 51 and second light receiving unit 52 (steps S57 and S58 of FIG. 35). Then, as indicated in previously described (Formula 5), the first output value OUT1y and second output value OUT2y when the light emitting unit 50 is turned off are subtracted respectively from the first output value OUT1x and second output value OUT2x when the light emitting unit 50 is turned on to find the components $\Delta$OUT1z and $\Delta$OUT2z due to internally reflected light Li (step S59 of FIG. 35). Namely, $$\Delta OUT1z = OUT1x - OUT1y$$

$$\Delta OUT2z = OUT2x - OUT2y$$

are found. It is thereby possible to suitably obtain the components $\Delta$OUT1z, $\Delta$OUT2z due to internally reflected light Li in the state where ambient light Lb around the head section 4 is nearly zero. The control unit 110 stores the found components $\Delta$OUT1z, $\Delta$OUT2z due to internally reflected light Li in storage unit 115. It will be noted that steps S51 through S59 of FIG. 35 as a whole represent the calibration data acquisition processing SP2 for finding the components $\Delta$OUT1z, $\Delta$OUT2z due to internally reflected light Li.

The control unit 110 then stands by (step S60 of FIG. 35) and waits for the user to turn on the operation start switch SW1.

(2) Here, as shown in FIG. 15 (B), when the user places the bristles 210 of the head section 4 of the electric tooth brush 90 against the tooth surface 99a and turns the operation start switch SW1 on (step S61 of FIG. 35), the control unit 110 causes the motor 10 to rotate, causing the bristles 210 to vibrate (move) at high speed (tooth brushing start). Furthermore, the control unit 110, as discussed below, executes processing for determining the presence or absence of plaque (or tartar) on the tooth surface 99a.

(3) Specifically, the control unit 110 turns on the light emitting unit 50 (step S101 of FIG. 36) and causes excitation light L to be irradiated from the light emitting unit 50 through the specified region 4c toward the tooth surface 99a, as shown in FIG. 15 (B). In response, radiated light L' is radiated from the tooth surface 99a. This radiated light L' passes through the specified region 4c and is received by the first light receiving unit 51 and second light receiving unit 52. As a result, the control unit 110 acquires the first output value OUT1 and second output value OUT2 from the first light receiving unit 51 and second light receiving unit 52 respectively, as shown in steps S102 and S103 of FIG. 36. The first output value OUT1 and second output value OUT2 contain a component due to ambient light Lb and a component due to internally reflected light Li as noise light components, in addition to the signal light component due to radiated light L', as indicated for state A4 "during tooth brushing, light emitting unit on" in Table 1, discussed previously.

(4) Subsequently, the control unit 110 turns off the light emitting unit 50 (step S104 of FIG. 36). Thereupon, only the ambient light Lb around the tooth surface 99a (or head section 4) is received by the first light receiving unit 51 and second light receiving unit 52, as indicated for state A3 "during tooth brushing, light emitting unit off" in Table 1. As a result, the control unit 110 acquires the first output value OUT1b and second output value OUT2b representing components due to ambient light Lb from the first light receiving unit 51 and second light receiving unit 52, as shown in steps S105 and S106 of FIG. 36. It will be noted that this acquisition of components due to ambient light Lb may be carried out either at start of tooth brushing or during tooth brushing.

(5) Next, the control unit 110, acting as the first and second zero point adjustment units, as shown in step S107 of FIG. 36, performs adjustment by subtracting components due to ambient light Lb around the tooth surface 99a (namely, OUT1b and OUT2b) and components due to internally reflected light Li (namely, ΔOUT1z and ΔOUT2z) from the first output value OUT1 and second output value OUT2. Specifically, the differences $$\Delta OUT1 = OUT1 - OUT1b - \Delta OUT1z \qquad \text{(Formula 8)}$$

$$\Delta OUT2 = OUT2 - OUT2b - \Delta OUT2z \qquad \text{(Formula 9)}$$

are computed respectively as the adjusted first output value ΔOUT1 and second output value ΔOUT2. It will be noted that the processing from step S104 to S107 in FIG. 36 is referred to collectively as zero point adjustment processing SP3. Performing this zero point adjustment processing SP3 makes it possible to suitably eliminate the effect of the component due to ambient light Lb and the component due to internally reflected light Li and increase the accuracy of determination of the presence or absence of plaque, described below.

(6) Next, the control unit 110, as shown in step S108 of FIG. 36, multiplies the aforementioned adjusted first output value ΔOUT1 and second output value ΔOUT2 respectively by a first coefficient and second coefficient which differ from each other (namely, in this example, the first output value ΔOUT1 and second output value ΔOUT2 are amplified by a first amplification factor (51-fold) and second amplification factor (29-fold which differ from each other), and then computes the ratio A" between them. Specifically, the ratio A" is computed according to previously described (Formula 6) as follows.

$$A'' = (\Delta OUT1 \times 51)/(\Delta OUT2 \times 29)$$

Furthermore, the control unit 110, acting as the first determination unit, as shown in step S109 of FIG. 36, performs determination of the relative magnitude of this ratio A" as compared to a predetermined first threshold value α".

More specifically, in this example, it will be assumed that the ratio A" between the first output value ΔOUT1 and the second output value ΔOUT2 is as shown by the bar graph in FIG. 37 (A). As discussed previously, in the example of FIG. 37 (A), the ratio A" for the groups consisting of enamel is between 0.5 and 0.7, while the ratio A" for groups consisting of metal teeth, artificial teeth (ceramic), tartar (and plaque), and plaque is generally greater than 0.9. Therefore, setting a first threshold value α"=0.9 in advance makes it possible to identify the group consisting of enamel in distinction to the group consisting of metal teeth, artificial teeth (ceramic), tartar (and plaque), and plaque.

(7) Next, the control unit 110, as shown in step S110 of FIG. 36, multiplies the aforesaid adjusted first output value ΔOUT1 and second output value ΔOUT2 by coefficients that differ from each other (namely, in this example, the first output value ΔOUT1 and second output value ΔOUT2 are amplified respectively by a first amplification factor (51-fold) and second amplification factor (29-fold) which differ from each other), after which the difference B" between them is computed. Specifically, the difference B" is computed according to above-described (Formula 7) as follows.

$$B'' = (\Delta OUT2 \times 29) - (\Delta OUT1 \times 51)$$

Furthermore, the control unit 110, acting as the second determination unit, as shown in FIG. S111 of FIG. 36, performs determination of the relative magnitude of this difference B" as compared to a predetermined threshold value β".

More specifically, in this example, it will be assumed that the difference B" between the first output value ΔOUT1 and the second output value ΔOUT2 is as shown by the bar graph in FIG. 37 (B). As discussed previously, in the example of FIG. 37 (B), the difference B" for the groups consisting of enamel metal, teeth and artificial teeth (ceramic) is greater than −0.07 (μA), while the difference B" for the groups consisting of tartar (and plaque) and plaque is generally less than −0.07 (μA). Therefore, setting a second threshold value β"=−0.07 (μA) in advance makes it possible to identify the group consisting of enamel, metal teeth and artificial teeth (ceramic) in distinction to the group consisting of tartar (and plaque) and plaque.

It will be noted that the determination of relative magnitude between the ratio A" and first threshold value α" under (6) above and the determination of relative magnitude between the difference B" and second threshold value β" under (7) above may be carried out one after the other or in parallel.

(8) Next, the control unit 110, acting as a combined determination unit, as shown in step S112 of FIG. 36, based on a combination of the determination results of the relative magnitude of ratio A" as compared to the first threshold value α" under (6) above and the determination results of the relative magnitude of the difference B" as compared to the second threshold value β" under (7) above, determines if the substance present on the tooth surface 99a is plaque (or tartar) or not.

Figure 38A:
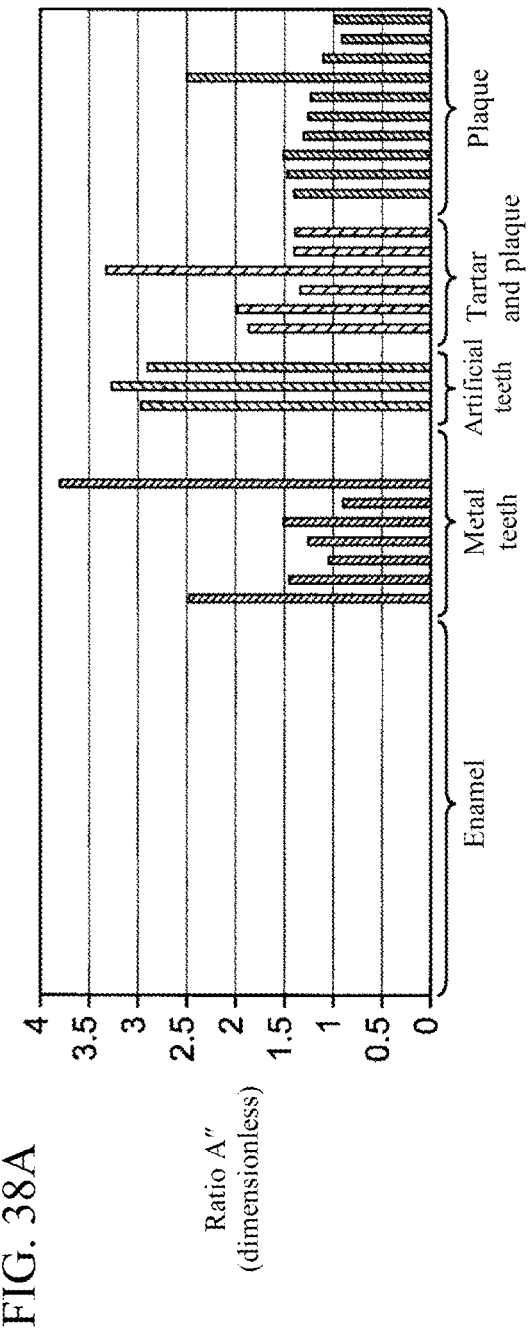
FIG. 38 FIG. 38 (A) and FIG. 38 (B) are drawings illustrating the process of determination of the presence or absence of plaque or tartar based on ratio A" and difference B".
Figure 38B:
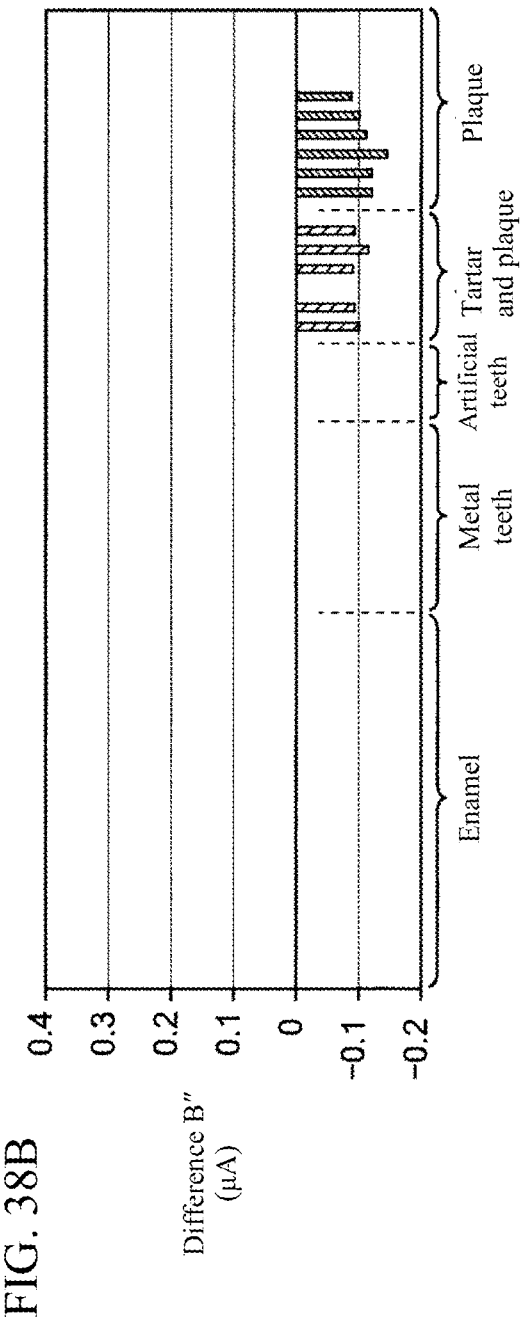

Specifically, in the case where the substance present on the tooth surface 99a is plaque (or tartar), for example, first, based on the determination according to (6) above, as shown in FIG. 38 (A), the substance present on the tooth surface 99a is identified as being a substance belonging to the group consisting of metal teeth, artificial teeth (ceramic), tartar (and plaque), and plaque. Next, based on the determination according (7) above, as shown in FIG. 38 (B), that substance is identified as being not metal teeth or artificial teeth (ceramic), but rather tartar (and plaque) or plaque. In this example, the plaque-tartar determination rate (the proportion of samples correctly determined to be plaque or tartar from among 16 samples of plaque or tartar) was (plaque-tartar determination rate)=11 samples/16 samples=69(%). Furthermore, the false determination rate (the proportion of samples incorrectly determined to be plaque or tartar out of 31 samples of enamel, metal teeth or artificial teeth (ceramic)) was (false determination rate)=0 samples/31 samples=0%. In this way, by performing the zero point adjustment processing SP3 of FIG. 36 (steps S104 through S107), the effect of the component due to ambient light Lb and the component due to internally reflected light Li can be suitably eliminated and the accuracy of determination of the presence or absence of plaque can be increased.

(9) Subsequently, as shown in step S113 of FIG. 36, the control unit 110 annunciates the presence or absence of plaque (or tartar), in this example, by sounding a buzzer using the annunciation unit 140. It will be noted that, instead of sounding a buzzer, or in addition thereto, the presence or absence of plaque (or tartar) may also be annunciated by turning on or flashing the LED lamps 140A, 140B.

Therefore, the user is able to find out the determination results concerning the presence or absence of plaque (or tartar) while brushing teeth. This makes it possible to omit optical fiber, wires or the like extending to the outside from the electric tooth brush 90. Doing so allows the user to easily perform tooth brushing without obstacles when tooth brushing is performed using this electric tooth brush 90.

Furthermore, in this electric tooth brush 90, the first light receiving unit 51 and second light receiving unit 52 can be configured more simply, without using a spectrometer or the like. Therefore, this electric tooth brush 90 can be manufactured compactly and at low cost.

In the above example, for the processing of multiplying the first output value $\Delta OUT1$ and second output value $\Delta OUT2$ respectively by a first coefficient and second coefficient which differ from each other in (Formula 6) and (Formula 7), the control unit 110 is made to amplify the first output value $\Delta OUT1$ and second output value $\Delta OUT2$ respectively by a first amplification factor and second amplification factor which differ from each other. However, the invention is not limited thereto. It is also possible to make the light receiving surface area of the first light receiving unit 51 and the light receiving surface area of the second light receiving unit 52 different from each other such that the difference B" between the first output value $\Delta OUT1$ and the second output value $\Delta OUT2$ will differ for predetermined different types of substances which may be present on the tooth surface 99a. It would thereby be sufficient for the control unit 110 to simply find ratio A' of (Formula 3) and difference B' of (Formula 4), instead of ratio A" of (Formula 6) and difference B" of (Formula 7), allowing the signal processing to be simplified. As a result, just as in the example described above, the difference B" between the first output value $\Delta OUT1$ and the second output value $\Delta OUT2$ will differ for predetermined different types of substances which may be present on the tooth surface 99a.

Modified Example 1

Figure 39B:
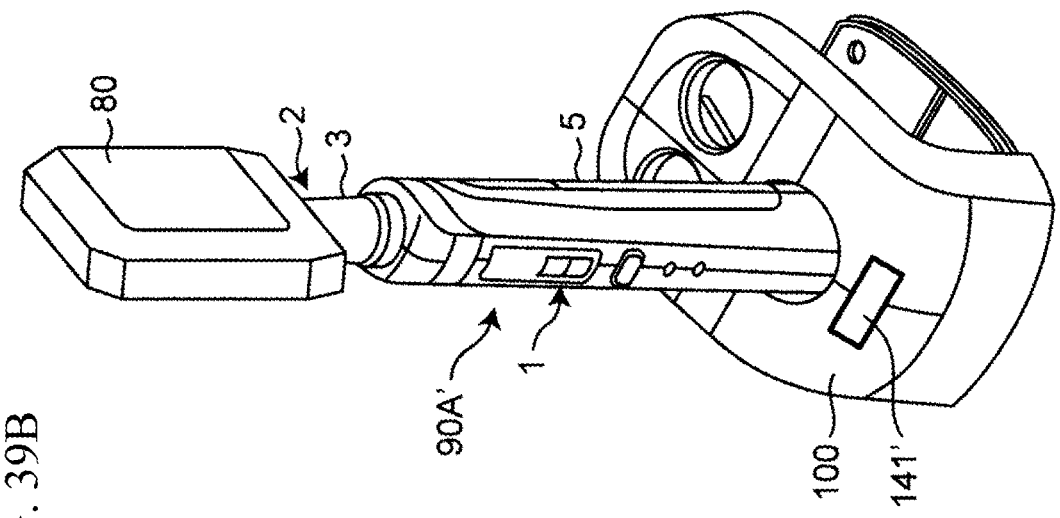
FIG. 39 FIG. 39 (A) is a drawing showing the external appearance of modified example 1, in which the aforementioned electric tooth brush has been modified.
Figure 39A:
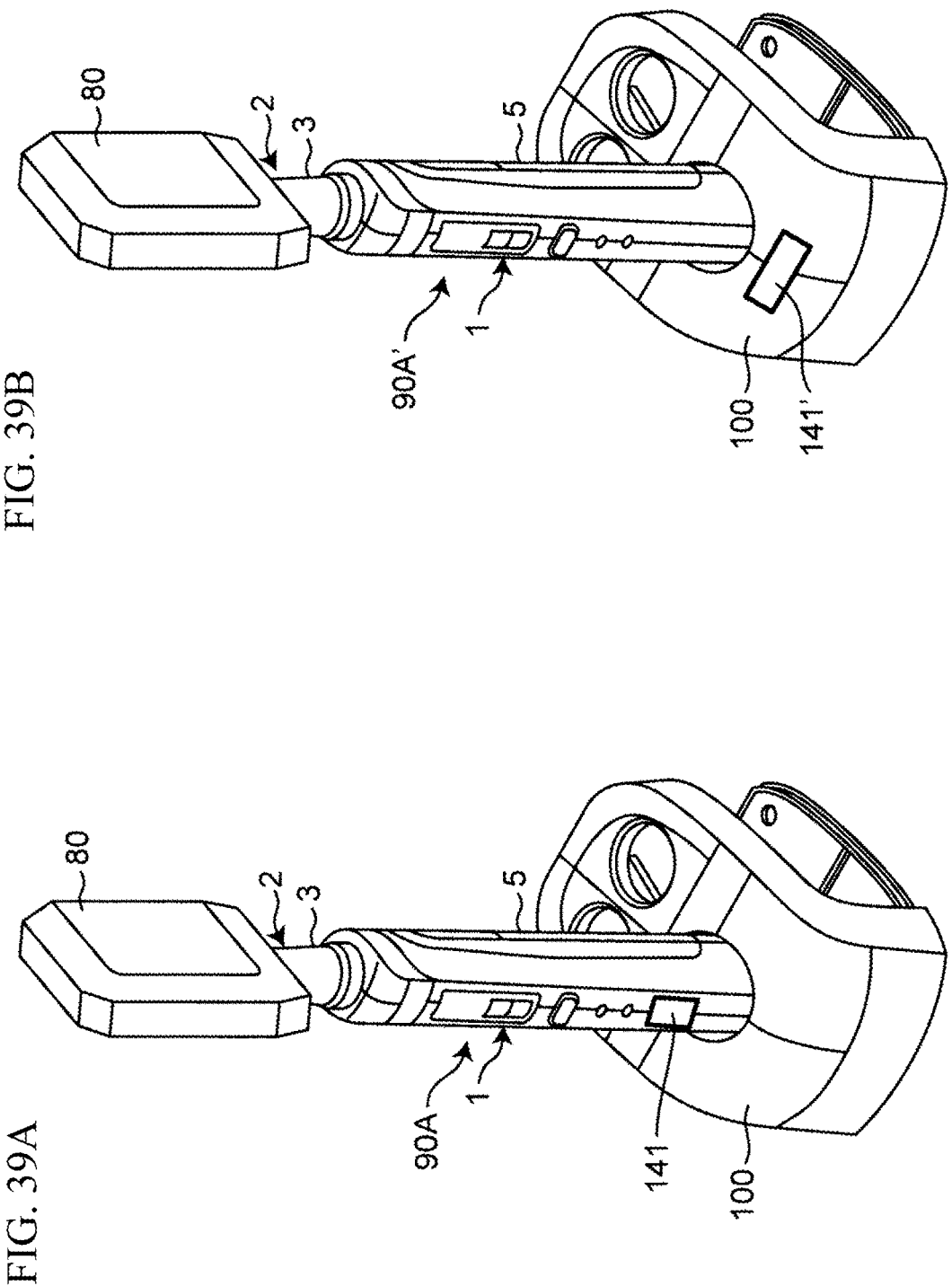

FIG. 39 (A) shows the external appearance of an electric tooth brush 90A, which is a modification of the electric tooth brush 90 described above. Furthermore, FIG. 40 shows the block configuration of the control system of this electric tooth brush 90A.

Figure 40:
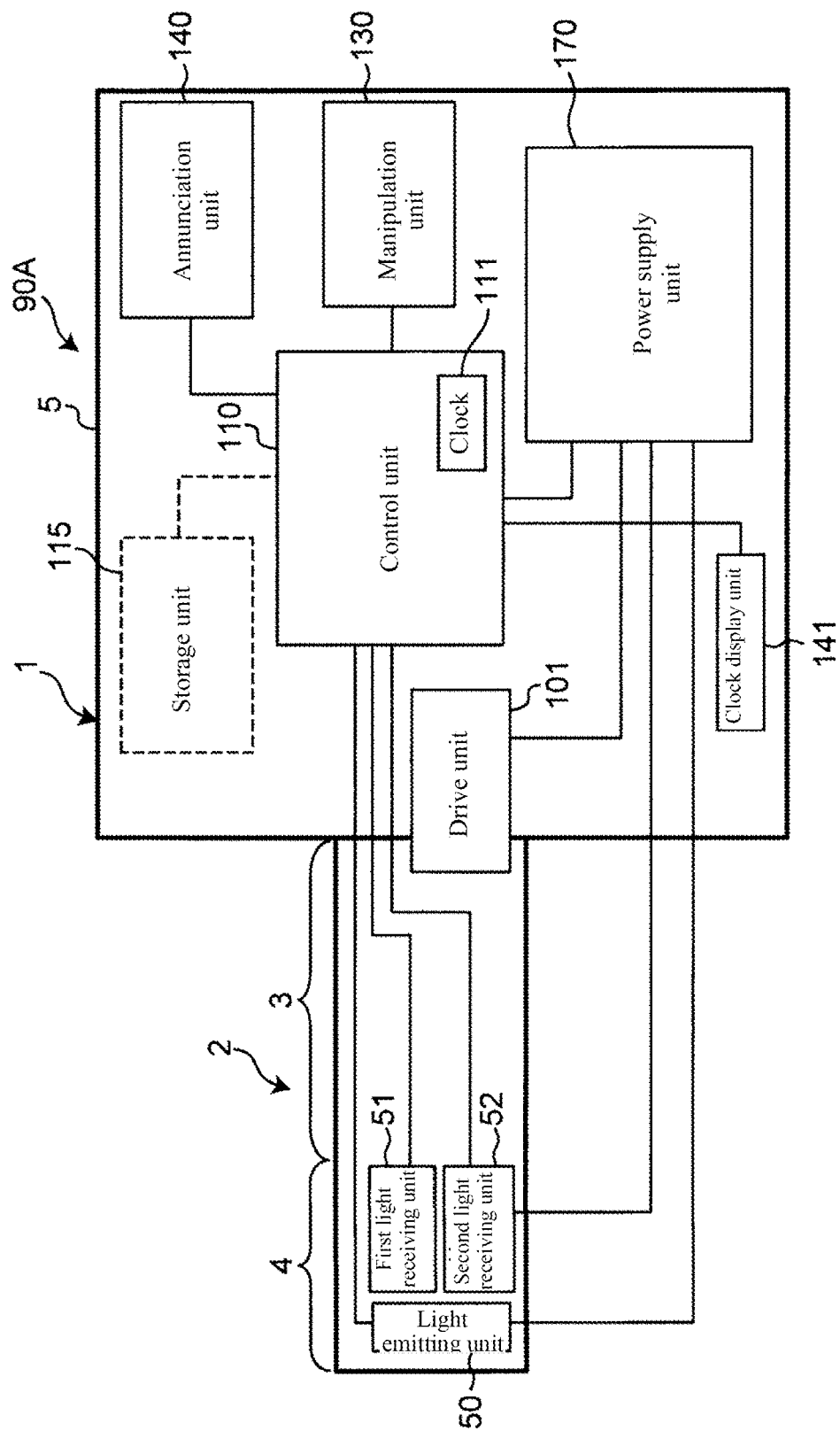
FIG. 40 is a drawing showing the block configuration of the control system of aforementioned modified example 1.

This electric tooth brush 90A, as shown in FIG. 39 (A), comprises a clock display unit (in this example, consisting of an LCD) for displaying the current time on the surface of the grip section 5 (also shown in FIG. 40). As shown in FIG. 40, the control unit 110 comprises a clock 111 which counts the current time. The clock display unit 141 is made to display the current time counted by the clock 111. In this electric tooth brush 90A, the timing (time) t at which calibration data acquisition processing is to be performed is made settable the user by means of a timer through the manipulation unit 130.

Figure 41:
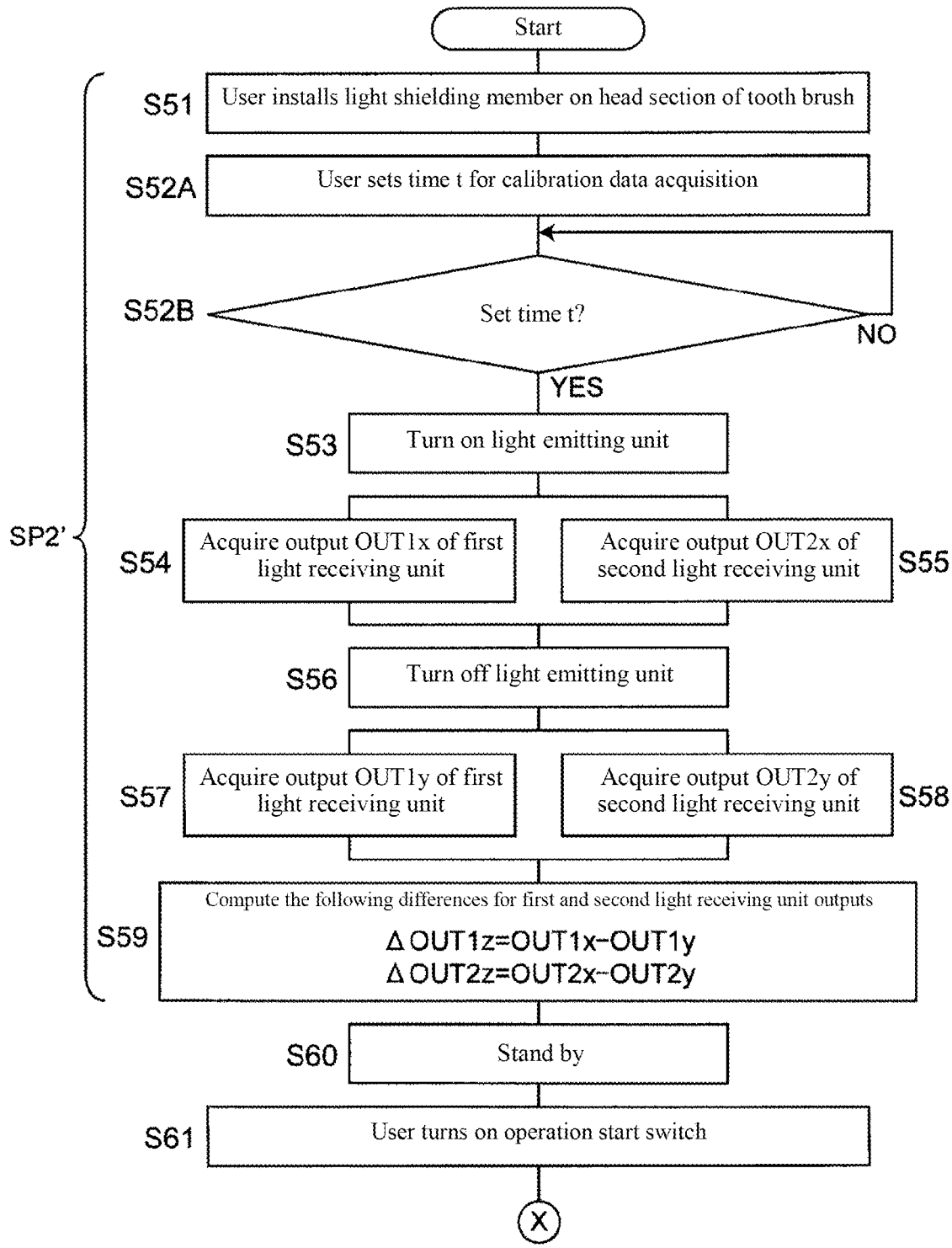
FIG. 41 is a drawing illustrating the flow of calibration data acquisition processing used in aforementioned modified example 1.

In this electric tooth brush 90A, calibration data acquisition processing (represented by reference symbol SP2') is carried out according to the processing flow shown in FIG. 41. It will be noted that, in FIG. 41, steps which are the same as steps in FIG. 35 are assigned the same step numbers.

More specifically, first, as shown in step S51 of FIG. 41, the user installs the light shielding member 80 on the head section 4 of the electric tooth brush 90A as shown in FIG. 39 (A) to place it into a light shielded state. Next, the user sets the timing (time) t at which calibration data acquisition is to be performed (step S52A of FIG. 41). Subsequently, the control unit 110 waits until the current time reaches time t based on the output of the clock 111 (step S52B of FIG. 41).

Once the current time reaches time t (YES in step S52B of FIG. 41), the control unit 110, acting as the second zero point adjustment unit, performs the processing of steps S53 through S59 of FIG. 41 to acquire the components $\Delta OUT1z$ and $\Delta OUT2z$ due to internally reflected light Li contained in the first output value OUT1 and second output value OUT2. Namely, $\Delta OUT1z = OUT1x - OUT1y$ $\Delta OUT2z = OUT2x - OUT2y$ are found. It is thereby possible to suitably obtain the components $\Delta OUT1z$, $\Delta OUT2z$ due to internally reflected light Li in the state where ambient light Lb around the head section 4 is nearly zero. The control unit 110 stores the found components $\Delta OUT1z$, $\Delta OUT2z$ due to internally reflected light Li in storage unit 115.

The control unit 110 then stands by (step S60 of FIG. 41) and waits for the user to turn on the operation start switch SW1.

Further, as shown in FIG. 15 (B), when the user places the bristles 210 of the head section 4 of the electric tooth brush 90A against the tooth surface 99a and turns the operation start switch SW1 on (step S61 of FIG. 41), the control unit 110 performs the processing of steps S101 through S112 of FIG. 36 to determine the presence or absence of plaque (or tartar) on the tooth surface 99a. Then, as shown in step S113 of FIG. 36, the control unit 110 annunciates the presence or absence of plaque (or tartar), in this example, by sounding a buzzer using the annunciation unit 140.

In this electric tooth brush 90A, just as in electric tooth brush 90 described previously, performing the zero point adjustment processing SP3 (steps S104 through S107) of FIG. 36 makes it possible to suitably eliminate the effect of the component due to ambient light Lb and the component due to internally reflected light Li and increase the accuracy of determination of the presence or absence of plaque.

It will be noted that if the time t set by means of a timer for performing calibration data acquisition processing is at night (for example, 4 am), it can be expected that the room in which the electric tooth brush 90A and charger 100 are installed will be dark and that there will be little ambient light Lb. In this case, the user can omit the process of installing the light shielding member 80 around the head section 4 to place it into a light shielded state (step S51 of FIG. 41).

Furthermore, the time at which calibration data acquisition processing is to be performed may be set in advance to nighttime (for example, 4 am) by default, rather than being set by the user by means of a timer. The need for the user to perform an operation for calibration data acquisition can thereby be eliminated.

Furthermore, the time display unit 141 does not need to be provided on the surface of the grip section 5. For example, a time display unit 141' may be provided on the surface of the charger 100, as in electric tooth brush 90A' shown in FIG. 39 (B).

Modified Example 2

Figure 42A:
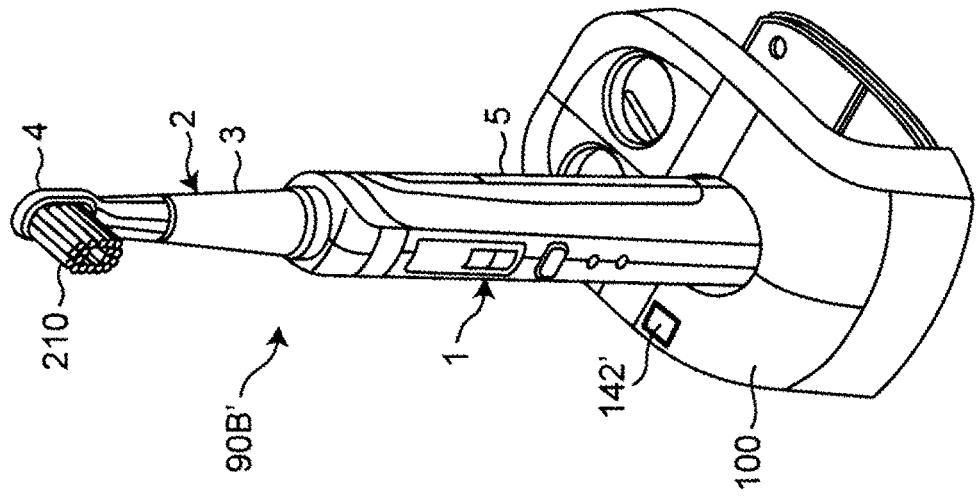
FIG. 42 FIG. 42 (A) is a drawing showing the external appearance of modified example 2, in which the aforementioned electric tooth brush has been modified.
Figure 42B:
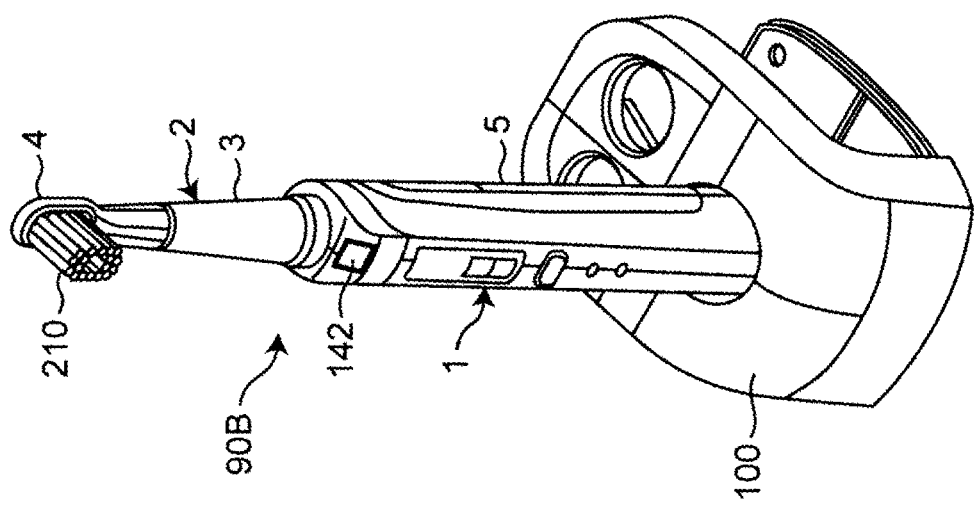

FIG. 42 (A) shows the external appearance of an electric tooth brush 90B, which is a modification of the above-described electric tooth brush 90. Furthermore, FIG. 43 shows the block configuration of the control system of this electric tooth brush 90B.

Figure 43:
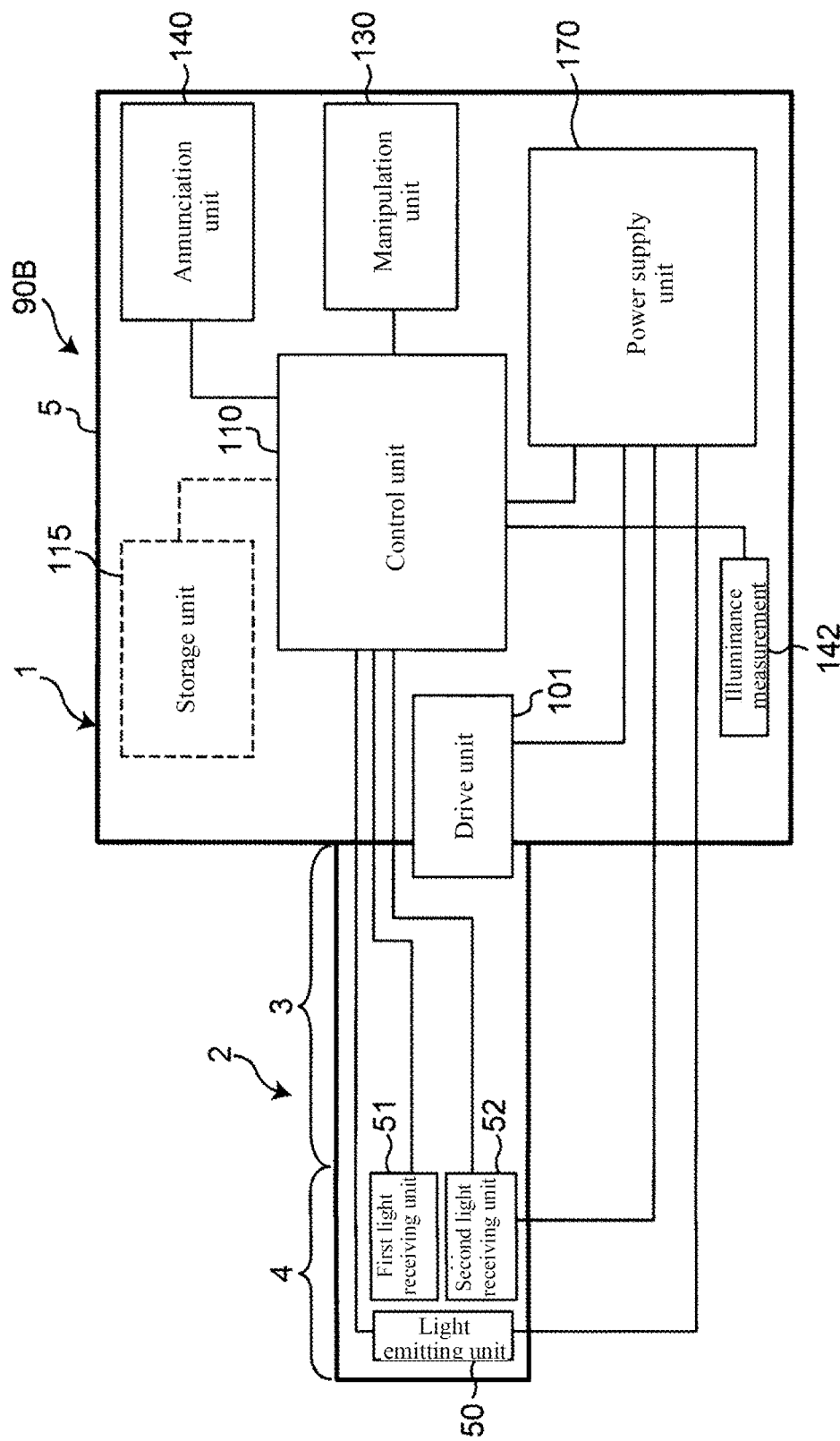
FIG. 43 is a drawing showing the block configuration of the control system of aforementioned modified example 2.

This electric tooth brush 90B comprises an illuminance measurement unit 142 (in this example, consisting of a photodiode) on the surface of the grip section 5, as shown in FIG. 42 (A) (also shown in FIG. 43). The illuminance measurement unit 142 measures and outputs the illuminance due to ambient light Lb around the main body 1 (the output representing this illuminance will be represented by the symbol OUT0). The control unit 110 is configured to determine whether or not the output OUT0 of illuminance measurement unit 142 is below a predetermined illuminance threshold value La. In this example, the illuminance threshold value La will be assumed to have been set to a level where the electric tooth brush 90B and charger 100 have been placed in a room which is dark and where there is little ambient light Lb (for example, La=125 lux).

In this electric tooth brush 90B, calibration data acquisition processing (represented by symbol SP2") is performed according to the processing flow shown in FIG. 44, under the starting condition that illuminance due to ambient light Lb around the main body 1 has fallen below a predetermined illuminance threshold value La. It will be noted that in FIG. 44, steps which are the same as steps in FIG. 35 are assigned the same step numbers.

Figure 44:
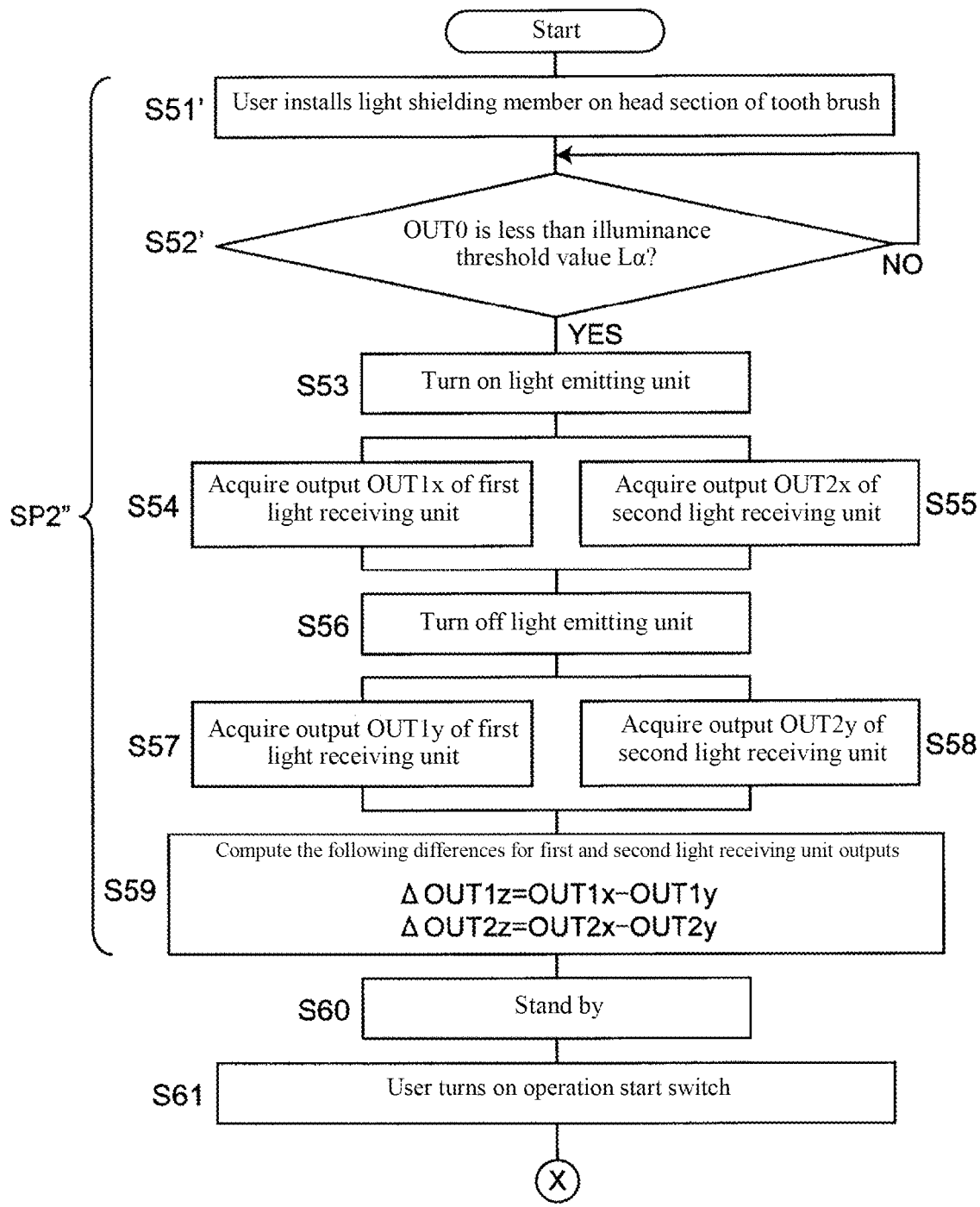
FIG. 44 is a drawing illustrating the flow of calibration data acquisition processing used in aforementioned modified example 2.

More specifically, first, as shown in step S51' of FIG. 44, the control unit 110 acquires the output OUT0 of the illuminance measurement unit 142. Next, the control unit 110 determines if the output OUT0 of the illuminance measurement unit 142 has fallen below the predetermined illuminance threshold value La (step S52" of FIG. 44). Here, if the output OUT0 which represents illuminance is at or above the illuminance threshold La (NO in step S52" of FIG. 44), the control unit 110 waits until the output OUT0 drops below the illuminance threshold value La.

When the output OUT0 of the illuminance measurement unit 142 drops below the illuminance threshold value α (YES in step S52" of FIG. 44), the control unit 110, acting as the second zero point adjustment unit, performs the processing of steps S53 through S59 of FIG. 44 and acquires the components ΔOUT1z and ΔOUT2z due to internally reflected light Li contained in the first output value OUT1 and second output value OUT2. Namely, $$\Delta OUT1z = OUT1x - OUT1y$$

$$\Delta OUT2z = OUT2x - OUT2y$$

are found. It is thereby possible to suitably obtain the components ΔOUT1z, ΔOUT2z due to internally reflected light Li in the state where ambient light Lb around the head section 4 is low. The control unit 110 stores the found components ΔOUT1z, ΔOUT2z due to internally reflected light Li in storage unit 115.

The control unit 110 then stands by (step S60 of FIG. 44) and waits for the user to turn on the operation start switch SW1.

Then, as shown in FIG. 15 (B), when the user places the bristles 210 of the head section 4 of the electric tooth brush 90B against the tooth surface 99a and turns the operation start switch SW1 on (step S61 of FIG. 44), the control unit 110 performs the processing of steps S101 through S112 of FIG. 36 to determine the presence or absence of plaque (or tartar) on the tooth surface 99a. Subsequently, as shown in step S113 of FIG. 36, the control unit 110 annunciates the presence or absence of plaque (or tartar) by sounding a buzzer using the annunciation unit 140.

In this electric tooth brush 90B, just as in electric tooth brush 90 described previously, performing the zero point adjustment processing SP3 (steps S104 through S107) in FIG. 36 makes it possible to suitably eliminate the effect of the component due to ambient light Lb and the component due to internally reflected light Li and increase the accuracy of determination of the presence or absence of plaque. Moreover, unlike in the electric tooth brush 90A described previously, the need to install a light shielding member 80 on the head section 4 can be eliminated.

It should be noted that the illuminance measurement unit 142 does not need to be provided on the surface of the grip section 5. For example, an illuminance measurement unit 142' may be provided on the surface of the charger 100, as in electric tooth brush 90B' shown in FIG. 42 (B).

Furthermore, the illuminance measurement unit 142 does not need to be provided separately from the first light receiving unit 51 and second light receiving unit 52, and may consist of either the first light receiving unit 51 or second light receiving unit 52 or both. In such a case, illuminance due to ambient light Lb can be measured without increasing the number of constituent parts of the electric tooth brush.

Modified Example 3

Figure 45:
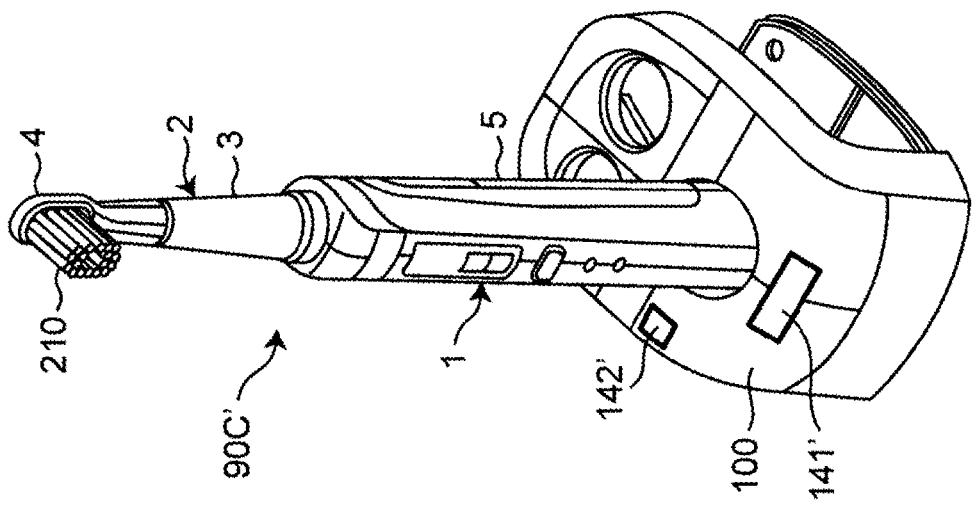
FIG. 45 (A) is a drawing showing the external appearance of modified example 3, in which the aforementioned electric tooth brush has been modified.

FIG. 45 (A) shows the external appearance of an electric tooth brush 90C, which is a modification of the above-described electric tooth brush 90. Furthermore, FIG. 46 shows the block configuration of the control system of this electric tooth brush 90C.

Figure 46:
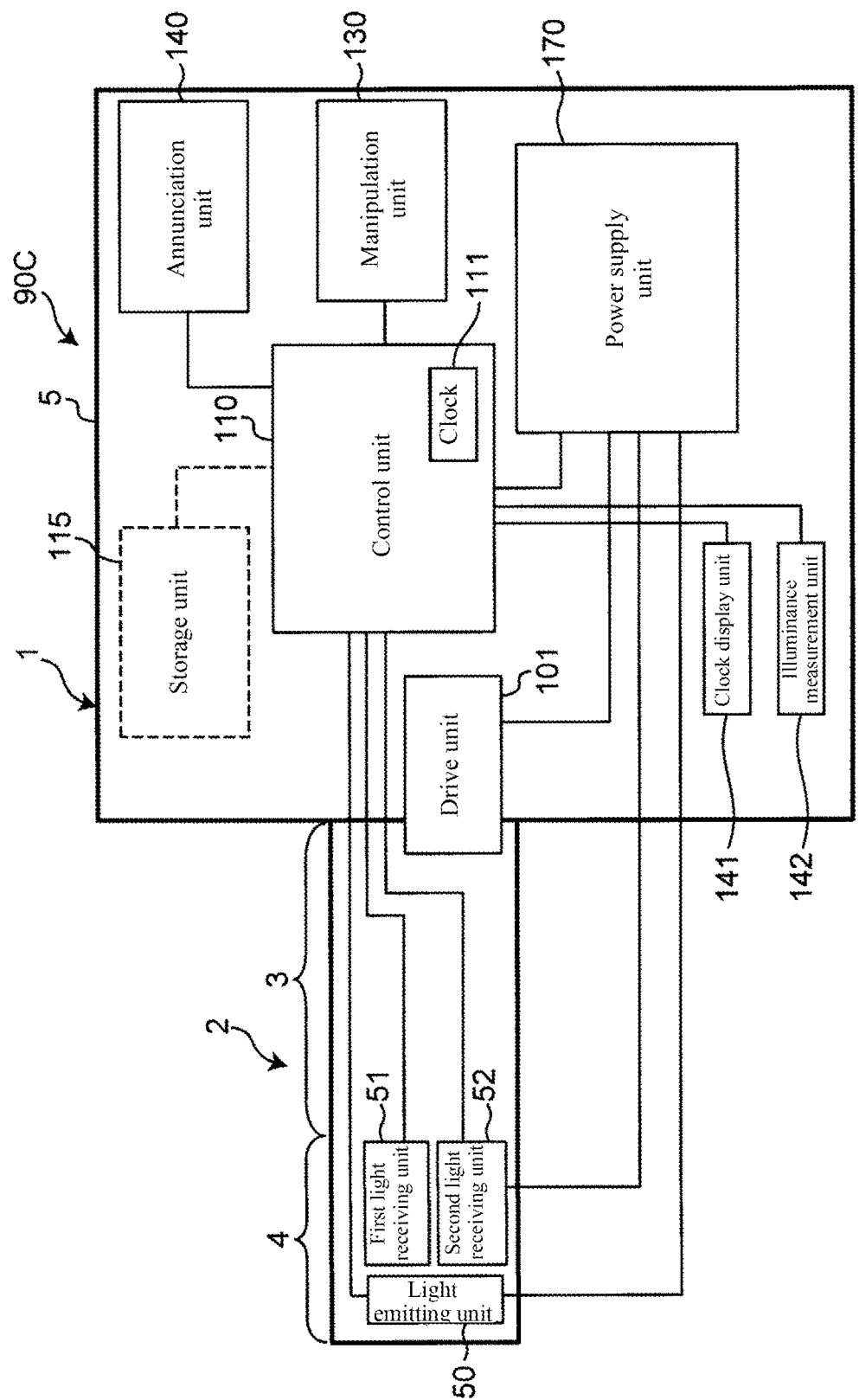
FIG. 46 is a drawing showing the block configuration of the control system of aforementioned modified example 3.

This electric tooth brush 90C comprises the time display unit 141 illustrated in FIG. 39 (A) and the illuminance measurement unit 142 shown in FIG. 42 (A) on the surface of the grip section 5, as shown in FIG. 45 (A) (also shown in FIG. 46). Furthermore, as shown in FIG. 46, the control unit 110 includes the clock 111 shown in FIG. 40.

In this electric tooth brush 90C, the control unit 110 determines if the current time has reached time t at which calibration data acquisition processing is to be performed based on the output of the clock 111. The control unit 110 also determines if the output OUT0 of the illuminance measurement unit 142 has dropped below a predetermined illuminance threshold value La. The control unit 110 then performs calibration data acquisition processing under the starting condition that the current time has reached time t and that illuminance due to ambient light Lb around the main body 1 has dropped below a predetermined illuminance threshold value La. Namely, it acquires the components ΔOUT1z, ΔOUT2z due to internally reflected light Li in the head section 4.

It is thereby possible to suitably obtain the components ΔOUT1z, ΔOUT2z due to internally reflected light Li in a state where ambient light Lb around the head section 4 is reliably low.

In this electric tooth brush 90C, just as in electric tooth brush 90 described previously, performing the zero point adjustment processing SP3 (steps S104 through S107) of FIG. 36 makes it possible to suitably eliminate the effect of the component due to ambient light Lb and the component due to internally reflected light Li and increase the accuracy of determination of the presence or absence of plaque. Moreover, just as in the previously described electric tooth brush 90B, the need to install a light shielding member 80 on the head section 4 can be eliminated. This makes it possible to eliminate the need for the user to perform operations for calibration data acquisition.

It should be noted that the time display unit 141 and illuminance measurement unit 142 do not need to be provided on the surface of the grip section 5. For example, a time display unit 141' and illuminance measurement unit 142' may be provided on the surface of the charger 100, as in electric tooth brush 90C' shown in FIG. 45 (B).

In the electric tooth brushes described above, the detection results concerning the presence or absence of plaque were annunciated to the user by means of an annunciation unit 140 provided on the main body 1, but the invention is not limited to this. For example, a communication unit capable of wireless or wired communication may be provided in the main body 1, and data representing the detection results concerning the presence or absence of plaque may be outputted via this communication unit to an external smartphone or other device which is essentially a computer device. In this case, detection results concerning the presence or absence of plaque can be displayed on the display screen of that computer device.

Furthermore, in the above embodiments, an electric tooth brush was discussed, but the invention is not limited to this. The plaque detecting device of this invention can also be incorporated into a manual tooth brush.

The above embodiments are illustrations, and various modifications are possible without departing from the scope of this invention. While the embodiments described above can be accomplished independently, combinations of embodiments are also possible. Furthermore, while the various features in the different embodiments can be accomplished independently, it is also possible to combine features from different embodiments.

DESCRIPTION OF REFERENCE SYMBOLS

50 Light emitting unit
51 First light receiving unit
52 Second light receiving unit
80 Light shielding member
90, 90A, 90A', 90B, 90B', 90C, 90C' Electric tooth brush
110, 410 Control unit
141, 141' Time display unit
142, 142' Illuminance measurement unit
170, 470 Power supply unit
400 Plaque detecting device
402 Spectrometer
480 Stabilized power supply

The invention claimed is:

1. A plaque detecting device comprising:
a light emitting unit which emits excitation light toward a surface of a tooth;
a first light receiving unit which receives radiated light from the tooth surface induced by the excitation light, wherein the first light receiving unit extracts, from said radiated light, a first wavelength region, and obtains a first output value corresponding to an intensity of the radiated light in the first wavelength region;
a second light receiving unit which receives radiated light from the tooth surface induced by the excitation light, wherein the second light receiving unit extracts, from said radiated light, a second wavelength region, and obtains a second output value corresponding to an intensity of the radiated light in the second wavelength region;
a first zero point adjustment unit which measures a first ambient output value and a second ambient output value when the light emitting unit is not emitting excitation light.

2. The plaque detecting device of claim 1 wherein the first wavelength region has a first lower limit and the second wavelength region has a second lower limit, the second lower limits being less than the first lower limit.

3. The plaque detecting device of claim 1 wherein the first zero point adjustment unit subtracts the first and second ambient output values from the measured first and second output values.

4. The plaque detecting device of claim 1 further comprising a signal processing unit, the signal processing unit modifying the first output value by a first coefficient and the second output value by a second coefficient, the first and second coefficients being different.

5. The plaque detecting device of claim 1 wherein the first light receiving unit has a first light receiving surface area and the second light receiving unit has a second light receiving surface area, wherein the first and second light receiving surface areas are different.

6. The plaque detecting device of claim 1 further comprising an annunciation unit, the annunciation unit comprising a lamp.

7. A toothbrush comprising:
a main body comprising a head section, a grip section, and a neck section joining the head section to the grip section, the head comprising a bristled surface and a plurality of bristles extending therefrom; and
the plaque detecting device of claim 1.

8. The toothbrush of claim 7 further comprising a light shielding member configured to cover the first light receiving unit and the second light receiving unit of the toothbrush and a second zero point adjustment unit configured to measure a first reflected light component and a second reflected light component and subtract the first and second reflected light components from the first and second output values.

9. The toothbrush of claim 7 wherein the light emitting unit, the first light receiving unit, and the second light receiving unit are located in the head section.

10. The toothbrush of claim 9 wherein the light emitting unit emits light from a bristled surface of the head section of the toothbrush.

11. A method of detecting plaque comprising:
a) providing a light emitting unit, first and second light receiving units, and a first zero point adjustment unit;
b) activating the light emitting unit to emit excitation light toward a surface of a tooth;
c) receiving radiated light via the first and second light receiving units;
d) extracting first and second wavelength regions from the radiated light via the first and second light receiving units;
e) obtaining first and second radiated output values corresponding to intensities of the first and second wavelength regions via the first and second light receiving units;
f) deactivating the light emitting unit;
g) receiving ambient light via the first and second light receiving units;
h) extracting first and second wavelength regions from the ambient light via the first and second light receiving units;
i) obtaining first and second ambient output values corresponding to intensities of the first and second wavelength regions via the first and second light receiving units;
j) computing first and second output values by subtracting the first and second ambient output values from the first and second radiated output values.

12. The method of claim 11 wherein the first wavelength region has a first lower limit and the second wavelength region has a second lower limit, the second lower limits being less than the first lower limit.

13. The method of claim 11 wherein step a) further comprises a signal processing unit; and further comprising step j-2) wherein the signal processing unit modifies the first and second output values by first and second coefficients, the first and second coefficients being different.

14. The method of claim 11 wherein step a) further comprises a toothbrush comprising a head section, the light emitting unit located in the head section of the toothbrush.

* * * * *